US010986986B2

(12) United States Patent
Hanzawa

(10) Patent No.: US 10,986,986 B2
(45) Date of Patent: Apr. 27, 2021

(54) SOLID-STATE IMAGE PICKUP ELEMENT, IMAGE PICKUP APPARATUS, AND METHOD OF CONTROLLING SOLID-STATE IMAGE PICKUP ELEMENT

(71) Applicant: SONY SEMICONDUCTOR SOLUTIONS CORPORATION, Kanagawa (JP)

(72) Inventor: Katsuhiko Hanzawa, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 18 days.

(21) Appl. No.: 16/316,462

(22) PCT Filed: Jun. 9, 2017

(86) PCT No.: PCT/JP2017/021440
§ 371 (c)(1),
(2) Date: Jan. 9, 2019

(87) PCT Pub. No.: WO2018/020857
PCT Pub. Date: Feb. 1, 2018

(65) Prior Publication Data
US 2019/0239731 A1   Aug. 8, 2019

(30) Foreign Application Priority Data

Jul. 27, 2016 (JP) .............................. JP2016-146859

(51) Int. Cl.
*A61B 1/045* (2006.01)
*G02B 21/36* (2006.01)
(Continued)

(52) U.S. Cl.
CPC .............. *A61B 1/045* (2013.01); *G02B 21/36* (2013.01); *G02B 21/361* (2013.01); *G02B 23/24* (2013.01);
(Continued)

(58) Field of Classification Search
CPC . A61B 1/045; A61B 1/00039; A61B 1/00186; A61B 1/0005; A61B 1/042;
(Continued)

(56) References Cited

U.S. PATENT DOCUMENTS

2010/0091160 A1* 4/2010 Murakami ............. H04N 5/378
348/301
2014/0022427 A1   1/2014 Goto et al.
2017/0094202 A1* 3/2017 Kobayashi ........ H01L 27/14612

FOREIGN PATENT DOCUMENTS

CN   103581579 A   2/2014
JP   2006-295666 A   10/2006
(Continued)

OTHER PUBLICATIONS

International Search Report and Written Opinion of PCT Application No. PCT/JP2017/021440, dated Aug. 29, 2017, 06 pages of ISRWO.

*Primary Examiner* — Lin Ye
*Assistant Examiner* — Chan T Nguyen
(74) *Attorney, Agent, or Firm* — Chip Law Group

(57) ABSTRACT

To reduce power consumption in a solid-state image pickup element that performs pixel addition. A solid-state image pickup element includes a predetermined number of blocks, each of which is provided with a plurality of normal pixels arranged in a predetermined direction, and a light shielding area in which the predetermined number of light shielding pixels are arranged in the predetermined direction, the light shielding pixels being connected to the respective blocks. A
(Continued)

scanning circuit that controls each of the plurality of normal pixels in the block so that the block transfers electric charge to the light shielding pixel corresponding to the block. A signal processing unit is provided, for each of the light shielding pixels, with a signal processing circuit that processes a signal generated by the light shielding pixel on the basis of the transferred electric charge.

11 Claims, 34 Drawing Sheets

(51) Int. Cl.
    *H01L 27/146*     (2006.01)
    *G02B 23/24*     (2006.01)
    *H04N 5/347*     (2011.01)
    *H04N 5/369*     (2011.01)
    *H04N 5/3745*     (2011.01)

(52) U.S. Cl.
    CPC ....... *G02B 23/243* (2013.01); *G02B 23/2415* (2013.01); *H01L 27/14612* (2013.01); *H04N 5/347* (2013.01); *H04N 5/36963* (2018.08); *H04N 5/3745* (2013.01); *H04N 5/37457* (2013.01)

(58) Field of Classification Search
    CPC . A61B 1/3132; A61B 1/0638; A61B 1/00163; A61B 1/0669; A61B 1/00009; A61B 1/00149; H04N 5/36963; H04N 5/3745; H04N 5/37457; H04N 5/347; H01L 27/14612; G02B 21/0012; G02B 23/24; G02B 21/36; G02B 21/361; G02B 23/243; G02B 23/2415
    USPC ....................................................... 348/294
    See application file for complete search history.

(56) References Cited

FOREIGN PATENT DOCUMENTS

| | | |
|---|---|---|
| JP | 2014-209696 A | 11/2014 |
| JP | 2015-211259 A | 11/2015 |
| WO | 2015/163170 A1 | 10/2015 |

\* cited by examiner

SOLID-STATE IMAGE PICKUP ELEMENT, IMAGE PICKUP APPARATUS, AND METHOD OF CONTROLLING SOLID-STATE IMAGE PICKUP ELEMENT

CROSS REFERENCE TO RELATED APPLICATIONS

This application is a U.S. National Phase of International Patent Application No. PCT/JP2017/021440 filed on Jun. 9, 2017, which claims priority benefit of Japanese Patent Application No. JP 2016-146859 filed in the Japan Patent Office on Jul. 27, 2016. Each of the above-referenced applications is hereby incorporated herein by reference in its entirety.

TECHNICAL FIELD

The present technology relates to solid-state image pickup elements, image pickup apparatuses, and methods of controlling the solid-state image pickup element. More specifically, the present technology relates to a solid-state image pickup element, image pickup apparatus, and method of controlling the solid-state image pickup element, which adds a plurality of pixel signals.

BACKGROUND ART

Solid-state image pickup elements are developed to achieve high functionality and sophistication nowadays, and solid-state image pickup elements equipped with a motion detection function of detecting motion of a photographic subject and a function of detecting illuminance are appeared. It is generally necessary for such motion detection or illuminance detection to have higher SN ratio, lower power consumption, and a higher dynamic range as compared with the case of capturing image data, but it does not necessary to have high resolution or high frame rate. In view of this, a solid-state image pickup element that adds pixel signals of a plurality of pixels and reads out it in detecting motion or illuminance is developed (e.g., see Patent Literature 1).

CITATION LIST

Patent Literature

Patent Literature 1: JP 2014-209696A

DISCLOSURE OF INVENTION

Technical Problem

In the related art described above, a pixel array section is divided into a plurality of pixel blocks, each of which has pixels of array of 2-by-2 (two rows and two columns), and pixel signals of four pixels in a pixel block are added. This pixel addition reduces the number of times of readout of rows by half as compared with the case of with no pixel addition, so it is possible to reduce the power consumption in capturing by the solid-state image pickup element. However, it is difficult for the related art described above to reduce further the power consumption. In other words, if the size of a pixel block increases to an array of 3-by-3 (three rows and three columns) or the like and the number of times of readout of rows is further reduced, it is possible to reduce the power consumption, but accordingly, the accuracy of motion detection or illuminance detection is likely to be lowered. As described above, there is a problem that power consumption fails to be reduced while maintaining the accuracy of motion detection or the like.

The present technology is developed in view of such a situation, and is intended to reduce power consumption in a solid-state image pickup element that performs pixel addition.

Solution to Problem

The present technology is made in order to solve the above problem. A first aspect of the present technology is a solid-state image pickup element and a control method thereof, the solid-state image pickup element including: a predetermined number of blocks, each of which is provided with a plurality of normal pixels arranged in a predetermined direction; a light shielding area in which the predetermined number of light shielding pixels are arranged in the predetermined direction, the light shielding pixels being connected to the respective blocks; a scanning circuit configured to control each of the plurality of normal pixels in the block so that the block transfers electric charge to the light shielding pixel corresponding to the block; and a signal processing unit provided, for each of the light shielding pixels, with a signal processing circuit configured to process a signal generated by the light shielding pixel on the basis of the transferred electric charge. This leads to an effect that the electric charge is transferred from the block to the associated light shielding pixel and the signal generated by the light shielding pixel is processed.

In addition, in this first aspect, the normal pixel may include a floating diffusion layer configured to accumulate the electric charge, and a connection transistor configured to connect the light shielding pixel and the floating diffusion layer. This leads to an effect that the electric charge is transferred from the floating diffusion layer to the light shielding pixel.

In addition, in this first aspect, the normal pixel may further include a reset transistor configured to initialize an amount of the electric charge of the floating diffusion layer. This leads to an effect that the electric charge of the floating diffusion layer is initialized.

In addition, in this first aspect, the connection transistor may be a reset transistor configured to initialize the floating diffusion layer. This leads to an effect that the electric charge is initialized and transferred by the reset transistor.

In addition, in this first aspect, the row scanning circuit may simultaneously transmit a reset signal used to instruct the floating diffusion layer to be initialized and a connection signal used to instruct the floating diffusion layer to be connected. This leads to an effect that the initialized floating diffusion layer is connected.

In addition, in this first aspect, the row scanning circuit may transmit a reset signal used to instruct the floating diffusion layer to be initialized and then transmit a connection signal used to instruct the floating diffusion layer to be connected. This leads to an effect that the floating diffusion layer is connected after the initialization.

In addition, in this first aspect, the normal pixel may include a photoelectric transducer configured to photoelectrically convert light to generate the electric charge, and a connection transistor configured to connect the light shielding pixel and the photoelectric transducer. This leads to an effect that the electric charge is transferred from the photoelectric transducer to the light shielding pixel.

In addition, in this first aspect, the light shielding pixel may include an electric charge accumulation unit configured to accumulate the transferred electric charge, and an amplification transistor configured to amplify a signal corresponding to an amount of the accumulated electric charge. This leads to an effect that the signal corresponding to the quantity of transferred electric charge is amplified.

In addition, in this first aspect, the light shielding pixel may further include a photoelectric transducer. This leads to an effect that the electric charge is transferred to the light shielding pixel having similar circuit configuration to the normal pixel.

In addition, in this first aspect, each of the blocks may include a plurality of pixel blocks each provided with the plurality of normal pixels sharing a floating diffusion layer. This leads to an effect that the respective signals of the plurality of pixel blocks are added.

In addition, in this first aspect, one of a pair of adjacent normal pixels among the plurality of normal pixels may transfer the electric charge to another normal pixel of the pair of normal pixels under control of the row scanning circuit. This leads to an effect that the electric charge is transferred from one of a pair of adjacent normal pixels to the other.

In addition, a second aspect of the present technology is an image pickup apparatus including: a predetermined number of blocks, each of which is provided with a plurality of normal pixels arranged in a predetermined direction; a light shielding area in which the predetermined number of light shielding pixels are arranged in the predetermined direction, the light shielding pixels being connected to the respective blocks; a scanning circuit configured to control each of the plurality of normal pixels in the block so that the block transfers electric charge to the light shielding pixel corresponding to the block; a signal processing unit provided, for each of the light shielding pixels, with a signal processing circuit configured to create data by processing a signal generated by the light shielding pixel on the basis of the transferred electric charge; and a recording unit configured to record the created data. This leads to an effect that the electric charge is transferred from the block to the associated light shielding pixel and the data created from the signal generated by the light shielding pixel is recorded.

Advantageous Effects of Invention

According to the present technology, it is possible to achieve advantageous effects capable of reducing power consumption in a solid-state image pickup element that performs pixel addition. Note that effects described herein are not necessarily limitative, and any effect that is desired to be described in the present disclosure may be admitted.

MODE(S) FOR CARRYING OUT THE INVENTION

The modes for carrying out the present technology (hereinafter referred to as embodiments) are described below. The description is given in the following order.
1. First Embodiment (example of transfer of electric charge from pixel block to light shielding pixel)
2. Second Embodiment (example of transfer of electric charge from pixel block to light shielding pixel by reset transistor)
3. Third Embodiment (example of transfer of electric charge from pixel block to light shielding pixel with no photoelectric transducer)
4. Fourth Embodiment (example of transfer of electric charge from photoelectric transducer in pixel block to light shielding pixel)
5. Fifth Embodiment (example of transfer of electric charge from addition block to light shielding pixel)
6. Sixth Embodiment (example of transfer of electric charge between a pair of pixels and transfer of electric charge from pixel block to light shielding pixel)

1. First Embodiment

Configuration Example of Image Pickup Apparatus

Figure 1:
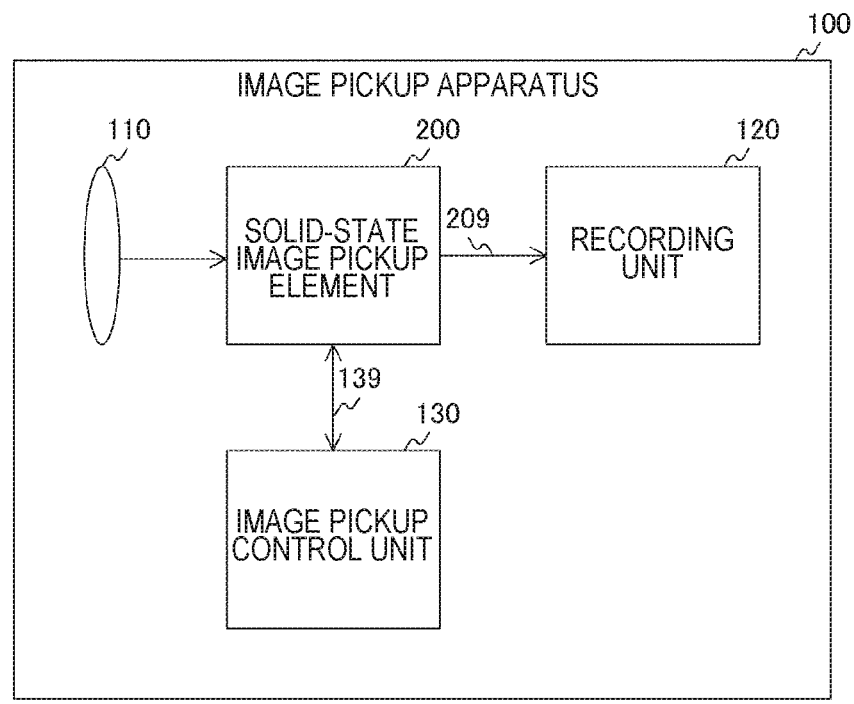
FIG. 1 is a block diagram depicting a configuration example of an image pickup apparatus according to a first embodiment of the present technology.

FIG. 1 is a block diagram depicting a configuration example of an image pickup apparatus 100 according to a first embodiment. The image pickup apparatus 100 is an apparatus that captures image data, and includes an image pickup lens 110, a solid-state image pickup element 200, a recording unit 120, and an image pickup control unit 130. It is assumed that an action camera, an in-vehicle camera, or the like is used as the image pickup apparatus 100.

The image pickup lens 110 condenses light and guides it to the solid-state image pickup element 200. The solid-state image pickup element 200 creates image data under the control of the image pickup control unit 130. The solid-state image pickup element 200 supplies the created image data to the recording unit 120 via a signal line 209. The recording unit 120 records the image data.

The image pickup control unit 130 controls the entire image pickup apparatus 100. The image pickup control unit 130 supplies a vertical synchronization signal or the like indicating the image pickup timing to the solid-state image pickup element 200 via a signal line 139.

Moreover, the image pickup lens 110, the solid-state image pickup element 200, the recording unit 120, and the image pickup control unit 130 are disposed in the same apparatus, but it is possible to dispose dispersedly them in a plurality of apparatus. In one example, the image pickup lens 110 can be disposed in a lens unit, and the solid-state image pickup element 200 and other components can be disposed in the image pickup apparatus 100.

Configuration Example of Solid-State Image Pickup Element

Figure 2:
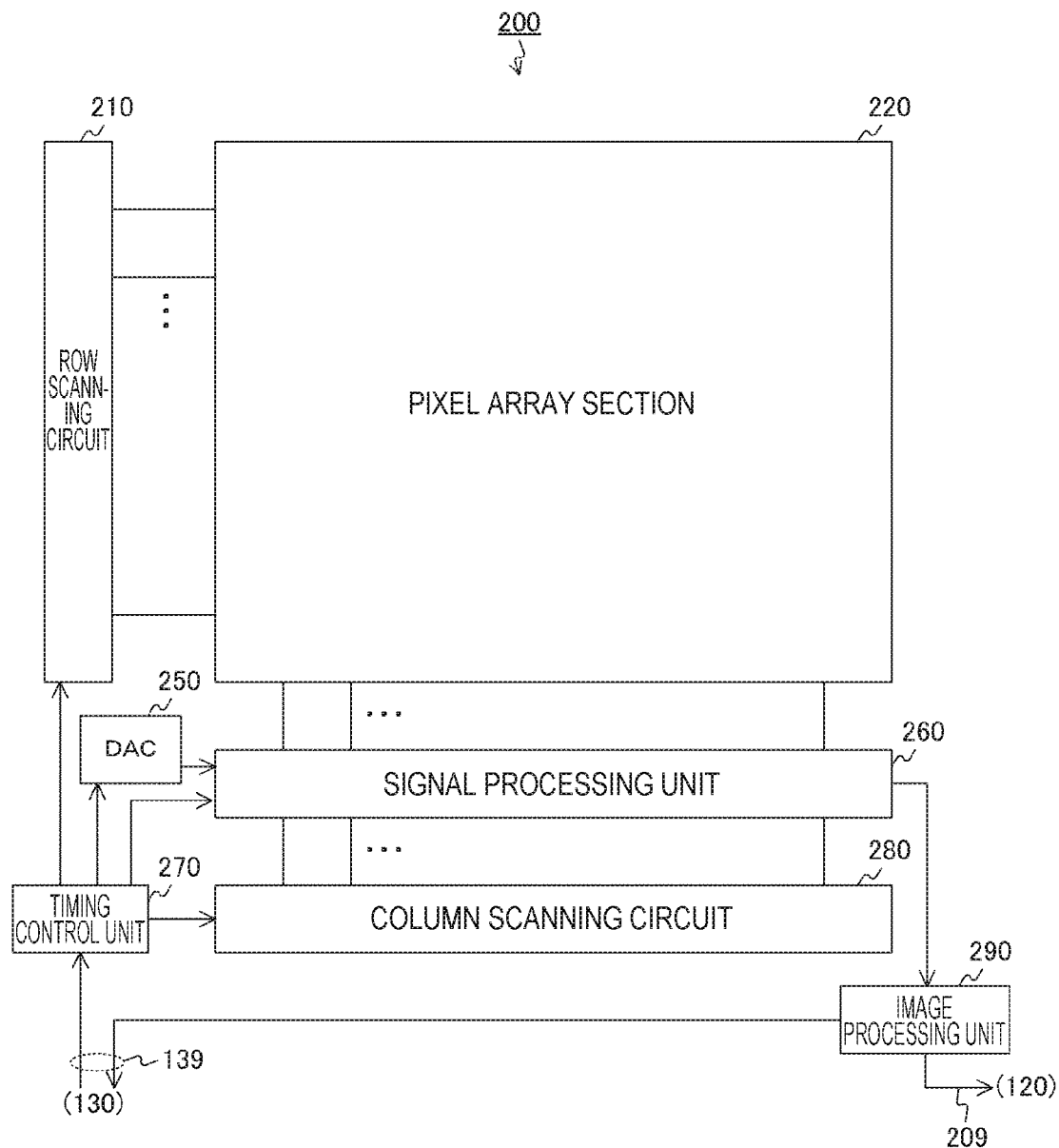
FIG. 2 is a block diagram depicting a configuration example of a solid-state image pickup element according to the first embodiment of the present technology.

FIG. 2 is a block diagram depicting a configuration example of the solid-state image pickup element 200 according to the first embodiment. The solid-state image pickup element 200 includes a row scanning circuit 210, a pixel array section 220, a digital-to-analog converter (DAC) 250, a signal processing unit 260, a timing control unit 270, a column scanning circuit 280, and an image processing unit 290.

Further, the pixel array section 220 is provided with a plurality of pixel circuits in a two-dimensional grid pattern. A set of pixel circuits arranged in a predetermined direction (e.g., horizontal direction) is hereinafter referred to as a "row", and a set of pixel circuits arranged in a direction perpendicular to the row is hereinafter referred to as a "column". Moreover, the pixel array section 220 is an example of an array section set forth in the claims.

The row scanning circuit 210 drives the pixel circuits and causes the pixel circuits to output pixel signals. In addition, the row scanning circuit 210 controls the pixel array section 220 and causes the pixel array section 220 to add pixel signals of a plurality of adjacent pixels as necessary. Moreover, the row scanning circuit 210 is an example of a scanning circuit set forth in the claims.

The timing control unit 270 controls the timing at which each of the row scanning circuit 210, the signal processing unit 260, and the column scanning circuit 280 operates. The DAC 250 generates a ramp signal by digital-to-analog (DA) conversion and supplies it to the signal processing unit 260.

The signal processing unit 260 performs signal processing such as AD conversion on the pixel signal to create pixel data. The column scanning circuit 280 controls the signal processing unit 260 and causes the signal processing unit 260 to transfer pixel data to the image processing unit 290.

The image processing unit 290 executes various image processing on image data including the pixel data. As an example of this image processing, demosaicing, white balancing, or the like is executed. The image data subjected to the image processing is transmitted to the recording unit 120. In addition, in a case where pixel addition is performed, motion detection processing or illuminance detection processing is executed. In the motion detection processing, the presence or absence of motion, a motion vector, or the like of a photographic subject in an image is detected using an inter-frame difference method, a background difference method, or the like. The illuminance detection processing obtains a photometric amount corresponding to the illuminance, in one example, by calculation for weighted addition of data for each addition unit.

The result obtained by detecting the motion or illuminance is transmitted to the image pickup control unit 130.

The motion detection result is used for various applications such as an application for changing a frame rate in a case where there is motion. In addition, the illuminance detection result is used for control of an exposure amount or the like.

Moreover, although the image processing unit 290 is disposed in the solid-state image pickup element 200, the image processing unit 290 can be disposed outside the solid-state image pickup element 200.

Further, the respective circuits in the solid-state image pickup element 200 can be disposed on a single semiconductor substrate, or can be disposed dispersedly on a plurality of stacked semiconductor substrates.

Configuration Example of Pixel Array Section

Figure 3:
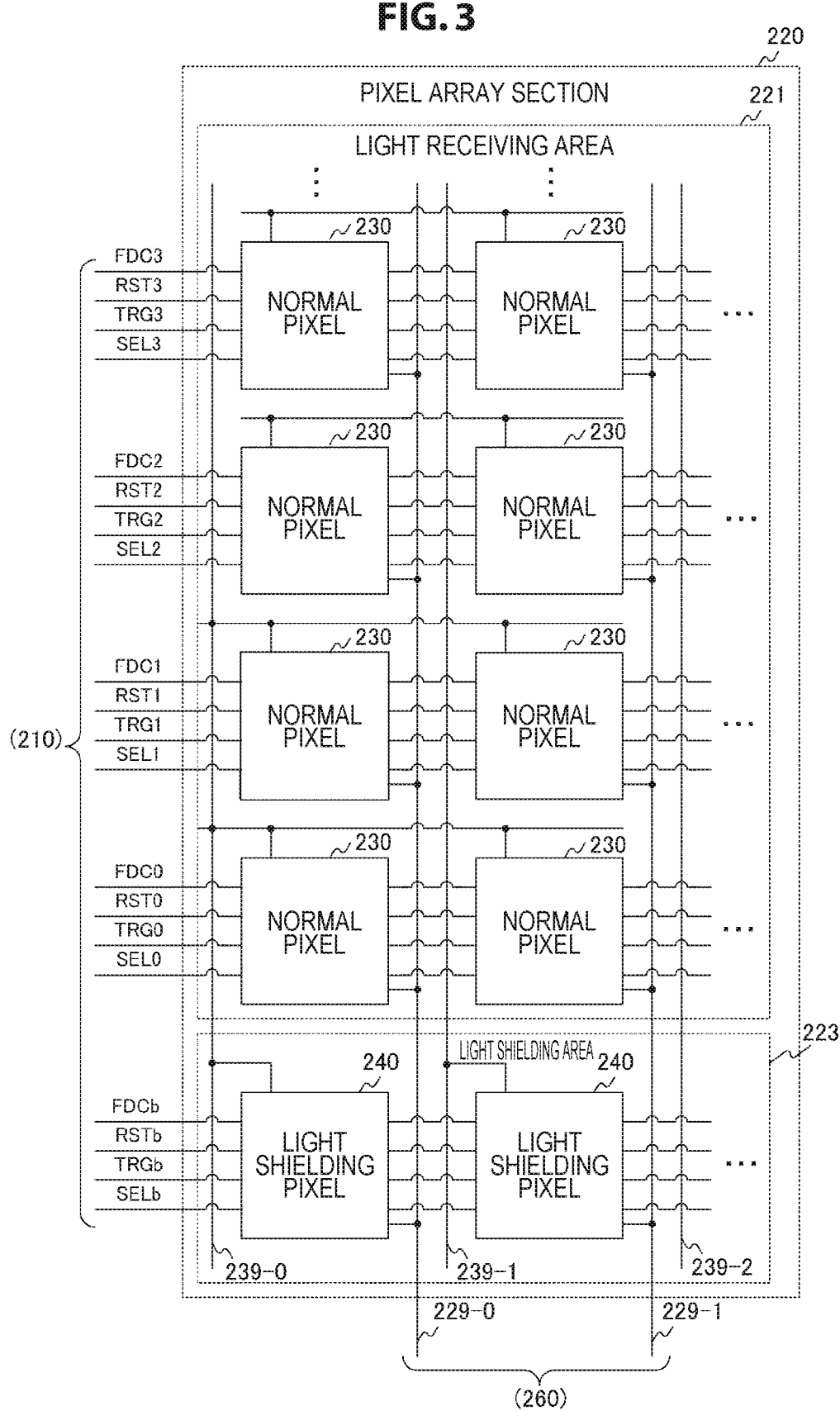
FIG. 3 is a plan view depicting a configuration example of a pixel array section according to the first embodiment of the present technology.

FIG. 3 is a plan view depicting a configuration example of the pixel array section 220 according to the first embodiment. The pixel array section 220 is divided into a light receiving area 221 where light is not blocked and a light shielding area 223 where light is blocked. The light receiving area 221 has a plurality of normal pixels 230 arranged in a two-dimensional grid pattern. The light shielding area 223 has a light shielding pixel 240 arranged for each column of a normal pixel 230. This light shielding pixel 240 is also called an optical black (OPB) pixel or a dummy pixel.

Assuming that the number of rows of the normal pixel 230 is N (N is an integer) and the number of columns of the normal pixel 230 is M (M is the number of columns), M light shielding pixels 240 are arranged in the horizontal direction.

In the pixel array section 220, a connection line 239-$m$ (m is an integer from 0 to M−1) and a vertical signal line 229-$m$ are wired in the vertical direction for each column. In addition, four horizontal signal lines are wired for each row of the normal pixel 230 in the horizontal direction.

The four horizontal signal lines transmit respective corresponding signals, i.e. a connection signal FDCn (n is an integer from 0 to N−1), a reset signal RSTn, a transfer signal TRGn, and a selection signal SELn. The connection signals FDCn, the reset signals RSTn, the transfer signals TRGn, and the selection signals SELn are generated by the row scanning circuit 210 and supplied to n rows.

Further, the connection signals FDCn are signals for instructing a floating diffusion layer in the normal pixel 230 and the connection line 239-$m$ to be connected to each other, and the reset signals RSTn are signals for instructing the quantity of electric charge of the floating diffusion layer to be initialized. The transfer signals TRGn are signals for instructing electric charge in the normal pixel 230 to be transferred, the selection signals SELn are signals for instructing the pixel signal via the vertical signal line 229-$m$ to be output.

Four horizontal signal lines are also wired to the row of the light shielding pixel 240. These four horizontal signal lines transmits respective corresponding signals, i.e. a connection signal FDCb, a reset signal RSTb, a transfer signal TRGb, and a selection signal SELb. The connection signal FDCb, the reset signal RSTb, the transfer signal TRGb, and the selection signal SELb are generated by the row scanning circuit 210.

The connection signal FDCb is a signal for instructing the floating diffusion layer in the light shielding pixel 240 and the connection line 239-$m$ to be connected to each other, and the reset signal RSTb is a signal for instructing the quantity of electric charge of the floating diffusion layer to be initialized. The transfer signal TRGb is a signal for instructing the electric charge in the light shielding pixel 240 to be transferred, and the selection signal SELb is a signal for instructing a pixel signal via the vertical signal line 229-$m$ to be output.

Configuration Example of Signal Processing Unit

Figure 4:
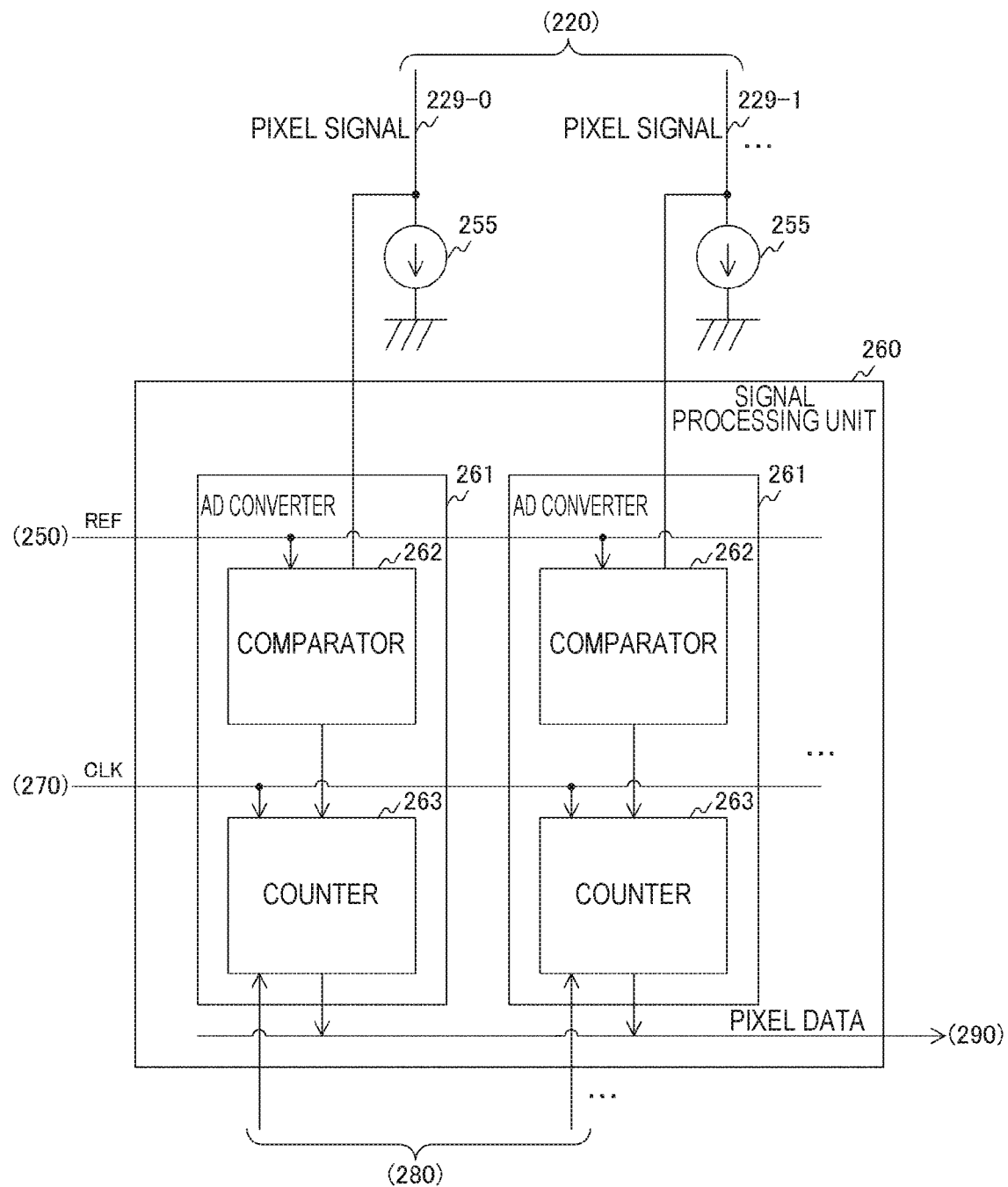
FIG. 4 is a block diagram depicting a configuration example of a signal processing unit according to the first embodiment of the present technology.

FIG. 4 is a block diagram depicting a configuration example of the signal processing unit 260 according to the first embodiment. The signal processing unit 260 is provided with an AD converter 261 for each column. The number of columns is M, so M analog-to-digital (AD) converters 261 are arranged in the horizontal direction. Each of the AD converters 261 includes a comparator 262 and a counter 263.

The $m^{th}$ AD converter 261 is connected to the vertical signal line 229-$m$ in a column m. In addition, a constant current source 255 is inserted between the vertical signal line 229-$m$ and a ground terminal.

The comparator 262 compares a pixel signal from the associated vertical signal line 229-$m$ with a ramp signal REF from the DAC 250. In one example, a sawtooth-shaped signal is supplied as the ramp signal REF. The comparator 262 supplies a result obtained by comparison to the counter 263.

The counter 263 counts a count value in synchronization with a clock signal CLK from the timing control unit 270 until the comparison result is inverted. The counter 263 outputs a digital signal indicating the count value to the image processing unit 290 as pixel data under the control of the column scanning circuit 280.

Configuration Example of Normal Pixel

Figure 5:
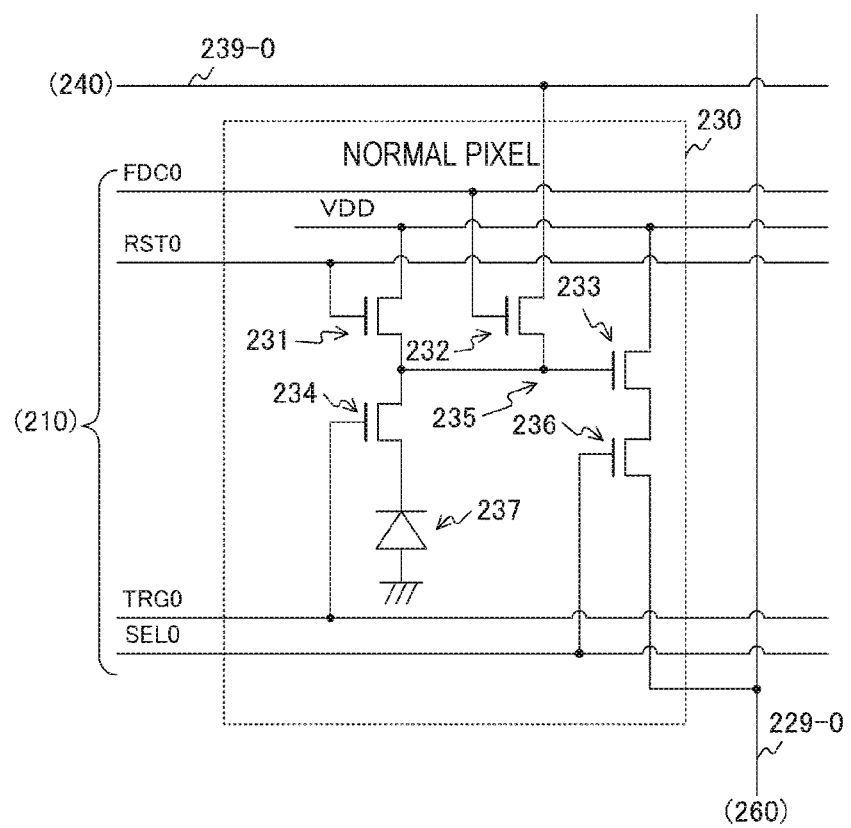
FIG. 5 is a circuit diagram depicting a configuration example of a normal pixel according to the first embodiment of the present technology.

FIG. 5 is a circuit diagram depicting a configuration example of the normal pixel 230 according to the first embodiment. The normal pixel 230 includes a reset transistor 231, a connection transistor 232, an amplification transistor 233, a transfer transistor 234, a floating diffusion layer 235, a selection transistor 236, and a photoelectric transducer 237.

The photoelectric transducer 237 photoelectrically converts incident light to generate electric charge. The transfer transistor 234 transfers electric charge from the photoelectric transducer 237 to the floating diffusion layer 235 in accordance with the transfer signal TRGn. The floating diffusion layer 235 accumulates electric charge and generates a voltage corresponding to the quantity of accumulated electric charge.

The reset transistor 231 initializes the quantity of electric charge of the floating diffusion layer 235 in accordance with the reset signal RSTn. The connection transistor 232 connects the floating diffusion layer 235 to the connection line 239-$m$ in accordance with the connection signal FDCn.

The amplification transistor 233 amplifies a signal corresponding to the voltage of the floating diffusion layer 235. The selection transistor 236 outputs a signal amplified by the amplification transistor 233 to the vertical signal line 229-$m$ as a pixel signal in accordance with the selection signals SELn.

Configuration Example of Light Shielding Pixel

Figure 6:
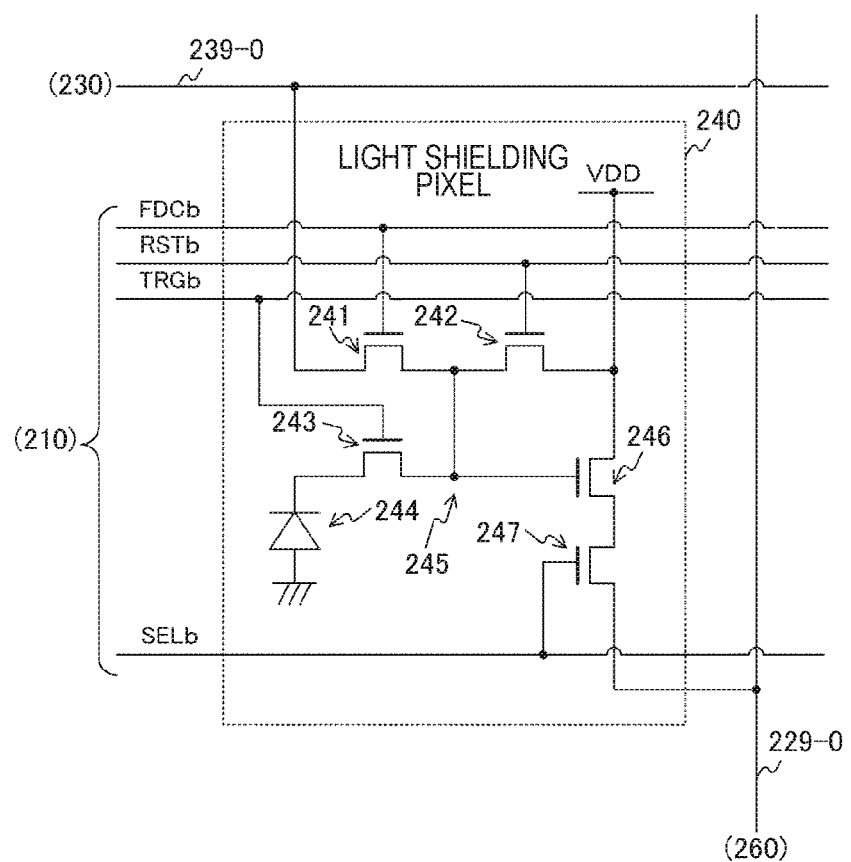
FIG. 6 is a circuit diagram depicting a configuration example of a light shielding pixel according to the first embodiment of the present technology.

FIG. 6 is a circuit diagram depicting a configuration example of the light shielding pixel 240 according to the first embodiment. The light shielding pixel 240 includes a connection transistor 241, a reset transistor 242, a transfer transistor 243, a photoelectric transducer 244, a floating diffusion layer 245, an amplification transistor 246, and a selection transistor 247. The connection configuration of these transistors is similar to that of the normal pixel 230. The light shielding pixel 240 is blocked from light, so the photoelectric transducer 244 and the transfer transistor 243 are unnecessary to be provided, but it is easier to manufacture the pixel array section 220 by making the layouts of the normal pixel 230 and the light shielding pixel 240 identical to each other, so they are provided.

Figure 7:
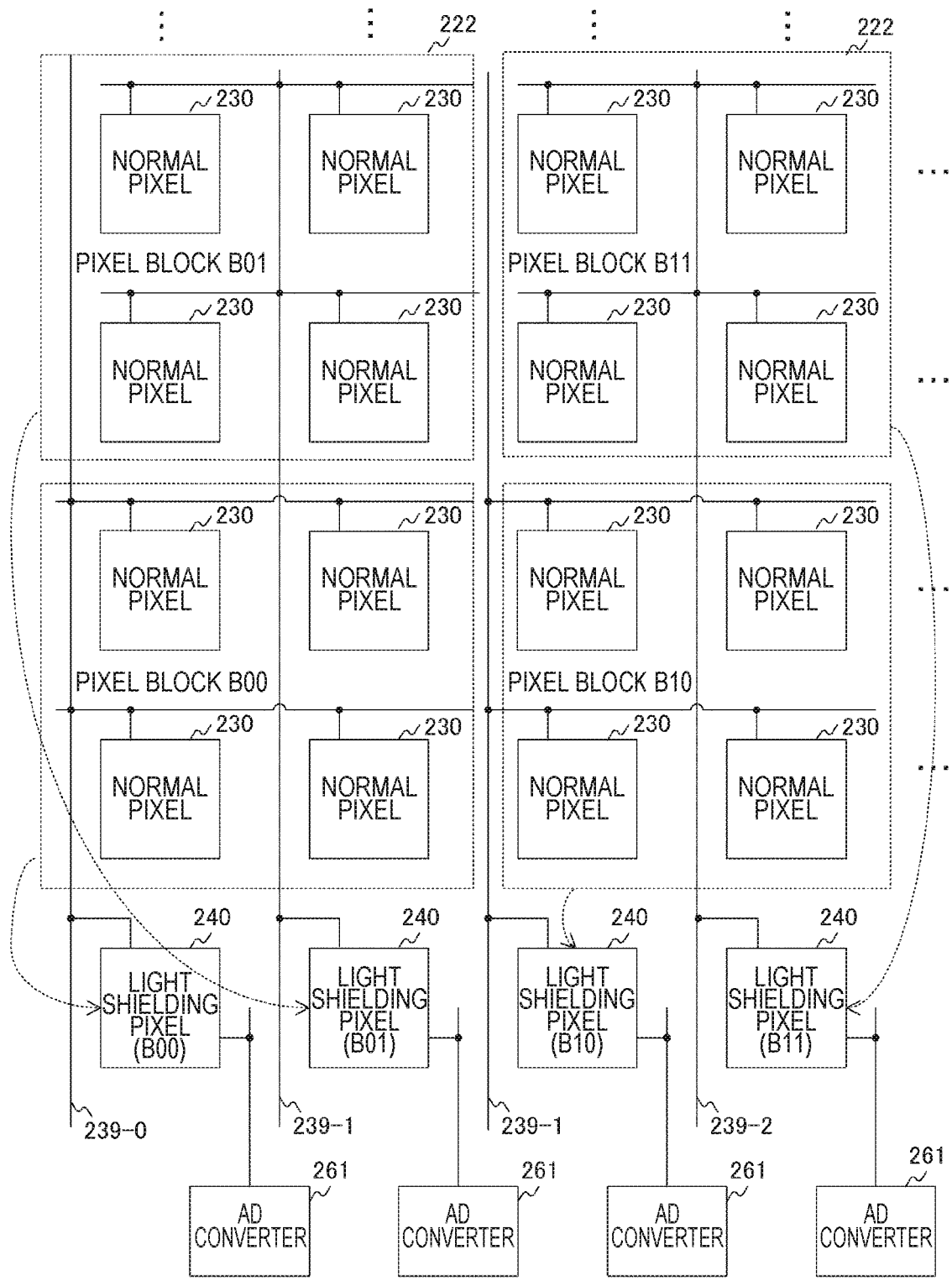
FIG. 7 is a diagram depicted to describe a pixel addition method according to the first embodiment of the present technology.

FIG. 7 is a diagram depicted to describe a pixel addition method according to the first embodiment. The light receiving area 221 is divided into a plurality of pixel blocks 222. Each of the pixel blocks 222 is provided with a predetermined number of lines including a plurality of pixels arranged in the horizontal direction. In one example, the normal pixels 230, each of which has an array of 2-by-2 (two rows and two columns) are arranged in each of the pixel blocks 222.

Further, the light shielding pixel 240 and the pixel block 222 are connected to each other via the connection line 239-*m* in one-to-one fashion. In addition, the number of light shielding pixels 240 is equal to or larger than the number of pixel blocks. In one example, the number of light shielding pixels 240 and the number of pixel blocks are both M.

In one example, a pixel block B00 at the bottom left is connected to the $0^{th}$ light shielding pixel 240. A pixel block B01 on the upper side of the pixel block B00 is connected to the $1^{st}$ light shielding pixel 240. In addition, a pixel block B10 on the right side of the pixel block B00 is connected to the $2^{nd}$ light shielding pixel 240, and a pixel block B11 on the right side of the pixel block B01 is connected to the $3^{rd}$ light shielding pixel 240.

The row scanning circuit 210 controls the respective pixel blocks 222 through the connection signals FDCn so that the pixel blocks 222 transfer electric charge to the associated light shielding pixels 240. In FIG. 7, the dotted arrows indicate a source and a destination of transfer of electric charge.

The respective quantities of electric charge of the normal pixels 230 in the pixel block 222 are added under the control of the row scanning circuit 210. The pixel signal corresponding to the added quantity of electric charge is read out from the light shielding pixel 240 of the transfer destination and is processed by the AD converter 261 in the column.

Here, a comparative example is assumed in which the quantities of electric charge are added and read out for each pixel block 222 without being transferred to the light shielding pixel 240. In this comparative example, the pixel addition of an array of 2-by-2 (two rows and two columns) reduces the number of rows to be read out to half as compared with the case of no addition. In one example, in a case where the number of rows N is 1440, the readout is necessary 720 times.

On the other hand, in the solid-state image pickup element 200 that performs the transfer to the light shielding pixel 240, the electric charge in the pixel block is transferred to the light shielding area 223 in one row, so the number of times of readout can be one time. In this way, the transfer to the light shielding pixel 240 makes it possible to reduce the number of times of readout as compared with the case of no transfer.

The reduction in the number of times of readout in this manner allows the power consumption of circuits around the signal processing unit 260 that performs AD conversion or the like to be reduced. In one example, it is possible to reduce the power consumption of the timing control unit 270 that supplies the clock signal to the signal processing unit 260 or the power consumption of the DAC 250 that supplies the ramp signal to the signal processing unit 260.

Furthermore, if the number of times of readout is reduced, the time it takes to perform the AD conversion (i.e., operating time) is shortened. In a case where a plurality of pieces of image data (frames) are read out consecutively at regular intervals, it is possible to reduce efficiently the power consumption by significantly reducing the operation time in the period for reading out one frame. Considering the recovery time of the operation of the sensor (the solid-state image pickup element 200), as the time it takes to perform the AD conversion is shortened, the rate of the non-operating time within one frame is increased, so the larger power reduction can be expected.

Figure 8:
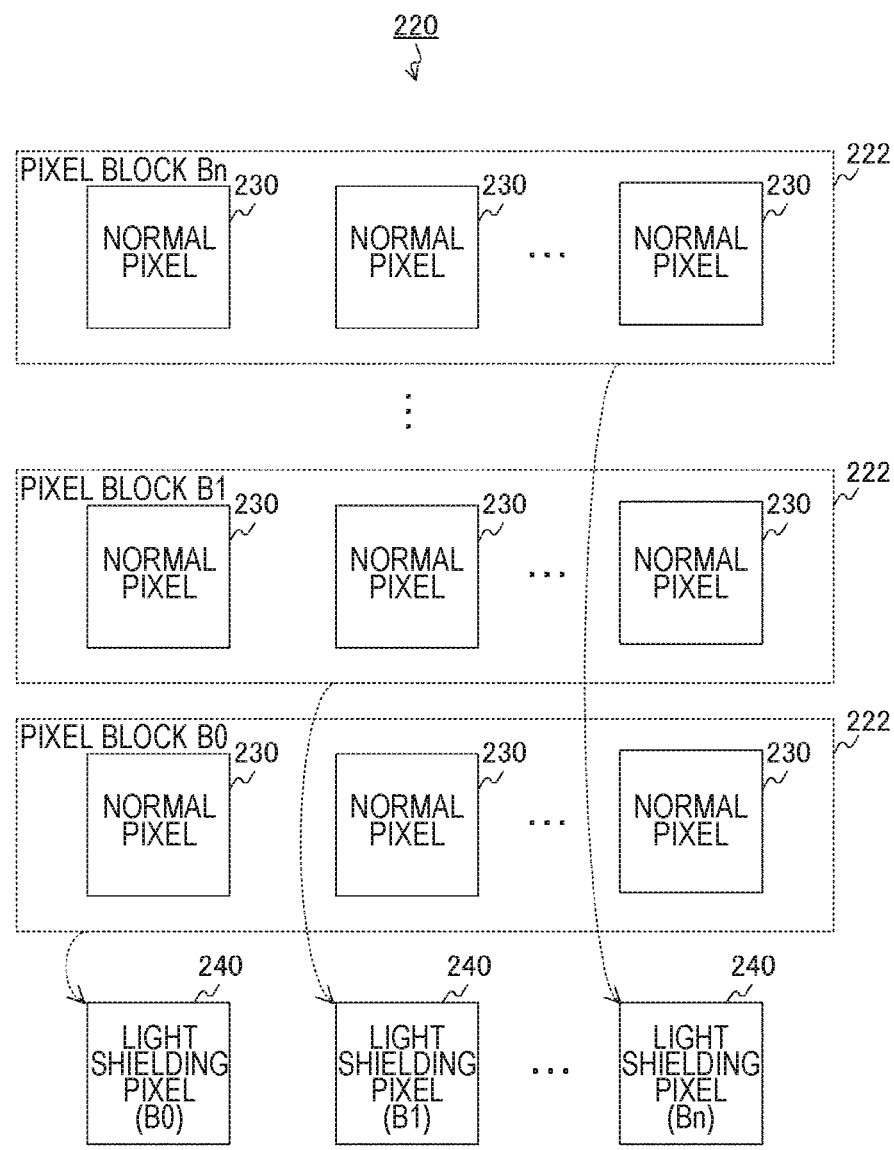
FIG. 8 is a diagram depicting an example of a layout of a pixel block according to the first embodiment of the present technology.

Moreover, although the number of rows of the light shielding pixels 240 is one, it can be two or more. In a case where the number of pixel blocks is larger than the number of columns, M, two or more rows of light shielding pixels 240 are provided. In addition, although the size of the pixel block 222 is set to an array of 2-by-2 (two rows and two columns), the number of rows or columns is not limited as long as it is two columns or more. In one example, the pixel addition can be performed using the pixel blocks 222, which each has pixels of 3-by-3 (three rows and three columns) array. In addition, as illustrated in FIG. 8, the entire row can be the pixel block 222.

Example of Operation of Solid-state Image Pickup Element

Figure 9:
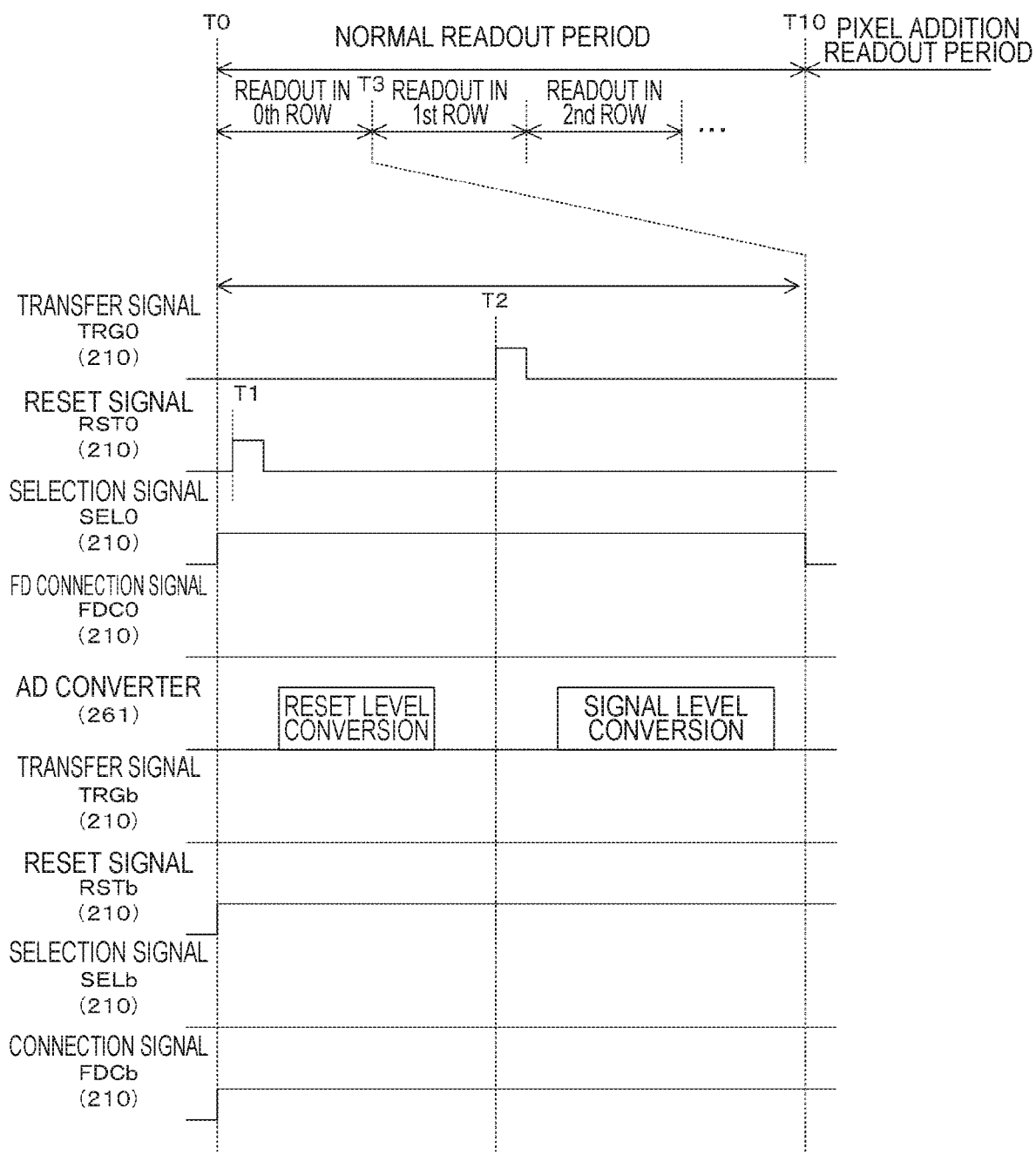
FIG. 9 is a timing chart showing an example of an operation of the solid-state image pickup element in a normal readout period according to the first embodiment of the present technology.

FIG. 9 is a timing chart showing an example of an operation of the solid-state image pickup element 200 in a normal readout period according to the first embodiment. This normal readout period is a period for reading out the pixel signal without performing the pixel addition.

At timing T0, the row scanning circuit 210 controls the selection signal SEL0, the reset signal RSTb, and the connection signal FDCb to be a high level. Then, at timing T1 after the timing T0, the row scanning circuit 210 controls the reset signal RST0 to be a high level over a predetermined pulse period. This allows the floating diffusion layer 235 in the $0^{th}$ row to be initialized and the potential of the connection line 239-*m* to be initialized.

At timing T2 after the timing T0, the row scanning circuit 210 controls the transfer signal TRG0 to be a high level over a predetermined pulse period. This control allows electric charge to be transferred to the floating diffusion layer 235 in the $0^{th}$ row. In addition, the row scanning circuit 210 controls the selection signal SEL0 to be a low level at timing T3 after the timing T2. This control allows the readout in the 0th row to be completed.

Further, the AD converter 261 in each column samples the level of the pixel signal as a reset level during the period from the timing T1 to the timing T2. Then, the AD converter 261 samples the level of the pixel signal as a signal level during the period from the timing T2 to the timing T3. The image processing unit 290 at the stage following the AD converter 261 performs correlated double sampling (CDS) processing for calculating a difference between the reset level and the signal level.

After the timing T3, the readout in the $1^{st}$ and subsequent rows is performed successively. The initialization and transfer in each row are started when a certain period of time is elapsed from the timing of initialization and transfer in the previous row. Such control is called a rolling shutter method.

Moreover, although the solid-state image pickup element 200 reads out all the pixels, a part of rows or columns can be thinned out and read out.

Figure 10:
FIG. 10 is a timing chart showing an example of an operation of the solid-state image pickup element in a pixel addition readout period according to the first embodiment of the present technology.

FIG. 10 is a timing chart showing an example of the operation of the solid-state image pickup element 200 in the pixel addition readout period according to the first embodiment. This pixel addition readout period is a period during which pixel signals are added and read out for each pixel block.

At timing T10, the row scanning circuit 210 controls the connection signals FDCn and FDCb and the selection signal SELb to be a high level. Then, at timing T11 after the timing T10, the row scanning circuit 210 controls the reset signals RSTn and RSTb to be a high level over a predetermined pulse period. This control allows the floating diffusion layers 235 of all the pixel blocks to be initialized. In addition, it is possible to prevent the potential of the connection line 239-$m$ from being subjected to floating and so initialization can be achieved.

Moreover, although the initialization is performed with the power supply in the light shielding pixel 240 as a countermeasure against floating, a method of performing the initialization with a power supply provided other than the light shielding pixel 240 is also conceivable. In addition, at the time of initialization, both the reset signals RSTn and RSTb are turned on and off, but only the reset signal RSTb can be turned on and off.

Then, at timing T12 after the timing T11, the row scanning circuit 210 controls the respective transfer signals TRGn to be a high level over the pulse period. This allows electric charge is transferred from all the pixel blocks to the light shielding area 223. As described above, the control of simultaneous transfer of electric charge in all the block rows is called a global shutter method.

Further, the row scanning circuit 210 controls the connection signals FDCn and FDCb and the selection signal SELb to be a low level at timing T13 after the timing T12. This control allows the readout of the addition signal to be completed.

Further, the AD converter 261 in each column samples the reset level during the period from the timing T11 to the timing T12, and samples the signal level during the period from the timing T12 to the timing T13. Moreover, although the solid-state image pickup element 200 reads out all the pixel blocks, a part of the block rows or the block columns can be thinned out and read out.

Figure 11:
FIG. 11 is a timing chart in which the period of a connection signal is shortened according to the first embodiment of the present technology.

Moreover, although the row scanning circuit 210 controls the connection signal FDCb to be a high level over the pixel addition readout period, the row scanning circuit 210 can control it to be a high level only during the period from each of the timing T11 and the timing T12 to the elapse of the pulse period, as shown in FIG. 11. In this figure, the pulse period of the connection signal FDCb is set to be longer than the pulse period of the transfer signal TRGn.

The wiring capacity of the connection line 239-$m$ is typically small, so the feedthrough occurs in controlling the reset signal, and the voltage of the floating diffusion layer is likely to be lower than the reset voltage. Here, when the connection line 239-$m$ is connected and the reset signal is turned on and off, the wiring capacity of the connection line 239-$m$ is large, the feedthrough is lowered negligibly, and there is a risk that the voltage range (output range) of the pixel signal varies. Thus, as illustrated in FIG. 11, the control of the connection signal FDCb to reproduce the feedthrough makes it possible to prevent the output range from varying.

Figure 12:
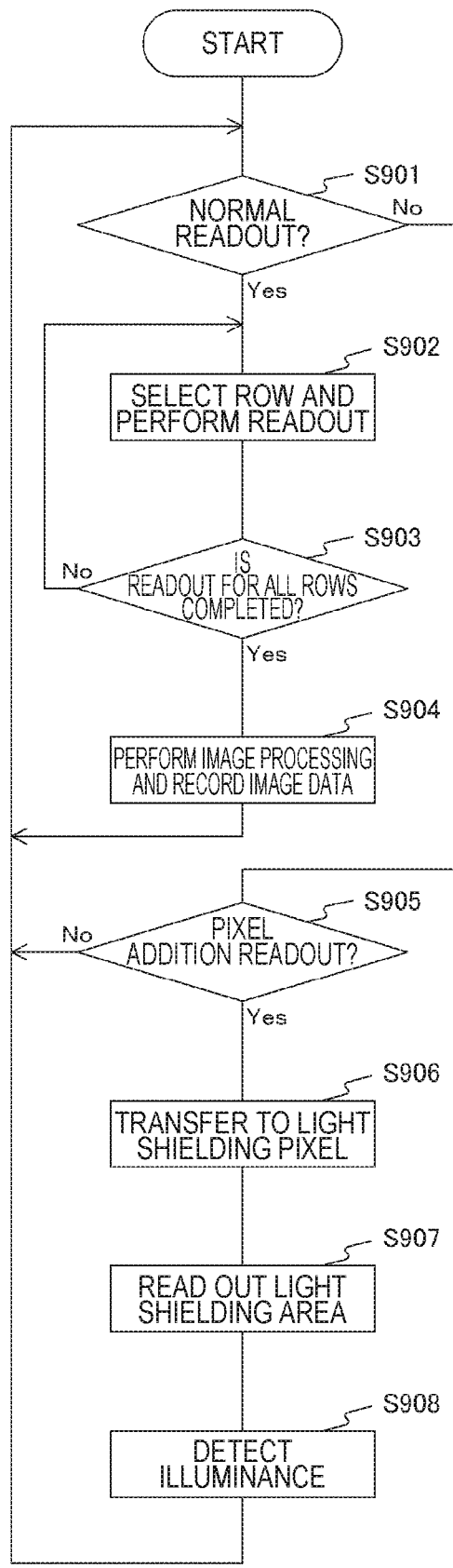
FIG. 12 is a flowchart showing an example of an operation of the solid-state image pickup element according to the first embodiment of the present technology.

FIG. 12 is a flowchart showing an example of the operation of the solid-state image pickup element 200 according to the first embodiment. This operation is started, in one example, when an operation for starting the image pickup of image data or measurement of illuminance is performed.

The solid-state image pickup element 200 first determines whether or not it is within the normal readout period (step S901). In a case where it is within the normal readout period (Yes in step S901), the solid-state image pickup element 200 selects a row to be read out and performs readout (step S902). Then, the solid-state image pickup element 200 determines whether or not the readout is completed for all the rows to be readout targets (step S903). In a case where the readout is not completed for all the rows (No in step S903), the solid-state image pickup element 200 repeatedly executes the processing of step S902 and subsequent steps.

In a case where the readout is completed for all the rows (Yes in step S903), the solid-state image pickup element 200 performs image processing on the image data and records it (step S904).

Further, in a case where it is not within the normal readout period (No in step S901), the solid-state image pickup element 200 determines whether or not it is within the pixel addition readout period (step S905). In a case where it is within the pixel addition readout period (Yes in step S905), the solid-state image pickup element 200 transfers the signal added to the light shielding pixel 240 (step S906), and reads out the pixel signal from the light shielding area (step S907). Then, the solid-state image pickup element 200 detects the illuminance on the basis of the image data created by the pixel addition (step S908).

In the case where it is not within the pixel addition readout period (No in step S905) or after step S908, the solid-state image pickup element 200 repeatedly executes step S901 and subsequent steps.

As described above, according to the first embodiment of the present technology, the arrangement of the light shielding pixels 240 in the row direction and the transfer of electric charge from the pixel block 222 to the associated light shielding pixels 240 make it possible to reduce the number of times of readout of signals subjected to the pixel addition in the pixel block 222. This makes it possible to reduce the power consumption of the solid-state image pickup element 200.

[Modification]

Although the solid-state image pickup element 200 detects the illuminance by the pixel addition in the first embodiment described above, it is possible to detect motion of a photographic subject instead of illumination detection. In order to detect motion of a photographic subject, in one example, the solid-state image pickup element 200 can execute processing of readout of the addition signal a plurality of times and obtaining a difference between the previous addition signal and the current addition signal. The solid-state image pickup element 200 according to the modification of the first embodiment is different from that of the first embodiment in that motion is detected by the pixel addition.

Figure 13:
FIG. 13 is a timing chart showing an example of an operation of a solid-state image pickup element in a pixel addition readout period according to a modification of the first embodiment of the present technology.

FIG. 13 is a timing chart showing an example of the operation of the solid-state image pickup element 200 in the pixel addition readout period according to the modification of the first embodiment. The solid-state image pickup element 200 according to the modification of the first embodiment controls the connection signal FDCb to be a low level by the timing T12 at the time of transfer of electric charge. In addition, during the period from the timing T11 to the timing T12, the reset level is read out, which is similar to the first embodiment.

Then, the row scanning circuit 210 controls the respective transfer signals TRGn to be a high level over a predetermined pulse period from the timing T12. In addition, the row scanning circuit 210 controls the connection signal FDCb to be a high level over a predetermined pulse period from the timing T11. The pulse period of the connection signal FDCb is set to be longer than the pulse period of the transfer signal TRGn. In addition, during the period from the timing T12 to the timing T13, the signal level is read out, which is similar to the first embodiment.

The readout control from the readout of the reset level to the readout of the signal level is executed a plurality of times, and the CDS processing for calculating the difference between them is executed every time the read control is performed. In the first readout control, the addition signal of the initial value is read out as the reset level, and the addition signal corresponding to the first exposure time is read out as the signal level. In the second and subsequent readout control, the previous signal level is read out again as the reset level, and the addition signal corresponding to the current exposure time is read out as the signal level. Then, the difference between the previous addition signal (reset level) and the current addition signal (signal level) is obtained by CDS processing. The image processing unit 290 detects an area in which the difference exceeds a predetermined threshold as a moving area.

Figure 14:
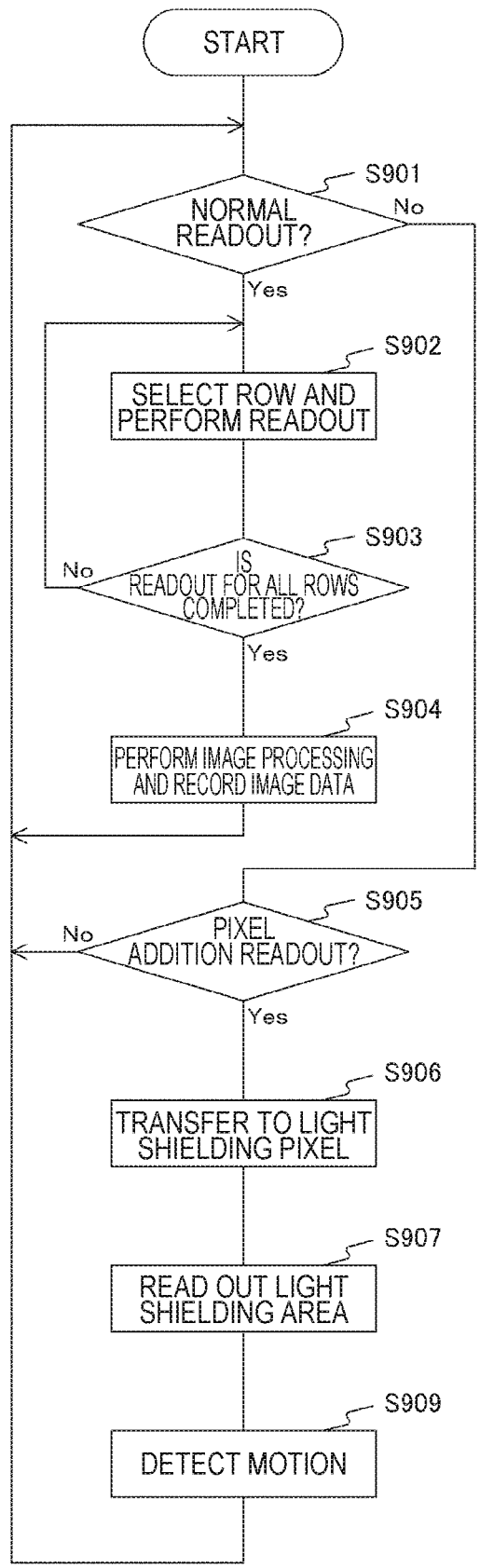
FIG. 14 is a flowchart illustrating an example of an operation of the solid-state image pickup element according to a modification of the first embodiment of the present technology.

FIG. 14 is a flowchart showing an example of the operation of the solid-state image pickup element 200 according to the modification of the first embodiment. The operation of the solid-state image pickup element 200 according to the modification of the first embodiment is different from that of the first embodiment in that motion detection (S909) is performed instead of the illumination detection (step S908).

The above-described solid-state image pickup element 200 is applicable not only to a camera such as the image pickup apparatus 100 but also to a sensor or the like for observing the environment, while taking advantage of the characteristics of low resolution, low power consumption, and global shutter operation. In this case, the solid-state image pickup element 200 is capable of detecting an action such as motion by the pixel addition with low power consumption, and then performing an operation to obtain a high-resolution image by the normal readout. If such a motion detection function is applied to a biological survey, the frequency of exchanging a battery can be lowered due to the feature that the power consumption is low. In addition, the solid-state image pickup element 200 can be employed for purposes of informing details when an action such as a landslide occurs or finding a natural disaster at an early stage by placing it in a forest or the like. The power consumption of the solid-state image pickup element 200 is low, so it can support maintenance-free for a long time with a battery or a solar panel. Thus, it is advantageous when an application using a large number of sensors is used.

Further, as an application of motion detection, it is possible to detect a high-speed object by utilizing the advantage that the frame rate can be increased considerably. The result of this detection is applicable to various purposes. In one example, the image pickup control unit 130 counts the number of running vehicles on the basis of the result of motion detection, and is capable of performing control to make transition to normal readout when the count value exceeds a fixed number. In addition, the image processing unit 290 or the like measures the speed of the vehicle from the result of motion detection, and the image pickup control unit 130 is also capable of making transition to the normal readout when the measured speed reaches or exceeds a fixed speed.

As described above, according to the modification of the first embodiment of the present technology, the control of sequentially reading out the previous addition signal and the current addition signal is executed a plurality of times and a difference between the previous and current addition signals is detected for each pixel block. Thus, it is possible to detect the motion of a photographic subject from the difference.

2. Second Embodiment

In the first embodiment described above, five transistors are provided for each normal pixel 230, but as the number of pixels increases, the circuit scale of the pixel array section 220 will increase. If the number of transistors provided for each normal pixel 230 decreases, it is possible to reduce the circuit scale. The solid-state image pickup element 200 according to a second embodiment is different from that of the first embodiment in that the circuit scale of the pixel array section 220 is reduced.

Figure 15:
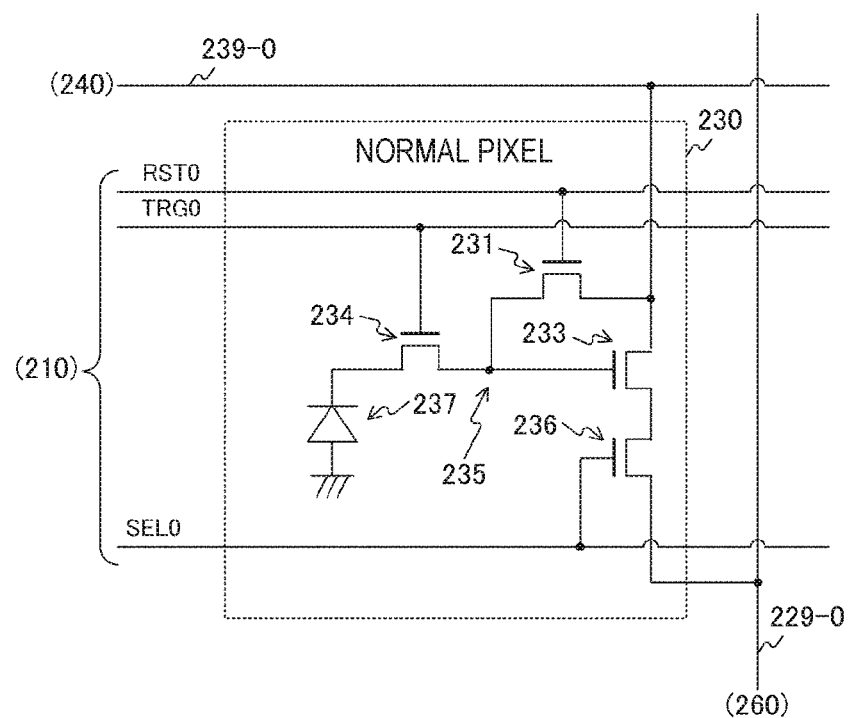
FIG. 15 is a circuit diagram depicting a configuration example of a normal pixel according to a second embodiment of the present technology.

FIG. 15 is a circuit diagram depicting a configuration example of the normal pixel 230 according to the second embodiment. The normal pixel 230 of the second embodiment is different from that of the first embodiment in that the connection transistor 232 is not provided. In addition, the reset transistor 231 of the second embodiment connects the floating diffusion layer 235 and the connection line 239-$m$ in accordance with the reset signal RST0. The control of the reset transistor 231 makes it possible not only to initialize the floating diffusion layer 235 like the first embodiment but also to connect the floating diffusion layer 235 to the connection line 239-$m$. This eliminates the connection transistor 232. Moreover, the reset transistor 231 is an example of the connection transistor set forth in the claims.

Figure 16:
FIG. 16 is a timing chart showing an example of an operation of a solid-state image pickup element in a pixel addition readout period according to the second embodiment of the present technology.

FIG. 16 is a timing chart showing an example of the operation of the solid-state image pickup element 200 in the pixel addition readout period according to the second embodiment.

At timing T10, the row scanning circuit 210 controls the reset signal RSTn, the connection signals FDCn and FDCb, and the selection signal SELb to be a high level. At timing T11 after the timing T10, the row scanning circuit 210 controls the reset signal RSTb to be a high level. This allows the floating diffusion layer 235 of the pixel block to be initialized and the potential of the connection line 239-$m$ to be initialized.

Then, at timing T12 after the timing T11, the row scanning circuit 210 controls the transfer signal TRGn to be a high level over the pulse period. This allows electric charge to be transferred from all the pixel blocks to the light shielding area 223.

Further, the row scanning circuit 210 controls the reset signal RSTn, the connection signals FDCn and FDCb, and the selection signal SELb to be a low level at timing T13 after the timing T12. This control allows the readout of the addition signal is completed.

Further, the AD converter 261 in each column samples the reset level during the period from the timing T11 to the timing T12, and samples the signal level during the period from the timing T12 to the timing T13.

As described above, according to the second embodiment of the present technology, the reset transistor 231 connects the floating diffusion layer 235 to the connection line 239-$m$, so it is unnecessary to provide the connection transistor 232. This makes it possible to reduce the circuit scale of the pixel array section 220.

3. Third Embodiment

In the first embodiment described above, the light shielding pixel 240 is also provided with the photoelectric transducer 244 and the transfer transistor 243 from the viewpoint of making the normal pixel 230 and the light shielding pixel 240 identical in configuration to each other to facilitate their manufacture. However, it is also possible for the light shielding pixel 240 not to be provided with the photoelectric transducer 244 and the transfer transistor 243 by giving priority to the reduction of the circuit scale. The solid-state image pickup element 200 according to a third embodiment is different from that of the first embodiment in that the circuit scale of the light shielding area 223 is reduced.

Figure 17:
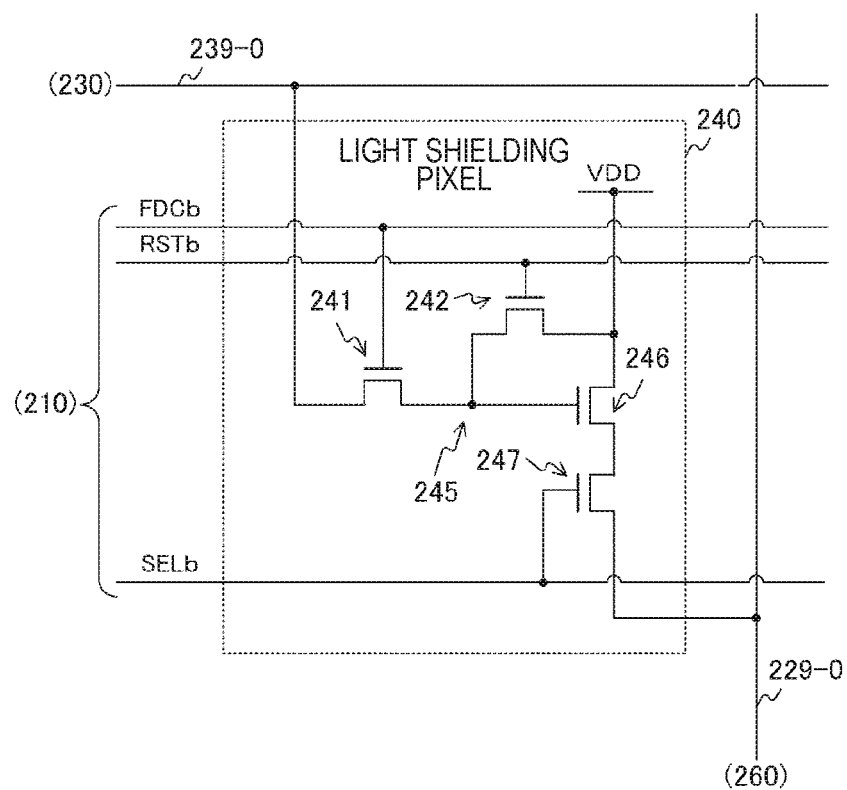
FIG. 17 is a circuit diagram depicting a configuration example of a light shielding pixel according to a third embodiment of the present technology.

FIG. 17 is a circuit diagram depicting a configuration example of the light shielding pixel 240 according to the third embodiment. The light shielding pixel 240 according to the third embodiment is different from that of the first embodiment in that it does not include the photoelectric transducer 244 and the transfer transistor 243.

As described above, according to the third embodiment of the present technology, the light shielding pixel 240 is not provided with the photoelectric transducer 244 and the transfer transistor 243, so it is possible to reduce the circuit scale of the light shielding area 223.

4. Fourth Embodiment

In the first embodiment described above, the connection transistor 232 in the normal pixel 230 connects the floating diffusion layer 235 to the connection line 239-m. However, during the period in which the connection transistor 232 is in off state, there is a risk that a leakage current flows from the floating diffusion layer 235 to the connection line 239-m. Although the leakage current per pixel is very small, as the number of pixels to be added increases, the total value of the leakage current increases, so the possibility that the readout value is affected increases. In order to prevent the influence of the leakage current from the floating diffusion layer 235, the photoelectric transducer 237, not the floating diffusion layer 235, can be necessary to be connected to the connection line 239-m. The solid-state image pickup element 200 according to the fourth embodiment is different from that of the first embodiment in that the photoelectric transducer 237 is connected to the connection line 239-m.

Figure 18:
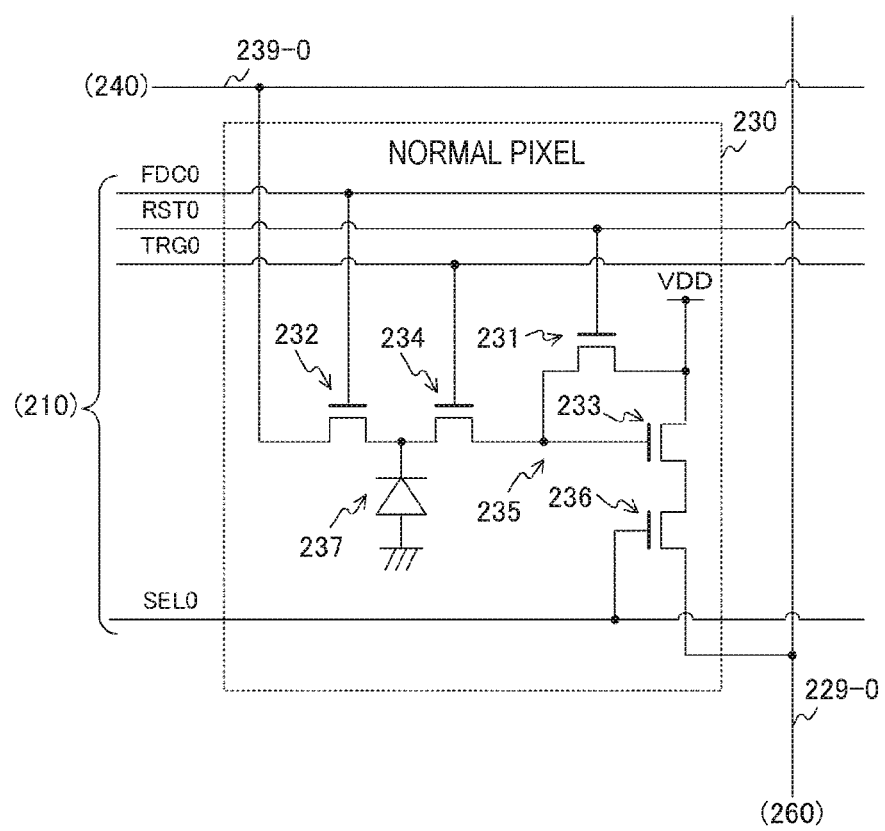
FIG. 18 is a circuit diagram depicting a configuration example of a normal pixel according to a fourth embodiment of the present technology.

FIG. 18 is a circuit diagram depicting a configuration example of the normal pixel 230 according to the fourth embodiment. The normal pixel 230 according to the fourth embodiment is different from that of the first embodiment in that the connection transistor 232 connects the photoelectric transducer 237 to the connection line 239-m in accordance with the connection signal FDCn.

Figure 19:
FIG. 19 is a timing chart showing an example of an operation of a solid-state image pickup element in a pixel addition readout period according to the fourth embodiment of the present technology.

FIG. 19 is a timing chart showing an example of the operation of the solid-state image pickup element 200 in the pixel addition readout period according to the fourth embodiment.

At timing T10, the row scanning circuit 210 controls the connection signal FDCn and the selection signal SELb to be a high level over a predetermined period. Then, at timing T11 after the timing T10, the row scanning circuit 210 controls the reset signal RSTb to be a high level over a certain period. This allows the floating diffusion layer 235 of all pixel blocks to be initialized. Here, the period in which the reset signal RSTb is at the high level is set to a sufficiently long time to complete the AD conversion of the reset level.

Then, at timing T12 after the timing T11, the row scanning circuit 210 controls the connection signal FDCb to be a high level. This allows electric charge to be transferred from all the pixel blocks to the light shielding area 223.

Further, the row scanning circuit 210 controls the connection signals FDCn and FDCb and the selection signal SELb to be a low level at timing T13 after the timing T12. This control allows the readout of the addition signal to be completed.

Further, the AD converter 261 in each column samples the reset level within the period in which the reset signal RSTb is at the high level, and samples the signal level during the period from the timing T11 to the timing T12.

Moreover, although the connection signal FDCb is controlled to be in the on state across the AD conversion period, it can be set to the off state before performing the AD conversion as illustrated in FIG. 11.

As described above, according to the fourth embodiment of the present technology, the photoelectric transducer 237 is connected to the connection line 239-m, so it is possible to prevent the influence of the leakage current from the floating diffusion layer 235.

5. Fifth Embodiment

In the first embodiment described above, the pixel signals are added for each pixel block 222, but the pixel blocks 222 are not connected to each other, so the respective addition signals of the plurality of pixel blocks 222 fail to be further added. The solid-state image pickup element 200 according to a fifth embodiment is different from that of the first embodiment in that the respective addition signals of the plurality of pixel blocks 222 are further added.

Figure 20:
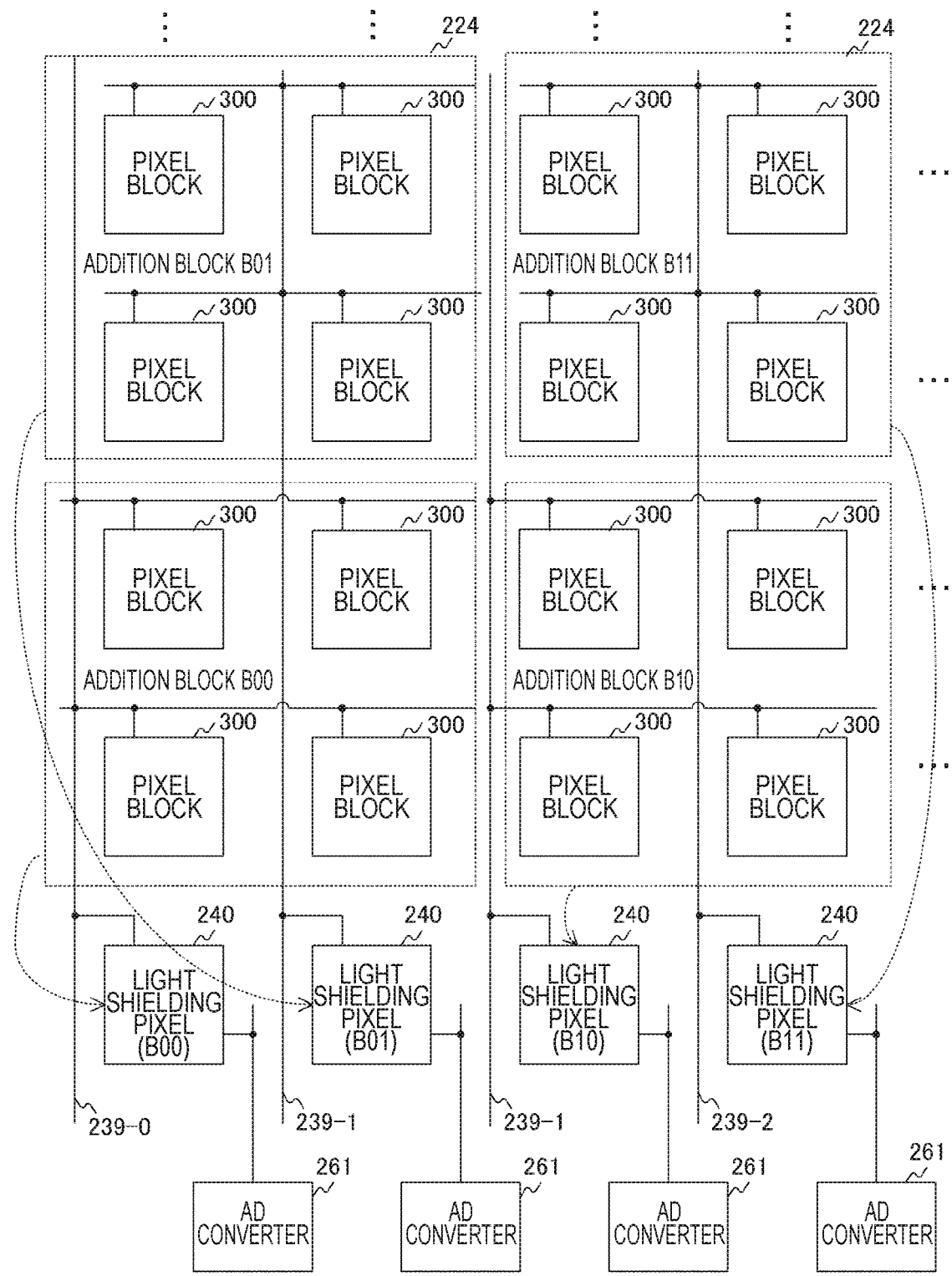
FIG. 20 is a plan view depicting a configuration example of a pixel array section and a signal processing unit according to a fifth embodiment of the present technology.

FIG. 20 is a plan view depicting a configuration example of the pixel array section 220 and the signal processing unit 260 according to the fifth embodiment. In the pixel array section 220 according to the fifth embodiment, a plurality of pixel blocks 300 are arranged in a two-dimensional grid pattern in the light receiving area 221. Each of the pixel blocks 300 has a plurality of (e.g., array of 4 rows and 2 columns) pixels arranged therein. A set of pixel blocks 300 arranged (in the horizontal direction or the like) is referred to as a "block row", and a set of pixel blocks 300 arranged in a direction perpendicular to the row is referred to as a "block column" hereinafter. The light shielding area 223 has a light shielding pixel 240 provided therein for each block column. In addition, the signal processing unit 260 is provided with an AD converter 261 for each block column.

Further, the light receiving area 221 is divided into a plurality of addition blocks 224. Each of the addition blocks 224 is provided with a pixel block 300 of two block columns or more (e.g., array of 2 rows and 2 columns). Each of the addition blocks 224 is connected to the light shielding pixel 240 in one-to-one fashion. In addition, the number of light shielding pixels 240 is equal to or larger than the number of addition blocks. In one example, the number of the light shielding pixels 240 and the number of the addition block 224 are both M.

The row scanning circuit 210 controls each of the addition blocks 224 so that the addition block 224 transfers electric charge to the associated light shielding pixel 240. In FIG. 20, the dotted arrows indicate a source and a destination of transfer of electric charge.

Figure 21:
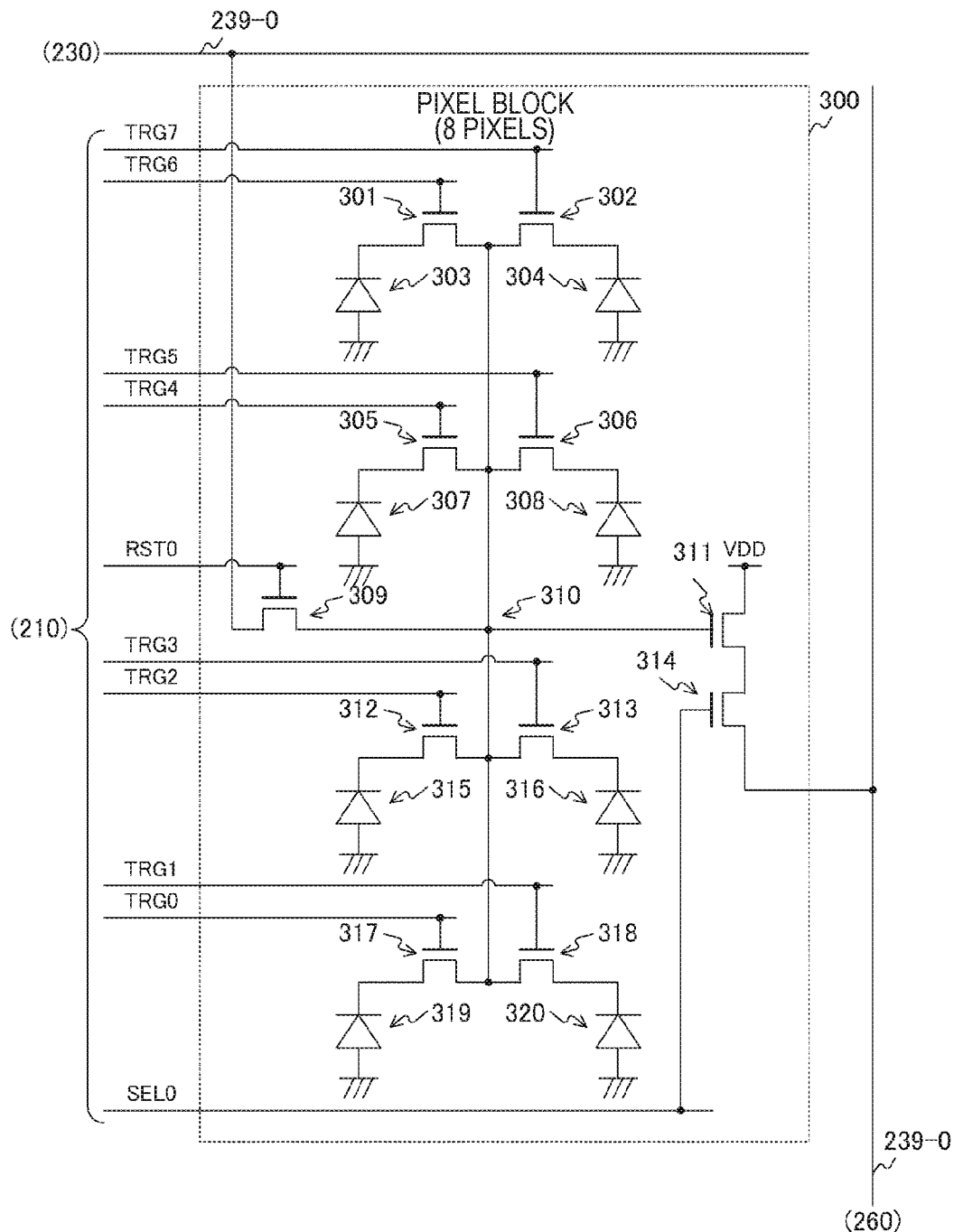
FIG. 21 is a circuit diagram depicting a configuration example of a pixel block according to the fifth embodiment of the present technology.

FIG. 21 is a circuit diagram depicting a configuration example of the pixel block 300 according to the fifth embodiment. The pixel block 300 includes photoelectric transducers 303, 304, 307, 308, 315, 316, 319, and 320 and transfer transistors 301, 302, 305, 306, 312, 313, 317, and 318. In addition, the pixel block 300 includes a reset transistor 309, a floating diffusion layer 310, an amplification transistor 311, and a selection transistor 314.

The transfer transistors 301, 302, 305, 306, 312, 313, 317, and 318 are respectively connected to different photoelectric transducers, and transfer electric charge from the associated photoelectric transducers to the floating diffusion layer 310. In addition, these transfer transistors are driven by the transfer signals TRGn0 to TRGn7, respectively. The reset transistor 309, the floating diffusion layer 310, the amplification transistor 311, and the selection transistor 314 are shared by eight pixels.

As described above, according to the fifth embodiment of the present technology, it is possible for the signals added in each of the pixel blocks 300 to be further added to transfer electric charge from the addition block 224 including the plurality of pixel blocks 300 to the associated light shielding pixels 240.

6. Sixth Embodiment

In the first embodiment described above, the respective floating diffusion layers of the normal pixels 230 are connected to the connection line 239-$m$ and four horizontal signal lines are wired for each row. However, as the number of rows increases, the number of wirings of the horizontal signal lines will increase. If the floating diffusion layers of two adjacent normal pixels 230 are connected to each other and one of them is connected to the connection line 239-$m$, it is possible to reduce the number of wirings of the horizontal signal line. The solid-state image pickup element 200 according to a sixth embodiment is different from that of the first embodiment in that the floating diffusion layers of two adjacent normal pixels 230 are connected to each other.

Figure 22:
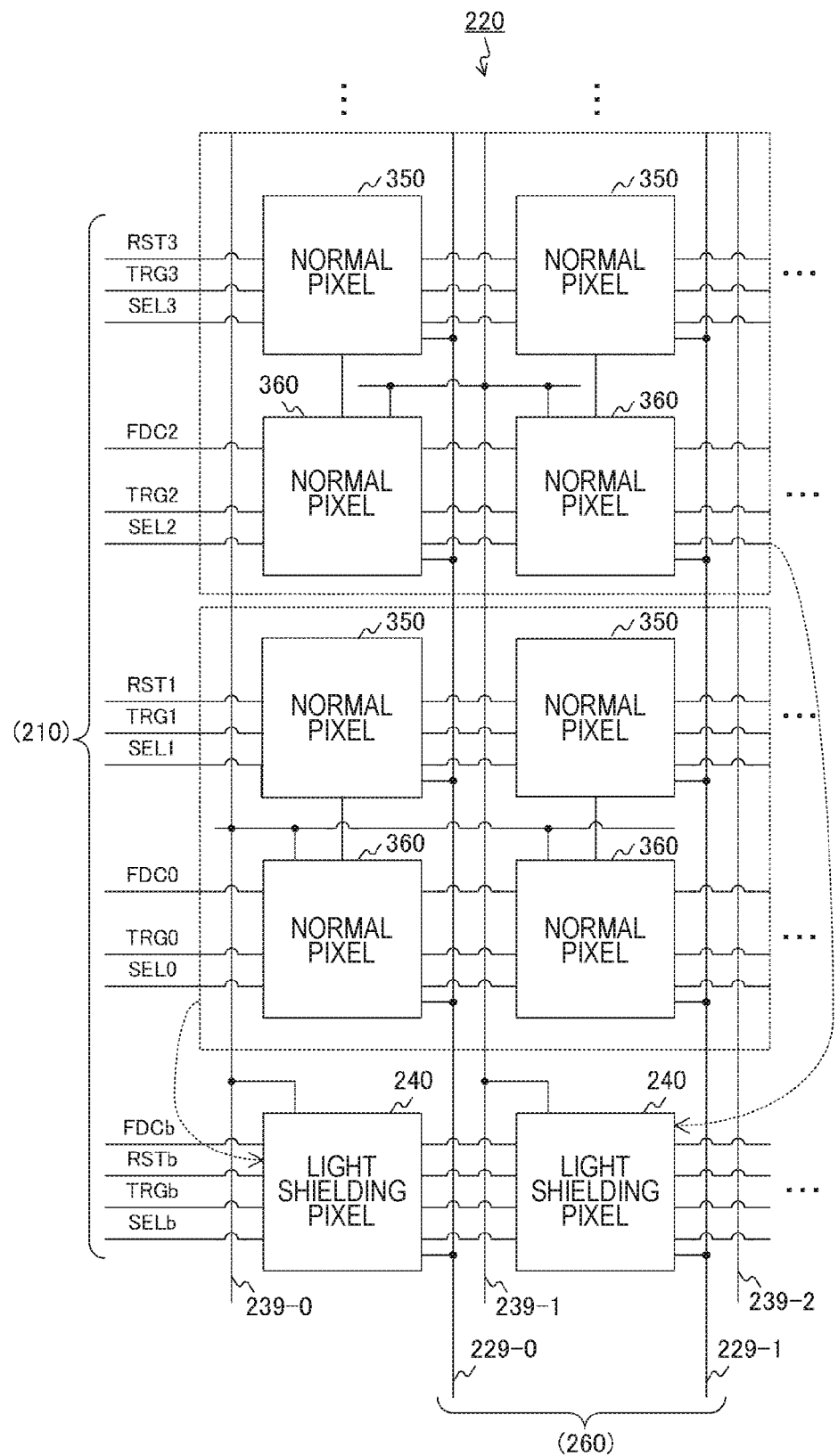
FIG. 22 is a plan view depicting a configuration example of a pixel array section according to a sixth embodiment of the present technology.

FIG. 22 is a plan view depicting a configuration example of the pixel array section 220 according to the sixth embodiment. In this fifth embodiment, the floating diffusion layers of a pair of adjacent normal pixels (350 and 360) in the vertical direction are connected to each other under the control of the connection signal FDCn. In addition, the floating diffusion layer of one of the pair of normal pixels (e.g., the normal pixel 360) is connected to the connection line 239-$m$.

Figure 23:
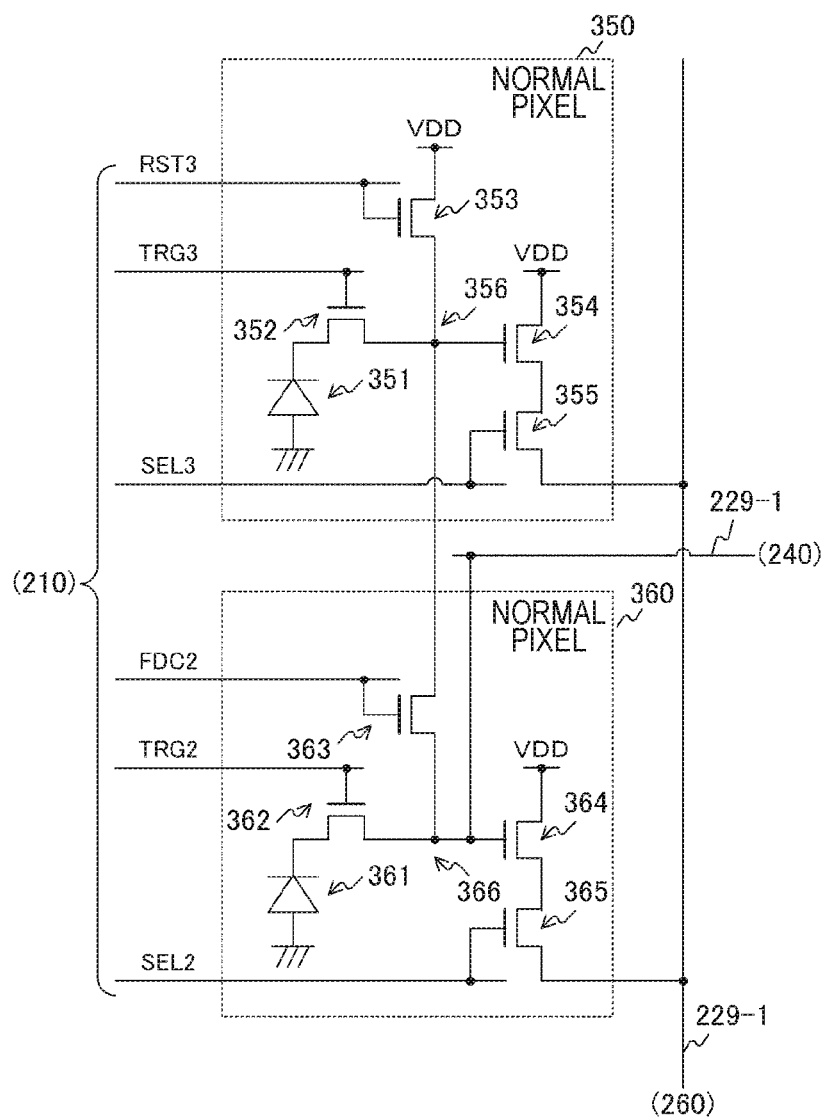
FIG. 23 is a circuit diagram depicting a configuration example of a normal pixel according to the sixth embodiment of the present technology.

FIG. 23 is a circuit diagram depicting a configuration example of the normal pixels 350 and 360 according to the sixth embodiment. The normal pixel 350 includes a photoelectric transducer 351, a transfer transistor 352, a reset transistor 353, an amplification transistor 354, a selection transistor 355, and a floating diffusion layer 356. In addition, the normal pixel 360 includes a photoelectric transducer 361, a transfer transistor 362, a connection transistor 363, an amplification transistor 364, a selection transistor 365, and a floating diffusion layer 366.

The transfer transistor 352 transfers electric charge from the photoelectric transducer 351 to the floating diffusion layer 356 in accordance with the transfer signal TRGn. The reset transistor 353 initializes the floating diffusion layer 356 in accordance with the reset signal RSTn.

Further, the transfer transistor 362 transfers electric charge from the photoelectric transducer 361 to the floating diffusion layer 366 in accordance with the transfer signal TRGn. The connection transistor 363 connects the floating diffusion layers 356 and 366 in accordance with the connection signal FDCn to allow electric charge to be transferred from the normal pixel 350 to the normal pixel 360. The floating diffusion layer 366 is also connected to the connection line 239-$m$. The row scanning circuit 210 controls both the reset transistor 353 and the connection transistor 363 so that they are to be turned on in initializing the floating diffusion layers 356 and 366.

The configuration described above allows the reset transistor 353 and the connection transistor 363 to be shared respectively by the normal pixels 350 and 360, so it is sufficient that any one of the horizontal signal line that transmits the reset signal RSTn and the horizontal signal line that transmits the connection signal FDCn can be wired every two rows. Thus, it is possible to reduce the number of horizontal signal lines as compared with the first embodiment in which one line is wired per row.

As described above, according to the sixth embodiment of the present technology, the reset transistor 353 and the connection transistor 363 are shared respectively by the normal pixels 350 and 360. Thus, it is possible to reduce the number of wirings of the horizontal signal line for transmitting a signal used to control these transistors.

FIRST APPLICATION EXAMPLE

The technology according to the present disclosure can be applied to various products. For example, the technology according to the present disclosure may be applied to an endoscopic surgical system.

Figure 24:
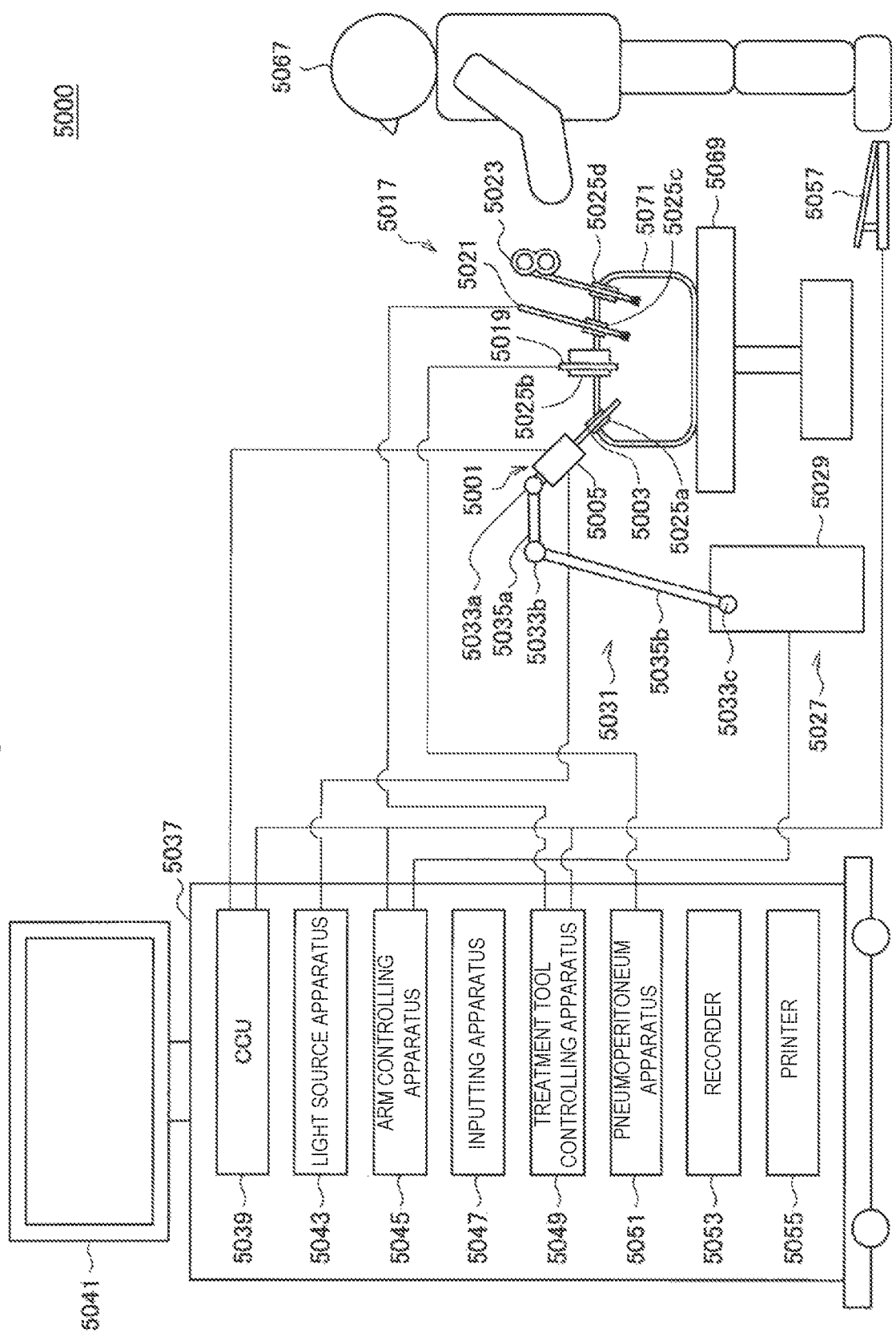
FIG. 24 is a view depicting an example of a schematic configuration of an endoscopic surgery system.

FIG. 24 is a view depicting an example of a schematic configuration of an endoscopic surgery system 5000 to which the technology according to an embodiment of the present disclosure can be applied. In FIG. 24, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body cavity of the patient 5071 through the trocars 5025a to 5025d. In the example depicted, as the other surgical tools 5017, a pneumoperitoneum tube 5019, an energy device 5021 and forceps 5023 are inserted into body cavity of the patient 5071. Further, the energy device 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, tweezers or a retractor may be used.

An image of a surgical region in a body cavity of the patient 5071 imaged by the endoscope 5001 is displayed on a display apparatus 5041. The surgeon 5067 would use the energy device 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy device 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body cavity of the patient 5071, and a camera head 5005 connected to a proximal end of the lens barrel 5003. In the example depicted, the endoscope 5001 is depicted as a rigid endoscope having the lens barrel 5003 of the hard type. However, the endoscope 5001 may otherwise be configured as a flexible endoscope having the lens barrel 5003 of the flexible type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body cavity of the patient 5071 through the objective lens. It is to be noted that the endoscope 5001 may be a forward-viewing endoscope or may be an oblique-viewing endoscope or a side-viewing endoscope.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy device 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy device 5021 for cautery or incision of a tissue, sealing of a blood vessel or the like. A pneumoperitoneum apparatus 5051 feeds gas into a body cavity of the patient 5071 through the pneumoperitoneum tube 5019 to inflate the body cavity in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033a, 5033b and 5033c and the plurality of links 5035a and 5035b connected to each other by the joint portion 5033b. In FIG. 24, for simplified illustration, the configuration of the arm unit 5031 is depicted in a simplified form. Actually, the shape, number and arrangement of the joint portions 5033a to 5033c and the links 5035a and 5035b and the direction and so forth of axes of rotation of the joint portions 5033a to 5033c can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body cavity of the patient 5071.

An actuator is provided in each of the joint portions 5033a to 5033c, and the joint portions 5033a to 5033c are configured such that they are rotatable around predetermined axes of rotation thereof by driving of the respective actuators. The driving of the actuators is controlled by the arm controlling apparatus 5045 to control the rotational angle of each of the joint portions 5033a to 5033c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endo scope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the operating room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower wavelength band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrow-band light and/or excitation light suitable for special light observation as described above.

(Camera Head and CCU)

Figure 25:
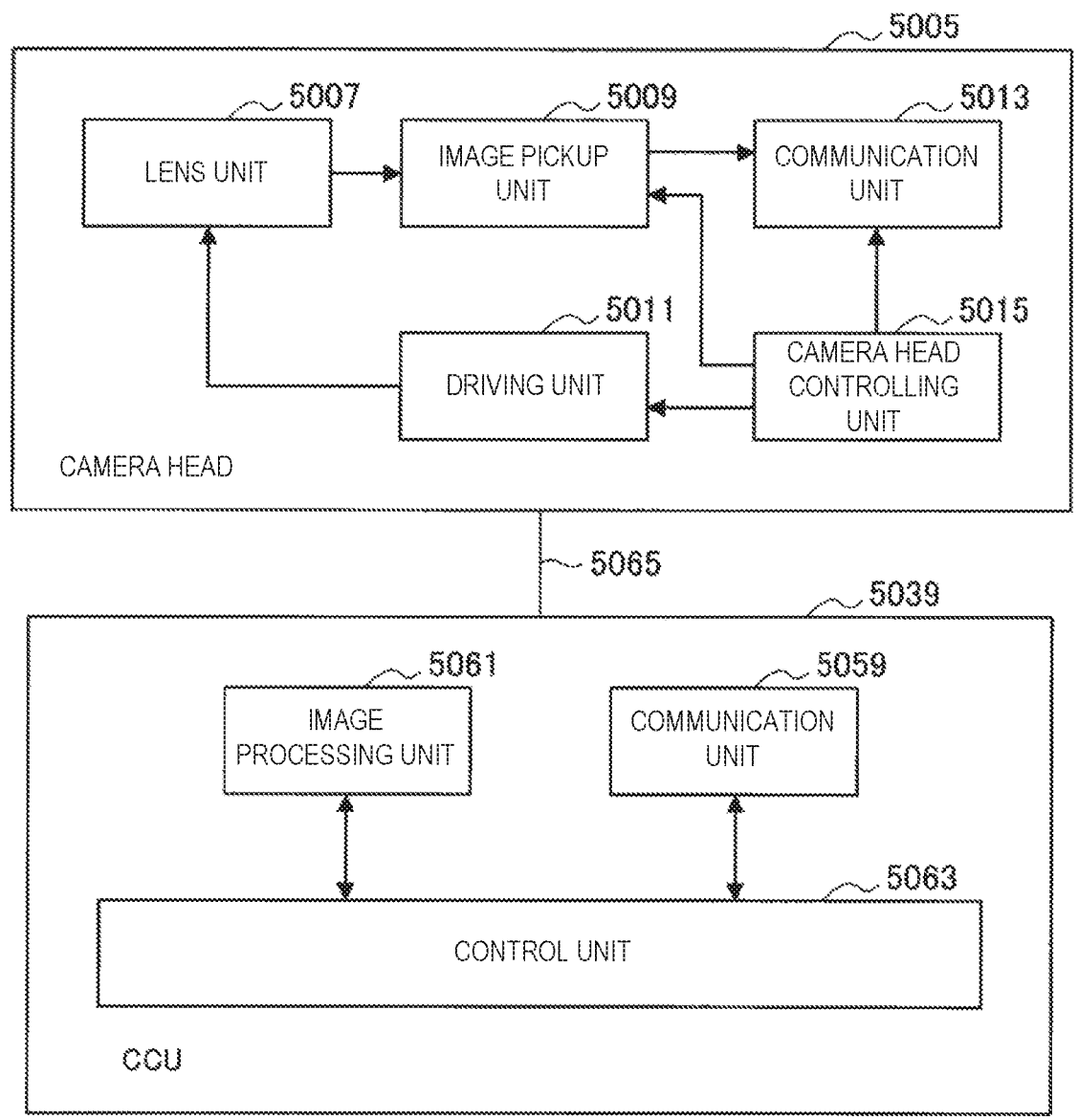
FIG. 25 is a block diagram depicting an example of a functional configuration of a camera head and a camera control unit (CCU) depicted in FIG. 24.

Functions of the camera head 5005 of the endoscope 5001 and the CCU 5039 are described in more detail with reference to FIG. 25. FIG. 25 is a block diagram depicting an example of a functional configuration of the camera head 5005 and the CCU 5039 depicted in FIG. 24.

Referring to FIG. 25, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy device 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the operating room. Therefore, such a situation that movement of medical staff in the operating room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a flexible endoscopic system for inspection or a microscopic surgery system.

The technology of the present disclosure is suitably applicable to the camera head 5005 illustrated in FIG. 25 among the above-described configurations. Specifically, the solid-state image pickup element 200 illustrated in FIG. 2 is used for the image pickup unit 5009 in the camera head 5005. The application of the solid-state image pickup element 200 reduces the number of times of readout at the time of pixel addition, so it is possible to reduce the power consumption of the endoscopic surgery system 5000.

SECOND APPLICATION EXAMPLE

The technology according to the present disclosure can be applied to various products. For example, the technology according to the present disclosure may be applied to a surgery room system.

Figure 26:
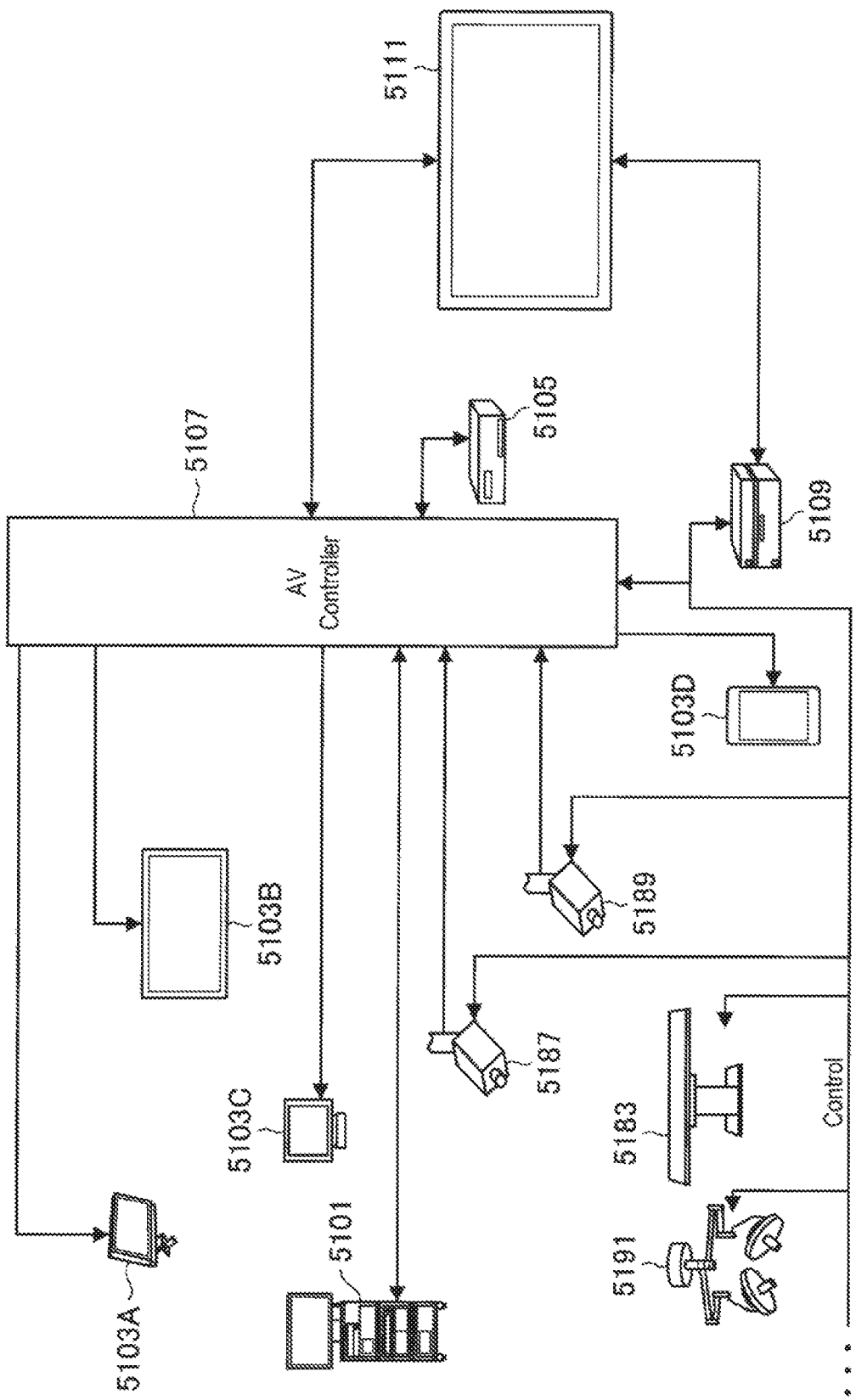
FIG. 26 is a view schematically depicting a general configuration of a surgery room system.

FIG. 26 is a view schematically depicting a general configuration of an operating room system 5100 to which the technology according to an embodiment of the present disclosure can be applied. Referring to FIG. 26, the operating room system 5100 is configured such that a group of apparatus installed in an operating room are connected for cooperation with each other through an audiovisual (AV) controller 5107 and an operating room controlling apparatus 5109.

In the operating room, various apparatus may be installed. In FIG. 26, as an example, various apparatus group 5101 for endoscopic surgery, a ceiling camera 5187, a surgery field camera 5189, a plurality of display apparatus 5103A to 5103D, a recorder 5105, a patient bed 5183 and an illumination 5191 are depicted. The ceiling camera 5187 is provided on the ceiling of an operating room and images the hands of a surgeon. The surgery field camera 5189 is provided on the ceiling of the operating room and images a state of the entire operating room.

Among the apparatus mentioned, the apparatus group 5101 belongs to an endoscopic surgery system 5113 hereinafter described and include an endoscope, a display apparatus which displays an image picked up by the endoscope and so forth. Various apparatus belonging to the endoscopic surgery system 5113 are referred to also as medical equipment. Meanwhile, the display apparatus 5103A to 5103D, the recorder 5105, the patient bed 5183 and the illumination 5191 are apparatus which are equipped, for example, in the operating room separately from the endoscopic surgery system 5113. The apparatus which do not belong to the endoscopic surgery system 5113 are referred to also as non-medical equipment. The audiovisual controller 5107 and/or the operating room controlling apparatus 5109 cooperatively control operation of the medical equipment and the non-medical equipment with each other.

The audiovisual controller 5107 integrally controls processes of the medical equipment and the non-medical equipment relating to image display. Specifically, each of the apparatus group 5101, the ceiling camera 5187 and the surgery field camera 5189 from among the apparatus provided in the operating room system 5100 may be an apparatus having a function of sending information to be displayed during surgery (such information is hereinafter referred to as display information, and the apparatus mentioned is hereinafter referred to as apparatus of a sending source). Meanwhile, each of the display apparatus 5103A to 5103D may be an apparatus to which display information is outputted (the apparatus is hereinafter referred to also as apparatus of an output destination). Further, the recorder 5105 may be an apparatus which serves as both of an apparatus of a sending source and an apparatus of an output destination. The audiovisual controller 5107 has a function of controlling operation of an apparatus of a sending source and an apparatus of an output destination to acquire display information from the apparatus of a sending source and transmit the display information to the apparatus of an output destination so as to be displayed or recorded. It is to be noted that the display information includes various images picked up during surgery, various kinds of information relating to the surgery (for example, physical information of a patient, inspection results in the past or information regarding a surgical procedure) and so forth.

Specifically, to the audiovisual controller 5107, information relating to an image of a surgical region in a body cavity of a patient imaged by the endoscope may be transmitted as the display information from the apparatus group 5101. Further, from the ceiling camera 5187, information relating to an image of the hands of the surgeon picked up by the ceiling camera 5187 may be transmitted as display information. Further, from the surgery field camera 5189, information relating to an image picked up by the surgery field camera 5189 and illustrating a state of the entire operating room may be transmitted as display information. It is to be noted that, if a different apparatus having an image pickup function exists in the operating room system 5100, then the audiovisual controller 5107 may acquire information relating to an image picked up by the different apparatus as display information also from the different apparatus.

Alternatively, for example, in the recorder 5105, information relating to such images as mentioned above picked up in the past is recorded by the audiovisual controller 5107. The audiovisual controller 5107 can acquire, as display information, information relating to the images picked up in the past from the recorder 5105. It is to be noted that also various pieces of information relating to surgery may be recorded in advance in the recorder 5105.

The audiovisual controller 5107 controls at least one of the display apparatus 5103A to 5103D, which are apparatus of an output destination, to display acquired display information (namely, images picked up during surgery or various pieces of information relating to the surgery). In the example depicted, the display apparatus 5103A is a display apparatus installed so as to be suspended from the ceiling of the operating room; the display apparatus 5103B is a display apparatus installed on a wall face of the operating room; the display apparatus 5103C is a display apparatus installed on a desk in the operating room; and the display apparatus 5103D is a mobile apparatus (for example, a tablet personal computer (PC)) having a display function.

Further, though not depicted in FIG. 26, the operating room system 5100 may include an apparatus outside the operating room. The apparatus outside the operating room may be, for example, a server connected to a network constructed inside and outside the hospital, a PC used by medical staff, a projector installed in a meeting room of the hospital or the like. Where such an external apparatus is located outside the hospital, also it is possible for the audiovisual controller 5107 to cause display information to be displayed on a display apparatus of a different hospital through a teleconferencing system or the like to perform telemedicine.

The operating room controlling apparatus 5109 integrally controls processes other than processes relating to image display on the non-medical equipment. For example, the operating room controlling apparatus 5109 controls driving of the patient bed 5183, the ceiling camera 5187, the surgery field camera 5189 and the illumination 5191.

In the operating room system 5100, a centralized operation panel 5111 is provided such that it is possible to issue an instruction regarding image display to the audiovisual controller 5107 or issue an instruction regarding operation of the non-medical equipment to the operating room controlling apparatus 5109 through the centralized operation panel 5111. The centralized operation panel 5111 is configured by providing a touch panel on a display face of a display apparatus.

Figure 27:
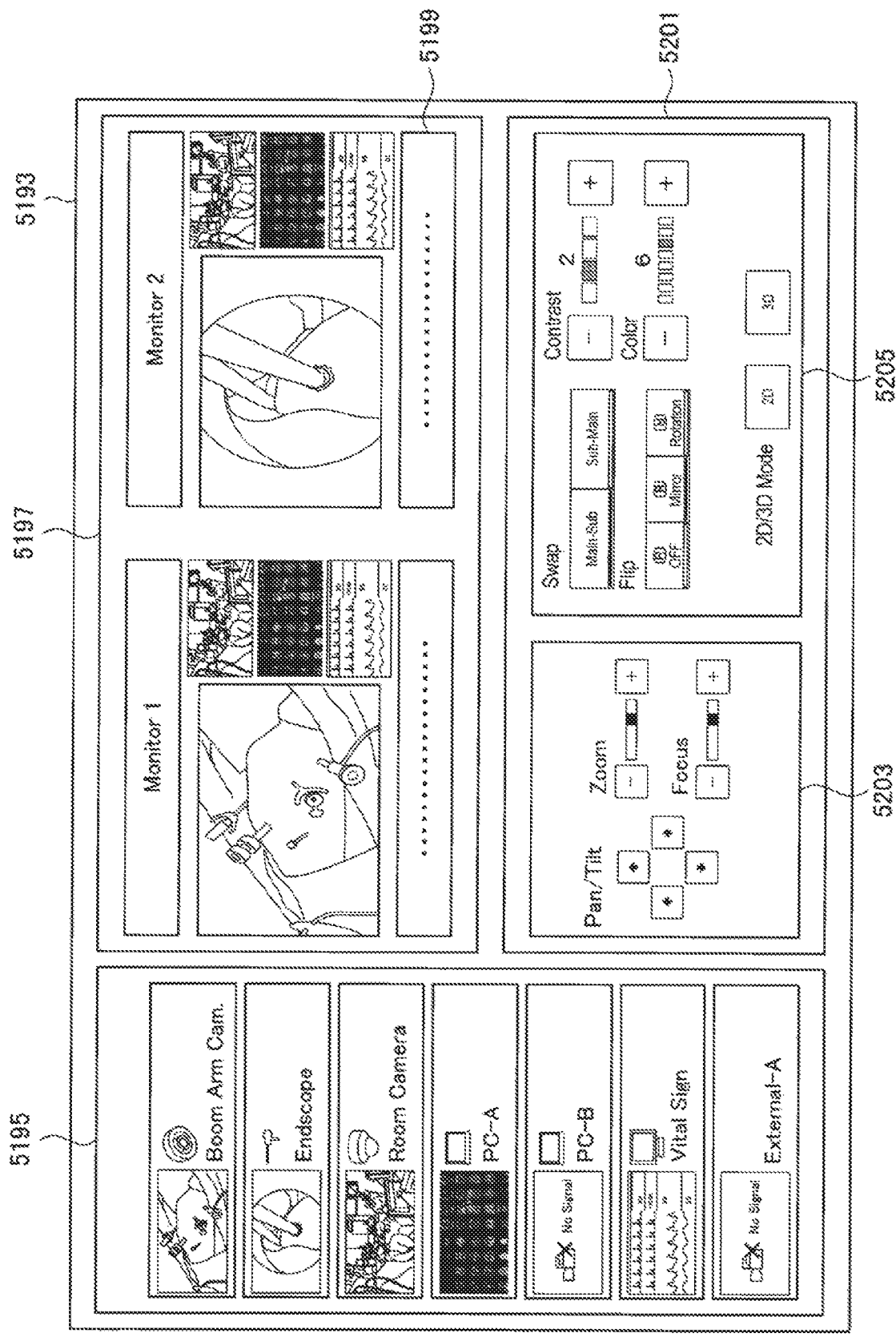
FIG. 27 is a view depicting an example of display of an operation screen image of a centralized operation panel.

FIG. 27 is a view depicting an example of display of an operation screen image on the centralized operation panel 5111. In FIG. 27, as an example, an operation screen image is depicted which corresponds to a case in which two display apparatus are provided as apparatus of an output destination in the operating room system 5100. Referring to FIG. 27, the operation screen image 5193 includes a sending source selection region 5195, a preview region 5197 and a control region 5201.

In the sending source selection region 5195, the sending source apparatus provided in the operating room system 5100 and thumbnail screen images representative of display information the sending source apparatus have are displayed in an associated manner with each other. A user can select display information to be displayed on the display apparatus from any of the sending source apparatus displayed in the sending source selection region 5195.

In the preview region 5197, a preview of screen images displayed on two display apparatus (Monitor 1 and Monitor 2) which are apparatus of an output destination is displayed. In the example depicted, four images are displayed by picture in picture (PinP) display in regard to one display apparatus. The four images correspond to display information sent from the sending source apparatus selected in the sending source selection region 5195. One of the four images is displayed in a comparatively large size as a main image while the remaining three images are displayed in a comparatively small size as sub images. The user can exchange between the main image and the sub images by suitably selecting one of the images from among the four images displayed in the region. Further, a status displaying region 5199 is provided below the region in which the four images are displayed, and a status relating to surgery (for example, elapsed time of the surgery, physical information of the patient and so forth) may be displayed suitably in the status displaying region 5199.

A sending source operation region 5203 and an output destination operation region 5205 are provided in the control region 5201. In the sending source operation region 5203, a graphical user interface (GUI) part for performing an operation for an apparatus of a sending source is displayed. In the output destination operation region 5205, a GUI part for performing an operation for an apparatus of an output destination is displayed. In the example depicted, GUI parts for performing various operations for a camera (panning, tilting and zooming) in an apparatus of a sending source having an image pickup function are provided in the sending source operation region 5203. The user can control operation of the camera of an apparatus of a sending source by suitably selecting any of the GUI parts. It is to be noted that, though not depicted, where the apparatus of a sending source selected in the sending source selection region 5195 is a recorder (namely, where an image recorded in the recorder in the past is displayed in the preview region 5197), GUI parts for performing such operations as reproduction of the image, stopping of reproduction, rewinding, fast-feeding and so forth may be provided in the sending source operation region 5203.

Further, in the output destination operation region 5205, GUI parts for performing various operations for display on a display apparatus which is an apparatus of an output destination (swap, flip, color adjustment, contrast adjustment and switching between two dimensional (2D) display and three dimensional (3D) display) are provided. The user can operate the display of the display apparatus by suitably selecting any of the GUI parts.

It is to be noted that the operation screen image to be displayed on the centralized operation panel 5111 is not limited to the depicted example, and the user may be able to perform operation inputting to each apparatus which can be controlled by the audiovisual controller 5107 and the operating room controlling apparatus 5109 provided in the operating room system 5100 through the centralized operation panel 5111.

Figure 28:
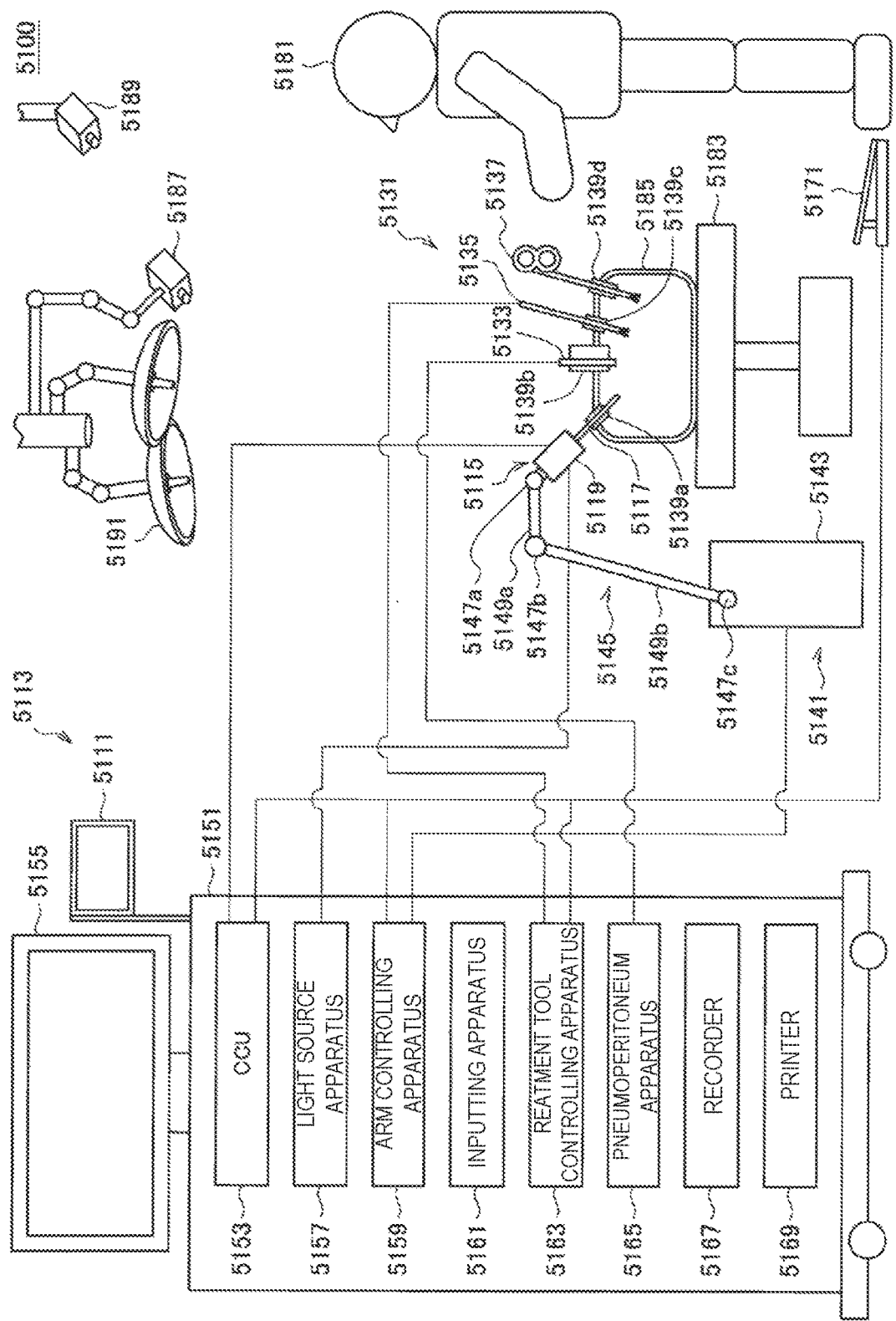
FIG. 28 is a view illustrating an example of a state of surgery to which the surgery room system is applied.

FIG. 28 is a view illustrating an example of a state of surgery to which the operating room system described above is applied. The ceiling camera 5187 and the surgery field camera 5189 are provided on the ceiling of the operating room such that it can image the hands of a surgeon (medical doctor) 5181 who performs treatment for an affected area of a patient 5185 on the patient bed 5183 and the entire operating room. The ceiling camera 5187 and the surgery field camera 5189 may include a magnification adjustment function, a focal distance adjustment function, an imaging direction adjustment function and so forth. The illumination 5191 is provided on the ceiling of the operating room and irradiates at least upon the hands of the surgeon 5181. The illumination 5191 may be configured such that the irradiation light amount, the wavelength (color) of the irradiation light, the irradiation direction of the light and so forth can be adjusted suitably.

The endoscopic surgery system 5113, the patient bed 5183, the ceiling camera 5187, the surgery field camera 5189 and the illumination 5191 are connected for cooperation with each other through the audiovisual controller 5107 and the operating room controlling apparatus 5109 (not depicted in FIG. 28) as depicted in FIG. 26. The centralized operation panel 5111 is provided in the operating room, and the user can suitably operate the apparatus existing in the operating room through the centralized operation panel 5111 as described hereinabove.

In the following, a configuration of the endoscopic surgery system 5113 is described in detail. As depicted, the endoscopic surgery system 5113 includes an endoscope 5115, other surgical tools 5131, a supporting arm apparatus 5141 which supports the endoscope 5115 thereon, and a cart 5151 on which various apparatus for endoscopic surgery are mounted.

In endoscopic surgery, in place of incision of the abdominal wall to perform laparotomy, a plurality of tubular aperture devices called trocars 5139*a* to 5139*d* are used to puncture the abdominal wall. Then, a lens barrel 5117 of the endoscope 5115 and the other surgical tools 5131 are inserted into body cavity of the patient 5185 through the trocars 5139*a* to 5139*d*. In the example depicted, as the other surgical tools 5131, a pneumoperitoneum tube 5133, an energy device 5135 and forceps 5137 are inserted into body cavity of the patient 5185. Further, the energy device 5135 is a treatment tool for performing incision and peeling of a tissue, sealing of a blood vessel or the like by high frequency current or ultrasonic vibration. However, the surgical tools 5131 depicted are mere examples at all, and as the surgical tools 5131, various surgical tools which are generally used in endoscopic surgery such as, for example, tweezers or a retractor may be used.

An image of a surgical region in a body cavity of the patient 5185 picked up by the endoscope 5115 is displayed on a display apparatus 5155. The surgeon 5181 would use the energy device 5135 or the forceps 5137 while watching the image of the surgical region displayed on the display apparatus 5155 on the real time basis to perform such treatment as, for example, resection of an affected area. It is to be noted that, though not depicted, the pneumoperitoneum tube 5133, the energy device 5135, and the forceps 5137 are supported by the surgeon 5181, an assistant or the like during surgery.

(Supporting Arm Apparatus)

The supporting arm apparatus 5141 includes an arm unit 5145 extending from a base unit 5143. In the example depicted, the arm unit 5145 includes joint portions 5147*a*, 5147*b* and 5147*c* and links 5149*a* and 5149*b* and is driven under the control of an arm controlling apparatus 5159. The endoscope 5115 is supported by the arm unit 5145 such that the position and the posture of the endoscope 5115 are controlled. Consequently, stable fixation in position of the endoscope 5115 can be implemented.

(Endoscope)

The endoscope 5115 includes the lens barrel 5117 which has a region of a predetermined length from a distal end thereof to be inserted into a body cavity of the patient 5185, and a camera head 5119 connected to a proximal end of the lens barrel 5117. In the example depicted, the endoscope 5115 is depicted as a rigid endoscope having the lens barrel 5117 of the hard type. However, the endoscope 5115 may otherwise be configured as a flexible endoscope having the lens barrel 5117 of the flexible type.

The lens barrel 5117 has, at a distal end thereof, an opening in which an objective lens is fitted. A light source apparatus 5157 is connected to the endoscope 5115 such that light generated by the light source apparatus 5157 is introduced to a distal end of the lens barrel 5117 by a light guide extending in the inside of the lens barrel 5117 and is applied toward an observation target in a body cavity of the patient 5185 through the objective lens. It is to be noted that the endoscope 5115 may be a forward-viewing endoscope or may be an oblique-viewing endoscope or a side-viewing endoscope.

An optical system and an image pickup element are provided in the inside of the camera head 5119 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5153. It is to be noted that the camera head 5119 has a function incorporated therein for suitably driving the optical system of the camera head 5119 to adjust the magnification and the focal distance.

It is to be noted that, in order to establish compatibility with, for example, a stereoscopic vision (3D display), a plurality of image pickup elements may be provided on the camera head 5119. In this case, a plurality of relay optical systems are provided in the inside of the lens barrel 5117 in order to guide observation light to the plurality of respective image pickup elements.

(Various Apparatus Incorporated in Cart)

The CCU 5153 includes a central processing unit (CPU), a graphics processing unit (GPU) or the like and integrally controls operation of the endoscope 5115 and the display apparatus 5155. Specifically, the CCU 5153 performs, for an image signal received from the camera head 5119, various image processes for displaying an image based on the image signal such as, for example, a development process (demosaic process). The CCU 5153 provides the image signal for which the image processes have been performed to the display apparatus 5155. Further, the audiovisual controller 5107 depicted in FIG. 26 is connected to the CCU 5153. The CCU 5153 provides the image signal for which the image processes have been performed also to the audiovisual controller 5107. Further, the CCU 5153 transmits a control signal to the camera head 5119 to control driving of the camera head 5119. The control signal may include information relating to an image pickup condition such as a magnification or a focal distance. The information relating to an image pickup condition may be inputted through the inputting apparatus 5161 or may be inputted through the centralized operation panel 5111 described hereinabove.

The display apparatus 5155 displays an image based on an image signal for which the image processes have been performed by the CCU 5153 under the control of the CCU 5153. If the endoscope 5115 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5155. Where the apparatus is ready for imaging of a high resolution such as 4K or 8K, if the display apparatus used as the display apparatus 5155 has a size of equal to or not less than 55 inches, then a more immersive experience can be obtained. Further, a plurality of display apparatus 5155 having different resolutions and/or different sizes may be provided in accordance with purposes.

The light source apparatus 5157 includes a light source such as, for example, a light emitting diode (LED) and supplies irradiation light for imaging of a surgical region to the endoscope 5115.

The arm controlling apparatus 5159 includes a processor such as, for example, a CPU and operates in accordance with a predetermined program to control driving of the arm unit 5145 of the supporting arm apparatus 5141 in accordance with a predetermined controlling method.

An inputting apparatus 5161 is an input interface for the endoscopic surgery system 5113. A user can perform inputting of various kinds of information or instruction inputting to the endoscopic surgery system 5113 through the inputting apparatus 5161. For example, the user would input various kinds of information relating to surgery such as physical information of a patient, information regarding a surgical procedure of the surgery and so forth through the inputting apparatus 5161. Further, the user would input, for example, an instruction to drive the arm unit 5145, an instruction to change an image pickup condition (type of irradiation light, magnification, focal distance or the like) by the endoscope 5115, an instruction to drive the energy device 5135 or a like through the inputting apparatus 5161.

The type of the inputting apparatus 5161 is not limited and may be that of any one of various known inputting apparatus. As the inputting apparatus 5161, for example, a mouse, a keyboard, a touch panel, a switch, a foot switch 5171 and/or a lever or the like may be applied. Where a touch panel is used as the inputting apparatus 5161, it may be provided on the display face of the display apparatus 5155.

The inputting apparatus 5161 is otherwise a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5161 includes a camera which can detect a motion of a user, and various kinds of inputting are performed in response to a gesture or a line of sight of a user detected from a video picked up by the camera. Further, the inputting apparatus 5161 includes a microphone which can collect the voice of a user, and various kinds of inputting are performed by voice through the microphone. By configuring the inputting apparatus 5161 such that various kinds of information can be inputted in a contactless fashion in this manner, especially a user who belongs to a clean area (for example, the surgeon 5181) can operate an apparatus belonging to an unclean area in a contactless fashion. Further, since the user can operate an apparatus without releasing a possessed surgical tool from its hand, the convenience to the user is improved.

A treatment tool controlling apparatus 5163 controls driving of the energy device 5135 for cautery or incision of a tissue, sealing of a blood vessel or the like. A pneumoperitoneum apparatus 5165 feeds gas into a body cavity of the patient 5185 through the pneumoperitoneum tube 5133 to inflate the body cavity in order to secure the field of view of the endoscope 5115 and secure the working space for the surgeon. A recorder 5167 is an apparatus capable of recording various kinds of information relating to surgery. A printer 5169 is an apparatus capable of printing various kinds of information relating to surgery in various forms such as a text, an image or a graph.

In the following, especially a characteristic configuration of the endoscopic surgery system 5113 is described in more detail.

(Supporting Arm Apparatus)

The supporting arm apparatus 5141 includes the base unit 5143 serving as a base, and the arm unit 5145 extending from the base unit 5143. In the example depicted, the arm unit 5145 includes the plurality of joint portions 5147a, 5147b and 5147c and the plurality of links 5149a and 5149b connected to each other by the joint portion 5147b. In FIG. 28, for simplified illustration, the configuration of the arm unit 5145 is depicted in a simplified form. Actually, the shape, number and arrangement of the joint portions 5147a to 5147c and the links 5149a and 5149b and the direction and so forth of axes of rotation of the joint portions 5147a to 5147c can be set suitably such that the arm unit 5145 has a desired degree of freedom. For example, the arm unit 5145 may preferably be included such that it has a degree of freedom equal to or not less than 6 degrees of freedom. This makes it possible to move the endoscope 5115 freely within the movable range of the arm unit 5145. Consequently, it becomes possible to insert the lens barrel 5117 of the endoscope 5115 from a desired direction into a body cavity of the patient 5185.

An actuator is provided in the joint portions 5147a to 5147c, and the joint portions 5147a to 5147c include such that they are rotatable around predetermined axes of rotation thereof by driving of the actuator. The driving of the actuator is controlled by the arm controlling apparatus 5159 to control the rotational angle of each of the joint portions 5147a to 5147c thereby to control driving of the arm unit 5145. Consequently, control of the position and the posture of the endoscope 5115 can be implemented. Thereupon, the arm controlling apparatus 5159 can control driving of the arm unit 5145 by various known controlling methods such as force control or position control.

For example, if the surgeon 5181 suitably performs operation inputting through the inputting apparatus 5161 (including the foot switch 5171), then driving of the arm unit 5145 may be controlled suitably by the arm controlling apparatus 5159 in response to the operation input to control the position and the posture of the endoscope 5115. After the endoscope 5115 at the distal end of the arm unit 5145 is moved from an arbitrary position to a different arbitrary position by the control just described, the endoscope 5115 can be supported fixedly at the position after the movement. It is to be noted that the arm unit 5145 may be operated in a master-slave fashion. In this case, the arm unit 5145 may be remotely controlled by the user through the inputting apparatus 5161 which is placed at a place remote from the operating room.

Further, where force control is applied, the arm controlling apparatus 5159 may perform power-assisted control to drive the actuators of the joint portions 5147a to 5147c such that the arm unit 5145 may receive external force by the user and move smoothly following the external force. This makes it possible to move the arm unit 5145 with comparatively weak force when the user directly touches with and moves the arm unit 5145. Accordingly, it becomes possible for the user to move the endoscope 5115 more intuitively by a simpler and easier operation, and the convenience to the user can be improved.

Here, generally in endoscopic surgery, the endoscope 5115 is supported by a medical doctor called scopist. In contrast, where the supporting arm apparatus 5141 is used, the position of the endoscope 5115 can be fixed with a higher degree of certainty without hands, and therefore, an image of a surgical region can be obtained stably and surgery can be performed smoothly.

It is to be noted that the arm controlling apparatus 5159 may not necessarily be provided on the cart 5151. Further, the arm controlling apparatus 5159 may not necessarily be a single apparatus. For example, the arm controlling apparatus 5159 may be provided in each of the joint portions 5147a to 5147c of the arm unit 5145 of the supporting arm apparatus 5141 such that the plurality of arm controlling apparatus 5159 cooperate with each other to implement driving control of the arm unit 5145.

(Light Source Apparatus)

The light source apparatus 5157 supplies irradiation light upon imaging of a surgical region to the endoscope 5115. The light source apparatus 5157 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5157. Further, in this case, if laser beams from the RGB laser light sources are applied time-divisionally on an observation target and driving of the image pickup elements of the camera head 5119 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5157 may be controlled such that the intensity of light to be outputted is changed for each predetermined time. By controlling driving of the image pickup element of the camera head 5119 in synchronism with the timing of the change of the intensity of light to acquire images time-divisionally and synthesizing the images, an image of a high dynamic range free from underexposed blocked up shadows and overexposed highlights can be created.

Further, the light source apparatus 5157 may be configured to supply light of a predetermined wavelength band ready for special light observation. In special light observation, for example, by utilizing the wavelength dependency of absorption of light of a body tissue, narrow band light observation (narrow band imaging) of imaging a predetermined tissue such as a blood vessel of a superficial portion of the mucous membrane or the like in a high contrast is performed by applying light of a narrower wavelength band in comparison with irradiation light upon ordinary observation (namely, white light). Alternatively, in special light observation, fluorescent observation for obtaining an image from fluorescent light generated by irradiation of excitation light may also be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5157 can be configured to supply such narrow-band light and/or excitation light suitable for special light observation as described above.

(Camera Head and CCU)

Figure 29:
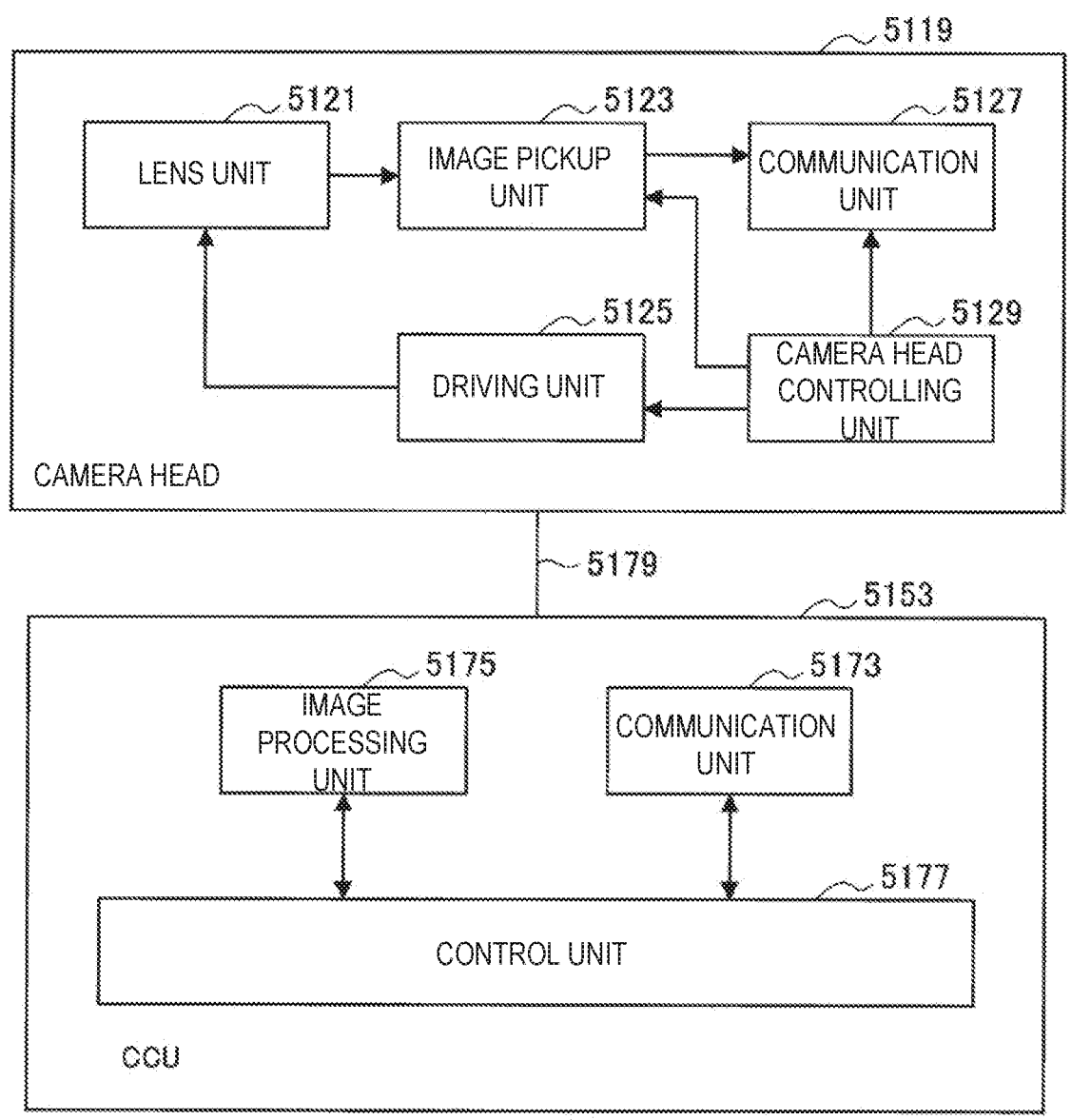
FIG. 29 is a block diagram depicting an example of a functional configuration of a camera head and a camera control unit (CCU) depicted in FIG. 28.

Functions of the camera head 5119 of the endoscope 5115 and the CCU 5153 are described in more detail with reference to FIG. 29. FIG. 29 is a block diagram depicting an example of a functional configuration of the camera head 5119 and the CCU 5153 depicted in FIG. 28.

Referring to FIG. 29, the camera head 5119 has, as functions thereof, a lens unit 5121, an image pickup unit 5123, a driving unit 5125, a communication unit 5127 and a camera head controlling unit 5129. Further, the CCU 5153 has, as functions thereof, a communication unit 5173, an image processing unit 5175 and a control unit 5177. The camera head 5119 and the CCU 5153 are connected to be bidirectionally communicable to each other by a transmission cable 5179.

First, a functional configuration of the camera head 5119 is described. The lens unit 5121 is an optical system provided at a connecting location of the camera head 5119 to the lens barrel 5117. Observation light taken in from a distal end of the lens barrel 5117 is introduced into the camera head 5119 and enters the lens unit 5121. The lens unit 5121 includes a combination of a plurality of lenses including a zoom lens and a focusing lens. The lens unit 5121 has optical properties adjusted such that the observation light is condensed on a light receiving face of the image pickup element of the image pickup unit 5123. Further, the zoom lens and the focusing lens include such that the positions thereof on their optical axis are movable for adjustment of the magnification and the focal point of a picked up image.

The image pickup unit 5123 includes an image pickup element and disposed at a succeeding stage to the lens unit 5121. Observation light having passed through the lens unit 5121 is condensed on the light receiving face of the image pickup element, and an image signal corresponding to the observation image is generated by photoelectric conversion. The image signal generated by the image pickup unit 5123 is provided to the communication unit 5127.

As the image pickup element which is included by the image pickup unit 5123, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5181 can comprehend a state of the surgical region in enhanced details and can proceed with the surgery more smoothly.

Further, the image pickup element which is included by the image pickup unit 5123 is configured such that it has a pair of image pickup elements for acquiring image signals for the right eye and the left eye compatible with 3D display. Where 3D display is applied, the surgeon 5181 can comprehend the depth of a living body tissue in the surgical region with a higher degree of accuracy. It is to be noted that, if the image pickup unit 5123 is configured as that of the multi-plate type, then a plurality of systems of lens units 5121 are provided corresponding to the individual image pickup elements of the image pickup unit 5123.

The image pickup unit 5123 may not necessarily be provided on the camera head 5119. For example, the image pickup unit 5123 may be provided just behind the objective lens in the inside of the lens barrel 5117.

The driving unit 5125 includes an actuator and moves the zoom lens and the focusing lens of the lens unit 5121 by a predetermined distance along the optical axis under the control of the camera head controlling unit 5129. Consequently, the magnification and the focal point of a picked up image by the image pickup unit 5123 can be adjusted suitably.

The communication unit 5127 includes a communication apparatus for transmitting and receiving various kinds of information to and from the CCU 5153. The communication unit 5127 transmits an image signal acquired from the image pickup unit 5123 as RAW data to the CCU 5153 through the transmission cable 5179. Thereupon, in order to display a picked up image of a surgical region in low latency, preferably the image signal is transmitted by optical communication. This is because, since, upon surgery, the surgeon 5181 performs surgery while observing the state of an affected area through a picked up image, in order to achieve surgery with a higher degree of safety and certainty, it is demanded for a moving image of the surgical region to be displayed on the real time basis as far as possible. Where optical communication is applied, a photoelectric conversion module for converting an electric signal into an optical signal is provided in the communication unit 5127. After the image signal is converted into an optical signal by the photoelectric conversion module, it is transmitted to the CCU 5153 through the transmission cable 5179.

Further, the communication unit 5127 receives a control signal for controlling driving of the camera head 5119 from the CCU 5153. The control signal includes information relating to image pickup conditions such as, for example, information that a frame rate of a picked up image is designated, information that an exposure value upon image picking up is designated and/or information that a magnification and a focal point of a picked up image are designated. The communication unit 5127 provides the received control signal to the camera head controlling unit 5129. It is to be noted that also the control signal from the CCU 5153 may be transmitted by optical communication. In this case, a photoelectric conversion module for converting an optical signal into an electric signal is provided in the communication unit 5127. After the control signal is converted into an electric signal by the photoelectric conversion module, it is provided to the camera head controlling unit 5129.

It is to be noted that the image pickup conditions such as the frame rate, exposure value, magnification or focal point are set automatically by the control unit 5177 of the CCU 5153 on the basis of an acquired image signal. In other words, an auto exposure (AE) function, an auto focus (AF) function and an auto white balance (AWB) function are incorporated in the endoscope 5115.

The camera head controlling unit 5129 controls driving of the camera head 5119 on the basis of a control signal from the CCU 5153 received through the communication unit 5127. For example, the camera head controlling unit 5129 controls driving of the image pickup element of the image pickup unit 5123 on the basis of information that a frame rate of a picked up image is designated and/or information that an exposure value upon image picking up is designated. Further, for example, the camera head controlling unit 5129 controls the driving unit 5125 to suitably move the zoom lens and the focus lens of the lens unit 5121 on the basis of information that a magnification and a focal point of a picked up image are designated. The camera head controlling unit 5129 may include a function for storing information for identifying of the lens barrel 5117 and/or the camera head 5119.

It is to be noted that, by disposing the components such as the lens unit 5121 and the image pickup unit 5123 in a sealed structure having high airtightness and high waterproof, the camera head 5119 can be provided with resistance to an autoclave sterilization process.

Now, a functional configuration of the CCU 5153 is described. The communication unit 5173 includes a communication apparatus for transmitting and receiving various kinds of information to and from the camera head 5119. The communication unit 5173 receives an image signal transmitted thereto from the camera head 5119 through the transmission cable 5179. Thereupon, the image signal may be transmitted preferably by optical communication as described above. In this case, for the compatibility with optical communication, the communication unit 5173 includes a photoelectric conversion module for converting an optical signal into an electric signal. The communication unit 5173 provides the image signal after conversion into an electric signal to the image processing unit 5175.

Further, the communication unit 5173 transmits, to the camera head 5119, a control signal for controlling driving of the camera head 5119. Also the control signal may be transmitted by optical communication.

The image processing unit 5175 performs various image processes for an image signal in the form of RAW data transmitted thereto from the camera head 5119. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5175 performs a detection process for an image signal for performing AE, AF and AWB.

The image processing unit 5175 includes a processor such as a CPU or a GPU, and when the processor operates in accordance with a predetermined program, the image processes and the detection process described above can be performed. It is to be noted that, where the image processing unit 5175 includes a plurality of GPUs, the image processing unit 5175 suitably divides information relating to an image signal such that image processes are performed in parallel by the plurality of GPUs.

The control unit 5177 performs various kinds of control relating to image picking up of a surgical region by the endoscope 5115 and display of the picked up image. For example, the control unit 5177 generates a control signal for controlling driving of the camera head 5119. Thereupon, if image pickup conditions are inputted by the user, then the control unit 5177 generates a control signal on the basis of the input by the user. Alternatively, where the endoscope 5115 has an AE function, an AF function and an AWB function incorporated therein, the control unit 5177 suitably calculates an optimum exposure value, focal distance and white balance in response to a result of a detection process by the image processing unit 5175 and generates a control signal.

Further, the control unit 5177 controls the display apparatus 5155 to display an image of a surgical region on the basis of an image signal for which the image processes have been performed by the image processing unit 5175. Thereupon, the control unit 5177 recognizes various objects in the surgical region image using various image recognition technologies. For example, the control unit 5177 can recognize a surgical tool such as forceps, a particular living body region, bleeding, mist when the energy device 5135 is used and so forth by detecting the shape, color and so forth of edges of the objects included in the surgical region image. The control unit 5177 causes, when it controls the display apparatus 5155 to display a surgical region image, various kinds of surgery supporting information to be displayed in an overlapping manner with an image of the surgical region using a result of the recognition. Where surgery supporting information is displayed in an overlapping manner and presented to the surgeon 5181, the surgeon 5181 can proceed with the surgery more safety and certainty.

The transmission cable 5179 which connects the camera head 5119 and the CCU 5153 to each other is an electric signal cable ready for communication of an electric signal, an optical fiber ready for optical communication or a composite cable thereof.

Here, while, in the example depicted in the figure, communication is performed by wired communication using the transmission cable 5179, the communication between the camera head 5119 and the CCU 5153 may be performed otherwise by wireless communication. Where the communication between the camera head 5119 and the CCU 5153 is performed by wireless communication, there is no necessity to lay the transmission cable 5179 in the operating room. Therefore, such a situation that movement of medical staff in the operating room is disturbed by the transmission cable 5179 can be eliminated.

An example of the operating room system 5100 to which the technology according to an embodiment of the present disclosure can be applied has been described above. It is to be noted here that, although a case in which the medical system to which the operating room system 5100 is applied is the endoscopic surgery system 5113 has been described as an example, the configuration of the operating room system 5100 is not limited to that of the example described above. For example, the operating room system 5100 may be applied to a soft endoscopic system for inspection or a microscopic surgery system in place of the endoscopic surgery system 5113.

The technology of the present disclosure is suitably applicable to the camera head 5119 illustrated in FIG. 29 among the above-described configurations. Specifically, the solid-state image pickup element 200 illustrated in FIG. 2 is used for the image pickup unit 5123 in the camera head 5119. The application of the solid-state image pickup element 200 reduces the number of times of readout at the time of pixel addition, so it is possible to reduce the power consumption of the operating room system 5100.

THIRD APPLICATION EXAMPLE

The technology according to the present disclosure can be applied to various products. For example, the technology according to the present disclosure may be applied to a microscopic surgery system used in so-called microsurgery which is performed while a minute region of a patient is enlarged and observed.

Figure 30:
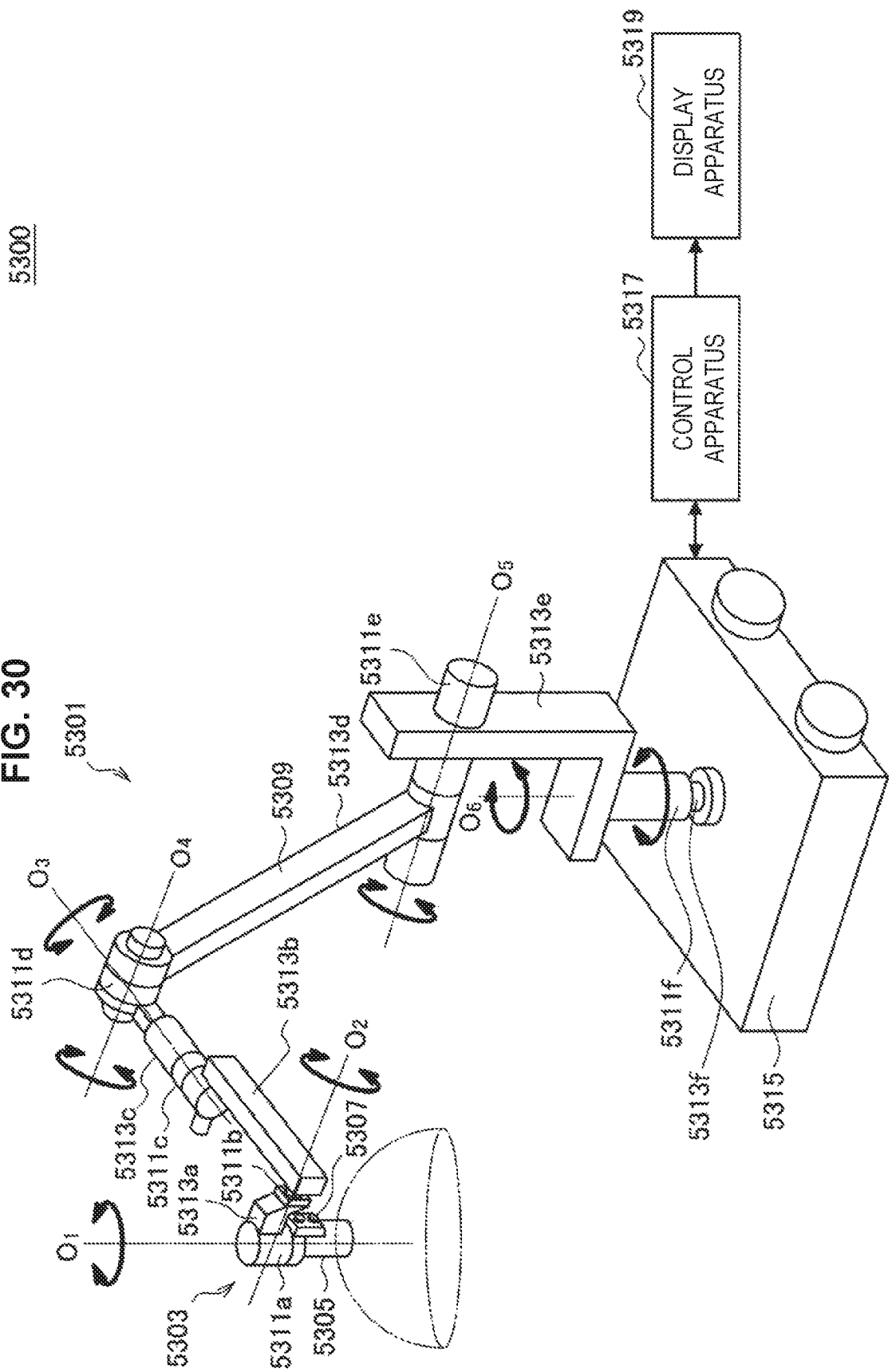
FIG. 30 is a view depicting an example of a schematic configuration of a microscopic surgery system.

FIG. 30 is a view depicting an example of a schematic configuration of a microscopic surgery system 5300 to which the technology according to an embodiment of the present disclosure can be applied. Referring to FIG. 30, the microscopic surgery system 5300 includes a microscope apparatus 5301, a control apparatus 5317 and a display apparatus 5319. It is to be noted that, in the description of the microscopic surgery system 5300, the term "user" signifies an arbitrary one of medical staff members such as a surgery or an assistant who uses the microscopic surgery system 5300.

The microscope apparatus 5301 has a microscope unit 5303 for enlarging an observation target (surgical region of a patient) for observation, an arm unit 5309 which supports the microscope unit 5303 at a distal end thereof, and a base unit 5315 which supports a proximal end of the arm unit 5309.

The microscope unit 5303 includes a cylindrical portion 5305 of a substantially cylindrical shape, an image pickup unit (not depicted) provided in the inside of the cylindrical portion 5305, and an operation unit 5307 provided in a partial region of an outer circumference of the cylindrical portion 5305. The microscope unit 5303 is a microscope unit of the electronic image pickup type (microscope unit of the video type) which picks up an image electronically by the image pickup unit.

A cover glass member for protecting the internal image pickup unit is provided at an opening face of a lower end of the cylindrical portion 5305. Light from an observation target (hereinafter referred to also as observation light) passes through the cover glass member and enters the image pickup unit in the inside of the cylindrical portion 5305. It is to be noted that a light source includes, for example, a light emitting diode (LED) or the like may be provided in the inside of the cylindrical portion 5305, and upon image picking up, light may be irradiated upon an observation target from the light source through the cover glass member.

The image pickup unit includes an optical system which condenses observation light, and an image pickup element which receives the observation light condensed by the optical system. The optical system includes a combination of a plurality of lenses including a zoom lens and a focusing lens. The optical system has optical properties adjusted such that the observation light is condensed to be formed image on a light receiving face of the image pickup element. The image pickup element receives and photoelectrically converts the observation light to generate a signal corresponding to the observation light, namely, an image signal corresponding to an observation image. As the image pickup element, for example, an image pickup element which has a Bayer array and is capable of picking up an image in color is used. The image pickup element may be any of various known image pickup elements such as a complementary metal oxide semiconductor (CMOS) image sensor or a charge coupled device (CCD) image sensor. The image signal generated by the image pickup element is transmitted as RAW data to the control apparatus 5317. Here, the transmission of the image signal may be performed suitably by optical communication. This is because, since, at a surgery site, the surgeon performs surgery while observing the state of an affected area through a picked up image, in order to achieve surgery with a higher degree of safety and certainty, it is demanded for a moving image of the surgical region to be displayed on the real time basis as far as possible. Where optical communication is used to transmit the image signal, the picked up image can be displayed with low latency.

It is to be noted that the image pickup unit may have a driving mechanism for moving the zoom lens and the focusing lens of the optical system thereof along the optical axis. Where the zoom lens and the focusing lens are moved suitably by the driving mechanism, the magnification of the picked up image and the focal distance upon image picking up can be adjusted. Further, the image pickup unit may incorporate therein various functions which may be provided generally in a microscopic unit of the electronic image pickup such as an auto exposure (AE) function or an auto focus (AF) function.

Further the image pickup unit may be configured as an image pickup unit of the single-plate type which includes a single image pickup element or may be configured as an image pickup unit of the multi-plate type which includes a plurality of image pickup elements. Where the image pickup unit is configured as that of the multi-plate type, for example, image signals corresponding to red, green, and blue colors may be generated by the image pickup elements and may be synthesized to obtain a color image. Alternatively, the image pickup unit may be configured such that it has a pair of image pickup elements for acquiring image signals for the right eye and the left eye compatible with a stereoscopic vision (three dimensional (3D) display). Where 3D display is applied, the surgeon can comprehend the depth of a living body tissue in the surgical region with a higher degree of accuracy. It is to be noted that, if the image pickup unit is configured as that of stereoscopic type, then a plurality of optical systems are provided corresponding to the individual image pickup elements.

The operation unit 5307 includes, for example, a cross lever, a switch or the like and accepts an operation input of the user. For example, the user can input an instruction to change the magnification of the observation image and the focal distance to the observation target through the operation unit 5307. The magnification and the focal distance can be adjusted by the driving mechanism of the image pickup unit suitably moving the zoom lens and the focusing lens in accordance with the instruction. Further, for example, the user can input an instruction to switch the operation mode of the arm unit 5309 (an all-free mode and a fixed mode hereinafter described) through the operation unit 5307. It is to be noted that when the user intends to move the microscope unit 5303, it is supposed that the user moves the microscope unit 5303 in a state in which the user grasps the microscope unit 5303 holding the cylindrical portion 5305. Accordingly, the operation unit 5307 is preferably provided at a position at which it can be operated readily by the fingers of the user with the cylindrical portion 5305 held such that the operation unit 5307 can be operated even while the user is moving the cylindrical portion 5305.

The arm unit 5309 is configured such that a plurality of links (first link 5313a to sixth link 53130 are connected for rotation relative to each other by a plurality of joint portions (first joint portion 5311a to sixth joint portion 5311f).

The first joint portion 5311a has a substantially columnar shape and supports, at a distal end (lower end) thereof, an upper end of the cylindrical portion 5305 of the microscope unit 5303 for rotation around an axis of rotation (first axis $O_1$) parallel to the center axis of the cylindrical portion 5305. Here, the first joint portion 5311a may be configured such that the first axis $O_1$ thereof is in alignment with the optical axis of the image pickup unit of the microscope unit 5303. By the configuration, if the microscope unit 5303 is rotated around the first axis $O_1$, then the field of view can be changed so as to rotate the picked up image.

The first link 5313a fixedly supports, at a distal end thereof, the first joint portion 5311a. Specifically, the first link 5313a is a bar-like member having a substantially L shape and is connected to the first joint portion 5311a such that one side at the distal end side thereof extends in a direction orthogonal to the first axis $O_1$ and an end portion of the one side abuts with an upper end portion of an outer periphery of the first joint portion 5311a. The second joint portion 5311*b* is connected to an end portion of the other side on the proximal end side of the substantially L shape of the first link 5313*a*.

The second joint portion 5311*b* has a substantially columnar shape and supports, at a distal end thereof, a proximal end of the first link 5313*a* for rotation around an axis of rotation (second axis $O_2$) orthogonal to the first axis $O_1$. The second link 5313*b* is fixedly connected at a distal end thereof to a proximal end of the second joint portion 5311*b*.

The second link 5313*b* is a bar-like member having a substantially L shape, and one side of a distal end side of the second link 5313*b* extends in a direction orthogonal to the second axis $O_2$ and an end portion of the one side is fixedly connected to a proximal end of the second joint portion 5311*b*. The third joint portion 5311*c* is connected to the other side at the proximal end side of the substantially L shape of the second link 5313*b*.

The third joint portion 5311*c* has a substantially columnar shape and supports, at a distal end thereof, a proximal end of the second link 5313*b* for rotation around an axis of rotation (third axis $O_3$) orthogonal to the first axis $O_1$ and the second axis $O_2$. The third link 5313*c* is fixedly connected at a distal end thereof to a proximal end of the third joint portion 5311*c*. By rotating the components at the distal end side including the microscope unit 5303 around the second axis $O_2$ and the third axis $O_3$, the microscope unit 5303 can be moved such that the position of the microscope unit 5303 is changed within a horizontal plane. In other words, by controlling the rotation around the second axis $O_2$ and the third axis $O_3$, the field of view of the picked up image can be moved within a plane.

The third link 5313*c* is configured such that the distal end side thereof has a substantially columnar shape, and a proximal end of the third joint portion 5311*c* is fixedly connected to the distal end of the columnar shape such that both of them have a substantially same center axis. The proximal end side of the third link 5313*c* has a prismatic shape, and the fourth joint portion 5311*d* is connected to an end portion of the third link 5313*c*.

The fourth joint portion 5311*d* has a substantially columnar shape and supports, at a distal end thereof, a proximal end of the third link 5313*c* for rotation around an axis of rotation (fourth axis $O_4$) orthogonal to the third axis $O_3$. The fourth link 5313*d* is fixedly connected at a distal end thereof to a proximal end of the fourth joint portion 5311*d*.

The fourth link 5313*d* is a bar-like member extending substantially linearly and is fixedly connected to the fourth joint portion 5311*d* such that it extends orthogonally to the fourth axis $O_4$ and abuts at an end portion of the distal end thereof with a side face of the substantially columnar shape of the fourth joint portion 5311*d*. The fifth joint portion 5311*e* is connected to a proximal end of the fourth link 5313*d*.

The fifth joint portion 5311*e* has a substantially columnar shape and supports, at a distal end side thereof, a proximal end of the fourth link 5313*d* for rotation around an axis of rotation (fifth axis $O_5$) parallel to the fourth axis $O_4$. The fifth link 5313*e* is fixedly connected at a distal end thereof to a proximal end of the fifth joint portion 5311*e*. The fourth axis $O_4$ and the fifth axis $O_5$ are axes of rotation around which the microscope unit 5303 can be moved in the upward and downward direction. By rotating the components at the distal end side including the microscope unit 5303 around the fourth axis $O_4$ and the fifth axis $O_5$, the height of the microscope unit 5303, namely, the distance between the microscope unit 5303 and an observation target, can be adjusted.

The fifth link 5313*e* includes a combination of a first member having a substantially L shape one side of which extends in the vertical direction and the other side of which extends in the horizontal direction, and a bar-like second member extending vertically downwardly from the portion of the first member which extends in the horizontal direction. The fifth joint portion 5311*e* is fixedly connected at a proximal end thereof to a neighboring upper end of a part extending the first member of the fifth link 5313*e* in the vertical direction. The sixth joint portion 5311*f* is connected to proximal end (lower end) of the second member of the fifth link 5313*e*.

The sixth joint portion 5311*f* has a substantially columnar shape and supports, at a distal end side thereof, a proximal end of the fifth link 5313*e* for rotation around an axis of rotation (sixth axis $O_6$) parallel to the vertical direction. The sixth link 5313*f* is fixedly connected at a distal end thereof to a proximal end of the sixth joint portion 5311*f*.

The sixth link 5313*f* is a bar-like member extending in the vertical direction and is fixedly connected at a proximal end thereof to an upper face of the base unit 5315.

The first joint portion 5311*a* to sixth joint portion 5311*f* have movable ranges suitably set such that the microscope unit 5303 can make a desired movement. Consequently, in the arm unit 5309 having the configuration described above, a movement of totaling six degrees of freedom including three degrees of freedom for translation and three degrees of freedom for rotation can be implemented with regard to a movement of the microscope unit 5303. By configuring the arm unit 5309 such that six degrees of freedom are implemented for movements of the microscope unit 5303 in this manner, the position and the posture of the microscope unit 5303 can be controlled freely within the movable range of the arm unit 5309. Accordingly, it is possible to observe a surgical region from every angle, and surgery can be executed more smoothly.

It is to be noted that the configuration of the arm unit 5309 as depicted is an example at all, and the number and shape (length) of the links including the arm unit 5309 and the number, location, direction of the axis of rotation and so forth of the joint portions may be designed suitably such that desired degrees of freedom can be implemented. For example, in order to freely move the microscope unit 5303, preferably the arm unit 5309 is configured so as to have six degrees of freedom as described above. However the arm unit 5309 may also be configured so as to have much greater degree of freedom (namely, redundant degree of freedom). Where a redundant degree of freedom exists, it is possible to change the posture of the arm unit 5309 in a state in which the position and the posture of the microscope unit 5303 are fixed. Accordingly, control can be implemented which is higher in convenience to the surgeon such as to control the posture of the arm unit 5309 such that, for example, the arm unit 5309 does not interfere with the field of view of the surgeon who watches the display apparatus 5319.

Here, an actuator in which a driving mechanism such as a motor, an encoder which detects an angle of rotation at each joint portion and so forth are incorporated may be provided for each of the first joint portion 5311*a* to sixth joint portion 5311*f*. By suitably controlling driving of the actuators provided in the first joint portion 5311*a* to sixth joint portion 5311*f* by the control apparatus 5317, the posture of the arm unit 5309, namely, the position and the posture of the microscope unit 5303, can be controlled. Specifically, the control apparatus 5317 can comprehend the posture of the arm unit 5309 at present and the position and the posture of the microscope unit 5303 at present on the basis of information regarding the angle of rotation of the joint portions detected by the encoders. The control apparatus 5317 uses the comprehended information to calculate a control value (for example, an angle of rotation or torque to be generated) for each joint portion with which a movement of the microscope unit 5303 in accordance with an operation input from the user is implemented. Accordingly the control apparatus 5317 drives driving mechanism of the each joint portion in accordance with the control value. It is to be noted that, in this case, the control method of the arm unit 5309 by the control apparatus 5317 is not limited, and various known control methods such as force control or position control may be applied.

For example, when the surgeon performs operation inputting suitably through an inputting apparatus not depicted, driving of the arm unit 5309 may be controlled suitably in response to the operation input by the control apparatus 5317 to control the position and the posture of the microscope unit 5303. By this control, it is possible to support, after the microscope unit 5303 is moved from an arbitrary position to a different arbitrary position, the microscope unit 5303 fixedly at the position after the movement. It is to be noted that, as the inputting apparatus, preferably an inputting apparatus is applied which can be operated by the surgeon even if the surgeon has a surgical tool in its hand such as, for example, a foot switch taking the convenience to the surgeon into consideration. Further, operation inputting may be performed in a contactless fashion on the basis of gesture detection or line-of-sight detection in which a wearable device or a camera which is provided in the operating room is used. This makes it possible even for a user who belongs to a clean area to operate an apparatus belonging to an unclean area with a high degree of freedom. In addition, the arm unit 5309 may be operated in a master-slave fashion. In this case, the arm unit 5309 may be remotely controlled by the user through an inputting apparatus which is placed at a place remote from the operating room.

Further, where force control is applied, the control apparatus 5317 may perform power-assisted control to drive the actuators of the first joint portion 5311a to sixth joint portion 5311f such that the arm unit 5309 may receive external force by the user and move smoothly following the external force. This makes it possible to move, when the user holds and directly moves the position of the microscope unit 5303, the microscope unit 5303 with comparatively weak force. Accordingly, it becomes possible for the user to move the microscope unit 5303 more intuitively by a simpler and easier operation, and the convenience to the user can be improved.

Further, driving of the arm unit 5309 may be controlled such that the arm unit 5309 performs a pivot movement. The pivot movement here is a motion for moving the microscope unit 5303 such that the direction of the optical axis of the microscope unit 5303 is kept toward a predetermined point (hereinafter referred to as pivot point) in a space. Since the pivot movement makes it possible to observe the same observation position from various directions, more detailed observation of an affected area becomes possible. It is to be noted that, where the microscope unit 5303 is configured such that the focal distance thereof is fixed, preferably the pivot movement is performed in a state in which the distance between the microscope unit 5303 and the pivot point is fixed. In this case, the distance between the microscope unit 5303 and the pivot point may be adjusted to a fixed focal distance of the microscope unit 5303 in advance. By the configuration just described, the microscope unit 5303 comes to move on a hemispherical plane (schematically depicted in FIG. 30) having a diameter corresponding to the focal distance centered at the pivot point, and even if the observation direction is changed, a clear picked up image can be obtained. On the other hand, where the microscope unit 5303 is configured such that the focal distance thereof is adjustable, the pivot movement may be performed in a state in which the distance between the microscope unit 5303 and the pivot point is variable. In this case, for example, the control apparatus 5317 may calculate the distance between the microscope unit 5303 and the pivot point on the basis of information regarding the angles of rotation of the joint portions detected by the encoders and automatically adjust the focal distance of the microscope unit 5303 on the basis of a result of the calculation. Alternatively, where the microscope unit 5303 includes an AF function, adjustment of the focal distance may be performed automatically by the AF function every time the changing in distance caused by the pivot movement between the microscope unit 5303 and the pivot point.

Further, each of the first joint portion 5311a to sixth joint portion 5311f may be provided with a brake for constraining the rotation of the first joint portion 5311a to sixth joint portion 5311f. Operation of the brake may be controlled by the control apparatus 5317. For example, if it is intended to fix the position and the posture of the microscope unit 5303, then the control apparatus 5317 renders the brakes of the joint portions operative. Consequently, even if the actuators are not driven, the posture of the arm unit 5309, namely, the position and posture of the microscope unit 5303, can be fixed, and therefore, the power consumption can be reduced. When it is intended to move the position and the posture of the microscope unit 5303, the control apparatus 5317 may release the brakes of the joint portions and drive the actuators in accordance with a predetermined control method.

Such operation of the brakes may be performed in response to an operation input by the user through the operation unit 5307 described hereinabove. When the user intends to move the position and the posture of the microscope unit 5303, the user would operate the operation unit 5307 to release the brakes of the joint portions. Consequently, the operation mode of the arm unit 5309 changes to a mode in which rotation of the joint portions can be performed freely (all-free mode). On the other hand, if the user intends to fix the position and the posture of the microscope unit 5303, then the user would operate the operation unit 5307 to render the brakes of the joint portions operative. Consequently, the operation mode of the arm unit 5309 changes to a mode in which rotation of the joint portions is constrained (fixed mode).

The control apparatus 5317 integrally controls operation of the microscopic surgery system 5300 by controlling operation of the microscope apparatus 5301 and the display apparatus 5319. For example, the control apparatus 5317 renders the actuators of the first joint portion 5311a to sixth joint portion 5311f operative in accordance with a predetermined control method to control driving of the arm unit 5309. Further, for example, the control apparatus 5317 controls operation of the brakes of the first joint portion 5311a to sixth joint portion 5311f to change the operation mode of the arm unit 5309. Further, for example, the control apparatus 5317 performs various signal processes for an image signal acquired by the image pickup unit of the microscope unit 5303 of the microscope apparatus 5301 to generate image data for display and controls the display apparatus 5319 to display the generated image data. As the signal processes, various known signal processes such as, for example, a development process (demosaic process), an image quality improving process (a bandwidth enhancement process, a super-resolution process, a noise reduction (NR) process and/or an image stabilization process) and/or an enlargement process (namely, an electronic zooming process) may be performed.

It is to be noted that communication between the control apparatus 5317 and the microscope unit 5303 and communication between the control apparatus 5317 and the first joint portion 5311a to sixth joint portion 5311f may be wired communication or wireless communication. Where wired communication is applied, communication by an electric signal may be performed or optical communication may be performed. In this case, a cable for transmission used for wired communication may be configured as an electric signal cable, an optical fiber or a composite cable of them in response to an applied communication method. On the other hand, where wireless communication is applied, since there is no necessity to lay a transmission cable in the operating room, such a situation that movement of medical staff in the operating room is disturbed by a transmission cable can be eliminated.

The control apparatus 5317 may be a processor such as a central processing unit (CPU) or a graphics processing unit (GPU), or a microcomputer or a control board in which a processor and a storage element such as a memory are incorporated. The various functions described hereinabove can be implemented by the processor of the control apparatus 5317 operating in accordance with a predetermined program. It is to be noted that, in the example depicted, the control apparatus 5317 is provided as an apparatus separate from the microscope apparatus 5301. However, the control apparatus 5317 may be installed in the inside of the base unit 5315 of the microscope apparatus 5301 and configured integrally with the microscope apparatus 5301. The control apparatus 5317 may also include a plurality of apparatus. For example, microcomputers, control boards or the like may be disposed in the microscope unit 5303 and the first joint portion 5311a to sixth joint portion 5311f of the arm unit 5309 and connected for communication with each other to implement functions similar to those of the control apparatus 5317.

The display apparatus 5319 is provided in the operating room and displays an image corresponding to image data generated by the control apparatus 5317 under the control of the control apparatus 5317. In other words, an image of a surgical region picked up by the microscope unit 5303 is displayed on the display apparatus 5319. The display apparatus 5319 may display, in place of or in addition to an image of a surgical region, various kinds of information relating to the surgery such as physical information of a patient or information regarding a surgical procedure of the surgery. In this case, the display of the display apparatus 5319 may be switched suitably in response to an operation by the user. Alternatively, a plurality of such display apparatus 5319 may also be provided such that an image of a surgical region or various kinds of information relating to the surgery may individually be displayed on the plurality of display apparatus 5319. It is to be noted that, as the display apparatus 5319, various known display apparatus such as a liquid crystal display apparatus or an electro luminescence (EL) display apparatus may be applied.

Figure 31:
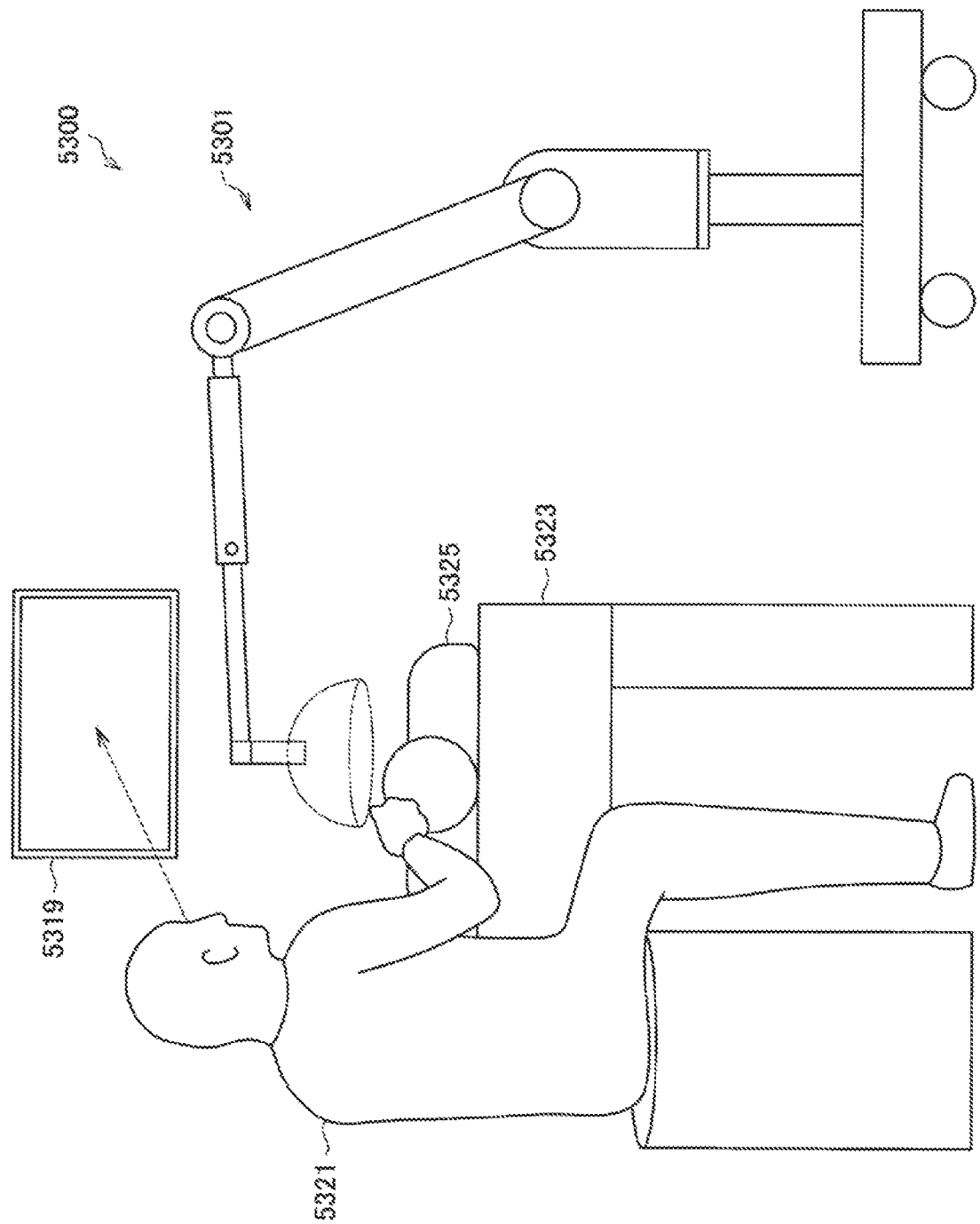
FIG. 31 is a view illustrating a state of surgery in which the microscopic surgery system depicted in FIG. 30 is used.

FIG. 31 is a view illustrating a state of surgery in which the microscopic surgery system 5300 depicted in FIG. 30 is used. FIG. 31 schematically illustrates a state in which a surgeon 5321 uses the microscopic surgery system 5300 to perform surgery for a patient 5325 on a patient bed 5323. It is to be noted that, in FIG. 31, for simplified illustration, the control apparatus 5317 from among the components of the microscopic surgery system 5300 is omitted and the microscope apparatus 5301 is depicted in a simplified from.

As depicted in FIG. 31, upon surgery, using the microscopic surgery system 5300, an image of a surgical region picked up by the microscope apparatus 5301 is displayed in an enlarged scale on the display apparatus 5319 installed on a wall face of the operating room. The display apparatus 5319 is installed at a position opposing to the surgeon 5321, and the surgeon 5321 would perform various treatments for the surgical region such as, for example, resection of the affected area while observing a state of the surgical region from a video displayed on the display apparatus 5319.

An example of the microscopic surgery system 5300 to which the technology according to an embodiment of the present disclosure can be applied has been described. It is to be noted here that, while the microscopic surgery system 5300 is described as an example, the system to which the technology according to an embodiment of the present disclosure can be applied is not limited to this example. For example, the microscope apparatus 5301 may also function as a supporting arm apparatus which supports, at a distal end thereof, a different observation apparatus or some other surgical tool in place of the microscope unit 5303. As the other observation apparatus, for example, an endoscope may be applied. Further, as the different surgical tool, forceps, tweezers, a pneumoperitoneum tube for pneumoperitoneum or an energy device for performing incision of a tissue or sealing of a blood vessel by cautery and so forth can be applied. By supporting any of such an observation apparatus and surgical tools as just described by the supporting apparatus, the position of them can be fixed with a high degree of stability in comparison with that in an alternative case in which they are supported by hands of medical staff. Accordingly, the burden on the medical staff can be reduced. The technology according to an embodiment of the present disclosure may be applied to a supporting arm apparatus which supports such a component as described above other than the microscopic unit.

The technology of the present disclosure is suitably applicable to the cylindrical portion 5305 illustrated in FIG. 30 among the above-described configurations. Specifically, the solid-state image pickup element 200 illustrated in FIG. 2 is used for the image pickup unit in the cylindrical portion 5305. The application of the solid-state image pickup element 200 reduces the number of times of readout at the time of pixel addition, so it is possible to reduce the power consumption of the microscopic surgery system 5300.

FOURTH APPLICATION EXAMPLE

The technology according to the present disclosure can be applied to various products. For example, the technology according to an embodiment of the present disclosure may be applied to a patient in-vivo information acquisition system using a capsule type endoscope.

Figure 32:
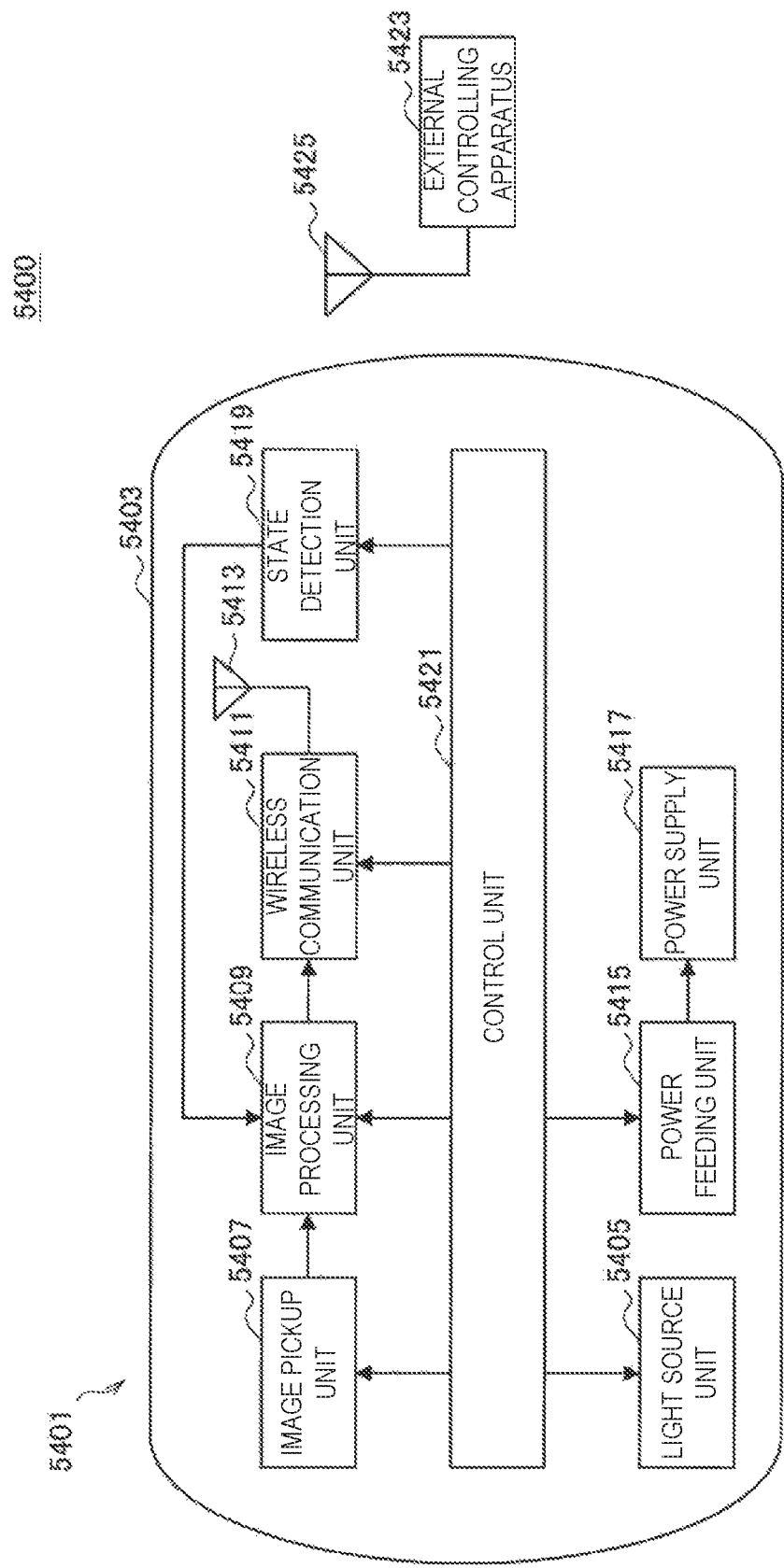
FIG. 32 is a block diagram depicting an example of a schematic configuration of an in-vivo information acquisition system.

FIG. 32 is a view depicting an example of a schematic configuration of an in-vivo information acquisition system 5400 to which the technology according to an embodiment of the present disclosure can be applied. Referring to FIG. 32, the in-vivo information acquisition system 5400 includes a capsule type endoscope 5401, and an external controlling apparatus 5423 which integrally controls operation of the in-vivo information acquisition system 5400. Upon inspection, the capsule type endoscope 5401 is swallowed by a patient. The capsule type endoscope 5401 has an image pickup function and a wireless communication function. For a period of time before the capsule type endoscope 5401 is discharged naturally from the patient, while it moves in the inside of an organ such as the stomach or the intestines by peristaltic motion, it successively picks up an image in the inside of each organ (hereinafter referred to as in-vivo image) at predetermined intervals and successively transmits information of the in-vivo images in wireless fashion to the external controlling apparatus 5423 located outside the body. The external controlling apparatus 5423 generates image data for displaying the in-vivo images on a display apparatus (not depicted) on the basis of the information of the received in-vivo images. In this manner, in the in-vivo information acquisition system 5400, a picked up image illustrating a state of the inside of the body of the patient can be obtained at any time after the capsule type endoscope 5401 is swallowed until it is discharged.

A configuration and functions of the capsule type endoscope 5401 and the external controlling apparatus 5423 are described in more detail. As depicted, the capsule type endoscope 5401 has functions of a light source unit 5405, an image pickup unit 5407, an image processing unit 5409, a wireless communication unit 5411, a power feeding unit 5415, a power supply unit 5417, a state detection unit 5419 and a control unit 5421 incorporated in a housing 5403 of the capsule type.

The light source unit 5405 includes a light source such as, for example, a light emitting diode (LED) and irradiates light upon an image pickup field of view of the image pickup unit 5407.

The image pickup unit 5407 includes an image pickup element and an optical system formed from a plurality of lenses provided at a preceding stage to the image pickup element. Reflected light (hereinafter referred to as observation light) of light irradiated upon a body tissue which is an observation target is condensed by the optical system and enters the image pickup element. The image pickup element receives and photoelectrically converts the observation light to generate an electric signal corresponding to the observation light, namely, an image signal corresponding to an observation image. The image signal generated by the image pickup unit 5407 is provided to the image processing unit 5409. It is to be noted that, as the image pickup element of the image pickup unit 5407, various known image pickup elements such as a complementary metal oxide semiconductor (CMOS) image sensor or a charge coupled device (CCD) image sensor may be used.

The image processing unit 5409 includes a processor such as a central processing unit (CPU) or a graphics processing unit (GPU) and performs various signal processes for an image signal generated by the image pickup unit 5407. The signal processes may be minimal processes for transmitting an image signal to the external controlling apparatus 5423 (for example, compression of image data, conversion of the frame rate, conversion of the data rate, and/or conversion of the format). Since the image processing unit 5409 is configured so as to perform only the minimal processes, the image processing unit 5409 can be implemented in a smaller size with lower power consumption. Therefore, the image processing unit 5409 is suitable for the capsule type endoscope 5401. However, if the space in the housing 5403 or the power consumption affords, then the image processing unit 5409 may perform a further signal process (for example, a noise removal process or some other image quality improving process). The image processing unit 5409 provides an image signal, for which the signal processes have been performed, as RAW data to the wireless communication unit 5411. It is to be noted that, when information regarding a state (motion, posture or the like) of the capsule type endoscope 5401 is acquired by the state detection unit 5419, the image processing unit 5409 may provide an image signal in a tied manner with the information to the wireless communication unit 5411. This makes it possible to associate the position inside the body at which an image is picked up, an image pickup direction of the image or the like with the picked up image.

The wireless communication unit 5411 includes a communication apparatus which can transmit and receive various kinds of information to and from the external controlling apparatus 5423. The communication apparatus includes an antenna 5413, a processing circuit which performs a modulation process and so forth for transmission and reception of a signal, and so forth. The wireless communication unit 5411 performs a predetermined process such as a modulation process for an image signal for which the signal processes have been performed by the image processing unit 5409, and transmits the resulting image signal to the external controlling apparatus 5423 through the antenna 5413. Further, the wireless communication unit 5411 receives a control signal relating to driving control of the capsule type endoscope 5401 from the external controlling apparatus 5423 through the antenna 5413. The wireless communication unit 5411 provides the received control signal to the control unit 5421.

The power feeding unit 5415 includes an antenna coil for power reception, a power regeneration circuit for regenerating electric power from electric current generated in the antenna coil, a voltage booster circuit and so forth. The power feeding unit 5415 generates electric power using the principle of non-contact charging. Specifically, if a magnetic field (electromagnetic wave) of a predetermined frequency is provided from the outside to the antenna coil of the power feeding unit 5415, then induced electromotive force is generated in the antenna coil. The electromagnetic wave may be a carrier transmitted from the external controlling apparatus 5423 through an antenna 5425. Electric power is regenerated from the induced electromotive force by the power regeneration circuit, and the potential of the electric power is suitably adjusted by the voltage booster circuit to generate electric power for charging. The electric power generated by the power feeding unit 5415 is stored into the power supply unit 5417.

The power supply unit 5417 includes a secondary battery and stores electric power generated by the power feeding unit 5415. In FIG. 32, in order to avoid complicated illustration, an arrow mark indicative of a supplying destination of electric power from the power supply unit 5417 and so forth are not depicted. However, electric power stored in the power supply unit 5417 is supplied to the light source unit 5405, the image pickup unit 5407, the image processing unit 5409, the wireless communication unit 5411, the state detection unit 5419 and the control unit 5421 and can be used for driving of them.

The state detection unit 5419 includes a sensor for detecting a state of the capsule type endoscope 5401 such as an acceleration sensor and/or a gyro sensor. The state detection unit 5419 can acquire information relating to a state of the capsule type endoscope 5401 from a result of detection by the sensor. The state detection unit 5419 provides the acquired information regarding a state of the capsule type endoscope 5401 to the image processing unit 5409. The image processing unit 5409 can tie the information regarding a state of the capsule type endoscope 5401 with an image signal as described hereinabove.

The control unit 5421 includes a processor such as a CPU and operates in accordance with a predetermined program to integrally control operation of the capsule type endoscope 5401. The control unit 5421 suitably controls driving of the light source unit 5405, the image pickup unit 5407, the image processing unit 5409, the wireless communication unit 5411, the power feeding unit 5415, the power supply unit 5417 and the state detection unit 5419 in accordance with a control signal transmitted thereto from the external controlling apparatus 5423 to implement such functions of the components as described above.

The external controlling apparatus 5423 may be a processor such as a CPU or a GPU, a microcomputer or a control board in which a processor and a storage element such as a memory are mixedly incorporated. The external controlling apparatus 5423 is configured such that it has an antenna 5425 and can transmit and receive various kinds of information to and from the capsule type endoscope 5401 through the antenna 5425. Specifically, the external controlling apparatus 5423 transmits a control signal to the control unit 5421 of the capsule type endoscope 5401 to control operation of the capsule type endoscope 5401. For example, an irradiation condition of light upon an observation target of the light source unit 5405 can be changed in accordance with a control signal from the external controlling apparatus 5423. Further, an image pickup condition (for example, a frame rate, an exposure value or the like of the image pickup unit 5407) can be changed in accordance with a control signal from the external controlling apparatus 5423. Further, the substance of processing by the image processing unit 5409 or a condition for transmitting an image signal from the wireless communication unit 5411 (for example, a transmission interval, a transmission image number or the like) may be changed in accordance with a control signal from the external controlling apparatus 5423.

Further, the external controlling apparatus 5423 performs various image processes for an image signal transmitted from the capsule type endoscope 5401 to generate image data for displaying a picked up in-vivo image on the display apparatus. As the image processes, various known signal processes may be performed such as, for example, a development process (demosaic process), an image quality improving process (bandwidth enhancement process, super-resolution process, noise reduction (NR) process, and/or image stabilization process) and/or an enlargement process (electronic zoom process) or the like. The external controlling apparatus 5423 controls driving of the display apparatus (not depicted) to cause the display apparatus to display a picked up in-vivo image on the basis of generated image data. Alternatively, the external controlling apparatus 5423 may control a recording apparatus (not depicted) to record generated image data or control a printing apparatus (not depicted) to output generated image data by printing.

5. APPLICATION EXAMPLE 2

The technology according to the present disclosure can be applied to various products. For example, the technology according to the present disclosure is implemented as apparatuses mounted on any type of mobile bodies such as automobiles, electric vehicles, hybrid electric vehicles, motorcycles, bicycles, personal mobilities, airplanes, drones, ships, robots, construction machines, and agricultural machines (tractors).

Figure 33:
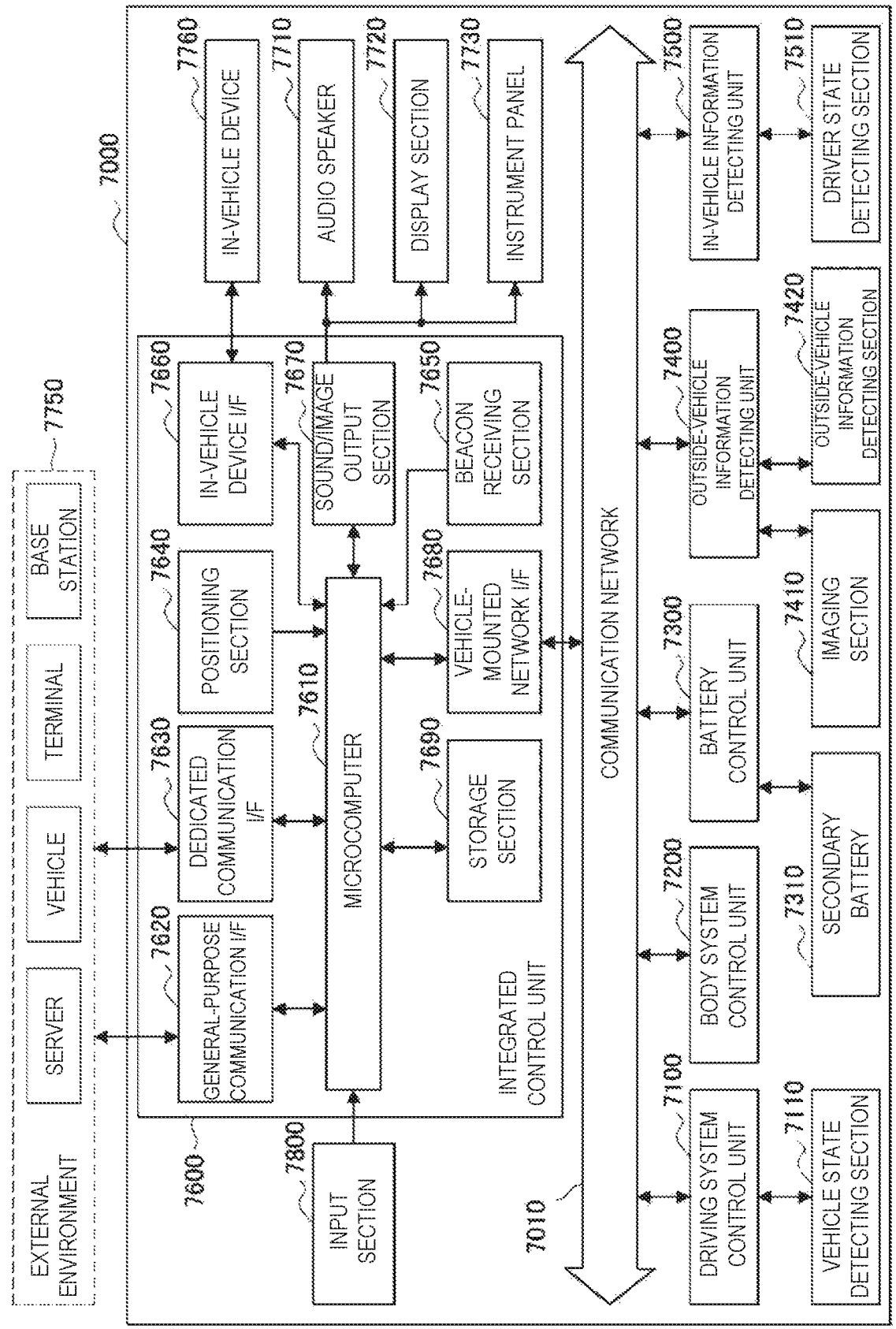
FIG. 33 is a block diagram depicting an example of schematic configuration of a vehicle control system.

FIG. 33 is a block diagram depicting an example of schematic configuration of a vehicle control system 7000 as an example of a mobile body control system to which the technology according to an embodiment of the present disclosure can be applied. The vehicle control system 7000 includes a plurality of electronic control units connected to each other via a communication network 7010. In the example depicted in FIG. 33, the vehicle control system 7000 includes a driving system control unit 7100, a body system control unit 7200, a battery control unit 7300, an outside-vehicle information detecting unit 7400, an in-vehicle information detecting unit 7500, and an integrated control unit 7600. The communication network 7010 connecting the plurality of control units to each other may, for example, be a vehicle-mounted communication network compliant with an arbitrary standard such as controller area network (CAN), local interconnect network (LIN), local area network (LAN), FlexRay, or the like.

Each of the control units includes: a microcomputer that performs arithmetic processing according to various kinds of programs; a storage section that stores the programs executed by the microcomputer, parameters used for various kinds of operations, or the like; and a driving circuit that drives various kinds of control target devices. Each of the control units further includes: a network interface (I/F) for performing communication with other control units via the communication network 7010; and a communication I/F for performing communication with a device, a sensor, or the like within and without the vehicle by wire communication or radio communication. A functional configuration of the integrated control unit 7600 illustrated in FIG. 33 includes a microcomputer 7610, a general-purpose communication I/F 7620, a dedicated communication I/F 7630, a positioning section 7640, a beacon receiving section 7650, an in-vehicle device I/F 7660, a sound/image output section 7670, a vehicle-mounted network I/F 7680, and a storage section 7690. The other control units similarly include a microcomputer, a communication I/F, a storage section, and the like.

The driving system control unit 7100 controls the operation of devices related to the driving system of the vehicle in accordance with various kinds of programs. For example, the driving system control unit 7100 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like. The driving system control unit 7100 may have a function as a control device of an antilock brake system (ABS), electronic stability control (ESC), or the like.

The driving system control unit 7100 is connected with a vehicle state detecting section 7110. The vehicle state detecting section 7110, for example, includes at least one of a gyro sensor that detects the angular velocity of axial rotational movement of a vehicle body, an acceleration sensor that detects the acceleration of the vehicle, and sensors for detecting an amount of operation of an accelerator pedal, an amount of operation of a brake pedal, the steering angle of a steering wheel, an engine speed or the rotational speed of wheels, and the like. The driving system control unit 7100 performs arithmetic processing using a signal input from the vehicle state detecting section 7110, and controls the internal combustion engine, the driving motor, an electric power steering device, the brake device, and the like.

The body system control unit 7200 controls the operation of various kinds of devices provided to the vehicle body in accordance with various kinds of programs. For example, the body system control unit 7200 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 7200. The body system control unit 7200 receives these input radio waves or signals, and controls a door lock device, the power window device, the lamps, or the like of the vehicle.

The battery control unit 7300 controls a secondary battery 7310, which is a power supply source for the driving motor, in accordance with various kinds of programs. For example, the battery control unit 7300 is supplied with information about a battery temperature, a battery output voltage, an amount of charge remaining in the battery, or the like from a battery device including the secondary battery 7310. The battery control unit 7300 performs arithmetic processing using these signals, and performs control for regulating the temperature of the secondary battery 7310 or controls a cooling device provided to the battery device or the like.

The outside-vehicle information detecting unit 7400 detects information about the outside of the vehicle including the vehicle control system 7000. For example, the outside-vehicle information detecting unit 7400 is connected with at least one of an imaging section 7410 and an outside-vehicle information detecting section 7420. The imaging section 7410 includes at least one of a time-of-flight (ToF) camera, a stereo camera, a monocular camera, an infrared camera, and other cameras. The outside-vehicle information detecting section 7420, for example, includes at least one of an environmental sensor for detecting current atmospheric conditions or weather conditions and a peripheral information detecting sensor for detecting another vehicle, an obstacle, a pedestrian, or the like on the periphery of the vehicle including the vehicle control system 7000.

The environmental sensor, for example, may be at least one of a rain drop sensor detecting rain, a fog sensor detecting a fog, a sunshine sensor detecting a degree of sunshine, and a snow sensor detecting a snowfall. The peripheral information detecting sensor may be at least one of an ultrasonic sensor, a radar device, and a LIDAR device (Light detection and Ranging device, or Laser imaging detection and ranging device). Each of the imaging section 7410 and the outside-vehicle information detecting section 7420 may be provided as an independent sensor or device, or may be provided as a device in which a plurality of sensors or devices are integrated.

Figure 34:
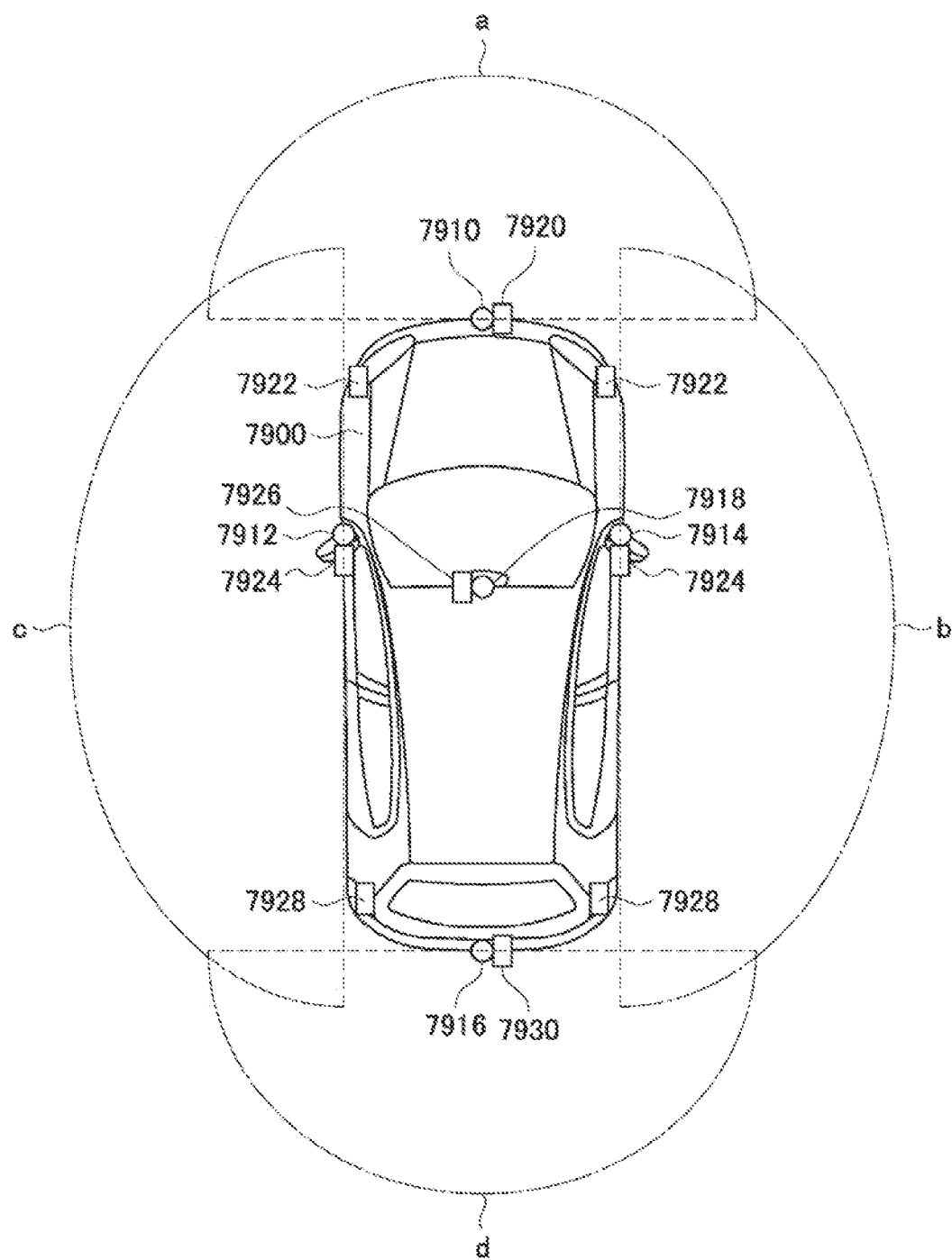
FIG. 34 is a diagram of assistance in explaining an example of installation positions of an outside-vehicle information detecting section and an imaging section.

FIG. 34 depicts an example of installation positions of the imaging section 7410 and the outside-vehicle information detecting section 7420. Imaging sections 7910, 7912, 7914, 7916, and 7918 are, for example, disposed at at least one of positions on a front nose, sideview mirrors, a rear bumper, and a back door of the vehicle 7900 and a position on an upper portion of a windshield within the interior of the vehicle. The imaging section 7910 provided to the front nose and the imaging section 7918 provided to the upper portion of the windshield within the interior of the vehicle obtain mainly an image of the front of the vehicle 7900. The imaging sections 7912 and 7914 provided to the sideview mirrors obtain mainly an image of the sides of the vehicle 7900. The imaging section 7916 provided to the rear bumper or the back door obtains mainly an image of the rear of the vehicle 7900. The imaging section 7918 provided to the upper portion of the windshield within the interior of the vehicle is used mainly to detect a preceding vehicle, a pedestrian, an obstacle, a signal, a traffic sign, a lane, or the like.

Incidentally, FIG. 34 depicts an example of photographing ranges of the respective imaging sections 7910, 7912, 7914, and 7916. An imaging range a represents the imaging range of the imaging section 7910 provided to the front nose. Imaging ranges b and c respectively represent the imaging ranges of the imaging sections 7912 and 7914 provided to the sideview mirrors. An imaging range d represents the imaging range of the imaging section 7916 provided to the rear bumper or the back door. A bird's-eye image of the vehicle 7900 as viewed from above can be obtained by superimposing image data imaged by the imaging sections 7910, 7912, 7914, and 7916, for example.

Outside-vehicle information detecting sections 7920, 7922, 7924, 7926, 7928, and 7930 provided to the front, rear, sides, and corners of the vehicle 7900 and the upper portion of the windshield within the interior of the vehicle may be, for example, an ultrasonic sensor or a radar device. The outside-vehicle information detecting sections 7920, 7926, and 7930 provided to the front nose of the vehicle 7900, the rear bumper, the back door of the vehicle 7900, and the upper portion of the windshield within the interior of the vehicle may be a LIDAR device, for example. These outside-vehicle information detecting sections 7920 to 7930 are used mainly to detect a preceding vehicle, a pedestrian, an obstacle, or the like.

Returning to FIG. 33, the description will be continued. The outside-vehicle information detecting unit 7400 makes the imaging section 7410 image an image of the outside of the vehicle, and receives imaged image data. In addition, the outside-vehicle information detecting unit 7400 receives detection information from the outside-vehicle information detecting section 7420 connected to the outside-vehicle information detecting unit 7400. In a case where the outside-vehicle information detecting section 7420 is an ultrasonic sensor, a radar device, or a LIDAR device, the outside-vehicle information detecting unit 7400 transmits an ultrasonic wave, an electromagnetic wave, or the like, and receives information of a received reflected wave. On the basis of the received information, the outside-vehicle information detecting unit 7400 may perform processing of detecting an object such as a human, a vehicle, an obstacle, a sign, a character on a road surface, or the like, or processing of detecting a distance thereto. The outside-vehicle information detecting unit 7400 may perform environment recognition processing of recognizing a rainfall, a fog, road surface conditions, or the like on the basis of the received information. The outside-vehicle information detecting unit 7400 may calculate a distance to an object outside the vehicle on the basis of the received information.

In addition, on the basis of the received image data, the outside-vehicle information detecting unit 7400 may perform image recognition processing of recognizing a human, a vehicle, an obstacle, a sign, a character on a road surface, or the like, or processing of detecting a distance thereto. The outside-vehicle information detecting unit 7400 may subject the received image data to processing such as distortion correction, alignment, or the like, and combine the image data imaged by a plurality of different imaging sections 7410 to generate a bird's-eye image or a panoramic image. The outside-vehicle information detecting unit 7400 may perform viewpoint conversion processing using the image data imaged by the imaging section 7410 including the different imaging parts.

The in-vehicle information detecting unit 7500 detects information about the inside of the vehicle. The in-vehicle information detecting unit 7500 is, for example, connected with a driver state detecting section 7510 that detects the state of a driver. The driver state detecting section 7510 may include a camera that images the driver, a biosensor that detects biological information of the driver, a microphone that collects sound within the interior of the vehicle, or the like. The biosensor is, for example, disposed in a seat surface, the steering wheel, or the like, and detects biological information of an occupant sitting in a seat or the driver holding the steering wheel. On the basis of detection information input from the driver state detecting section 7510, the in-vehicle information detecting unit 7500 may calculate a degree of fatigue of the driver or a degree of concentration of the driver, or may determine whether the driver is dozing. The in-vehicle information detecting unit 7500 may subject an audio signal obtained by the collection of the sound to processing such as noise canceling processing or the like.

The integrated control unit 7600 controls general operation within the vehicle control system 7000 in accordance with various kinds of programs. The integrated control unit 7600 is connected with an input section 7800. The input section 7800 is implemented by a device capable of input operation by an occupant, such, for example, as a touch panel, a button, a microphone, a switch, a lever, or the like. The integrated control unit 7600 may be supplied with data obtained by voice recognition of voice input through the microphone. The input section 7800 may, for example, be a remote control device using infrared rays or other radio waves, or an external connecting device such as a mobile telephone, a personal digital assistant (PDA), or the like that supports operation of the vehicle control system 7000. The input section 7800 may be, for example, a camera. In that case, an occupant can input information by gesture. Alternatively, data may be input which is obtained by detecting the movement of a wearable device that an occupant wears. Further, the input section 7800 may, for example, include an input control circuit or the like that generates an input signal on the basis of information input by an occupant or the like using the above-described input section 7800, and which outputs the generated input signal to the integrated control unit 7600. An occupant or the like inputs various kinds of data or gives an instruction for processing operation to the vehicle control system 7000 by operating the input section 7800.

The storage section 7690 may include a read only memory (ROM) that stores various kinds of programs executed by the microcomputer and a random access memory (RAM) that stores various kinds of parameters, operation results, sensor values, or the like. In addition, the storage section 7690 may be implemented by a magnetic storage device such as a hard disc drive (HDD) or the like, a semiconductor storage device, an optical storage device, a magneto-optical storage device, or the like.

The general-purpose communication I/F 7620 is a communication I/F used widely, which communication I/F mediates communication with various apparatuses present in an external environment 7750. The general-purpose communication I/F 7620 may implement a cellular communication protocol such as global system for mobile communications (GSM), worldwide interoperability for microwave access (WiMAX), long term evolution (LTE)), LTE-advanced (LTE-A), or the like, or another wireless communication protocol such as wireless LAN (referred to also as wireless fidelity (Wi-Fi), Bluetooth, or the like. The general-purpose communication I/F 7620 may, for example, connect to an apparatus (for example, an application server or a control server) present on an external network (for example, the Internet, a cloud network, or a company-specific network) via a base station or an access point. In addition, the general-purpose communication I/F 7620 may connect to a terminal present in the vicinity of the vehicle (which terminal is, for example, a terminal of the driver, a pedestrian, or a store, or a machine type communication (MTC) terminal) using a peer to peer (P2P) technology, for example.

The dedicated communication I/F 7630 is a communication I/F that supports a communication protocol developed for use in vehicles. The dedicated communication I/F 7630 may implement a standard protocol such, for example, as wireless access in vehicle environment (WAVE), which is a combination of institute of electrical and electronic engineers (IEEE) 802.11p as a lower layer and IEEE 1609 as a higher layer, dedicated short range communications (DSRC), or a cellular communication protocol. The dedicated communication I/F 7630 typically carries out V2X communication as a concept including one or more of communication between a vehicle and a vehicle (Vehicle to Vehicle), communication between a road and a vehicle (Vehicle to Infrastructure), communication between a vehicle and a home (Vehicle to Home), and communication between a pedestrian and a vehicle (Vehicle to Pedestrian).

The positioning section 7640, for example, performs positioning by receiving a global navigation satellite system (GNSS) signal from a GNSS satellite (for example, a GPS signal from a global positioning system (GPS) satellite), and generates positional information including the latitude, longitude, and altitude of the vehicle. Incidentally, the positioning section 7640 may identify a current position by exchanging signals with a wireless access point, or may obtain the positional information from a terminal such as a mobile telephone, a personal handyphone system (PHS), or a smart phone that has a positioning function.

The beacon receiving section 7650, for example, receives a radio wave or an electromagnetic wave transmitted from a radio station installed on a road or the like, and thereby obtains information about the current position, congestion, a closed road, a necessary time, or the like. Incidentally, the function of the beacon receiving section 7650 may be included in the dedicated communication I/F 7630 described above.

The in-vehicle device I/F 7660 is a communication interface that mediates connection between the microcomputer 7610 and various in-vehicle devices 7760 present within the vehicle. The in-vehicle device I/F 7660 may establish wireless connection using a wireless communication protocol such as wireless LAN, Bluetooth, near field communication (NFC), or wireless universal serial bus (WUSB). In addition, the in-vehicle device I/F 7660 may establish wired connection by universal serial bus (USB), high-definition multimedia interface (HDMI), mobile high-definition link (MHL), or the like via a connection terminal (and a cable if necessary) not depicted in the figures. The in-vehicle devices 7760 may, for example, include at least one of a mobile device and a wearable device possessed by an occupant and an information device carried into or attached to the vehicle. The in-vehicle devices 7760 may also include a navigation device that searches for a path to an arbitrary destination. The in-vehicle device I/F 7660 exchanges control signals or data signals with these in-vehicle devices 7760.

The vehicle-mounted network I/F 7680 is an interface that mediates communication between the microcomputer 7610 and the communication network 7010. The vehicle-mounted network I/F 7680 transmits and receives signals or the like in conformity with a predetermined protocol supported by the communication network 7010.

The microcomputer 7610 of the integrated control unit 7600 controls the vehicle control system 7000 in accordance with various kinds of programs on the basis of information obtained via at least one of the general-purpose communication I/F 7620, the dedicated communication I/F 7630, the positioning section 7640, the beacon receiving section 7650, the in-vehicle device I/F 7660, and the vehicle-mounted network I/F 7680. For example, the microcomputer 7610 may calculate a control target value for the driving force generating device, the steering mechanism, or the braking device on the basis of the obtained information about the inside and outside of the vehicle, and output a control command to the driving system control unit 7100. For example, the microcomputer 7610 may perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like. In addition, the microcomputer 7610 may perform cooperative control intended for automatic driving, which makes the vehicle to travel autonomously without depending on the operation of the driver, or the like, by controlling the driving force generating device, the steering mechanism, the braking device, or the like on the basis of the obtained information about the surroundings of the vehicle.

The microcomputer 7610 may generate three-dimensional distance information between the vehicle and an object such as a surrounding structure, a person, or the like, and generate local map information including information about the surroundings of the current position of the vehicle, on the basis of information obtained via at least one of the general-purpose communication I/F 7620, the dedicated communication I/F 7630, the positioning section 7640, the beacon receiving section 7650, the in-vehicle device I/F 7660, and the vehicle-mounted network I/F 7680. In addition, the microcomputer 7610 may predict danger such as collision of the vehicle, approaching of a pedestrian or the like, an entry to a closed road, or the like on the basis of the obtained information, and generate a warning signal. The warning signal may, for example, be a signal for producing a warning sound or lighting a warning lamp.

The sound/image output section 7670 transmits an output signal of at least one of a sound and an image to an output device capable of visually or auditorily notifying information to an occupant of the vehicle or the outside of the vehicle. In the example of FIG. 33, an audio speaker 7710, a display section 7720, and an instrument panel 7730 are illustrated as the output device. The display section 7720 may, for example, include at least one of an on-board display and a head-up display. The display section 7720 may have an augmented reality (AR) display function. The output device may be other than these devices, and may be another device such as headphones, a wearable device such as an eyeglass type display worn by an occupant or the like, a projector, a lamp, or the like. In a case where the output device is a display device, the display device visually displays results obtained by various kinds of processing performed by the microcomputer 7610 or information received from another control unit in various forms such as text, an image, a table, a graph, or the like. In addition, in a case where the output device is an audio output device, the audio output device converts an audio signal constituted of reproduced audio data or sound data or the like into an analog signal, and auditorily outputs the analog signal.

Incidentally, at least two control units connected to each other via the communication network 7010 in the example depicted in FIG. 33 may be integrated into one control unit. Alternatively, each individual control unit may include a plurality of control units. Further, the vehicle control system 7000 may include another control unit not depicted in the figures. In addition, part or the whole of the functions performed by one of the control units in the above description may be assigned to another control unit. That is, predetermined arithmetic processing may be performed by any of the control units as long as information is transmitted and received via the communication network 7010. Similarly, a sensor or a device connected to one of the control units may be connected to another control unit, and a plurality of control units may mutually transmit and receive detection information via the communication network 7010.

In the vehicle control system 7000 described above, the solid-state image pickup element 200 according to the present embodiment described with reference to FIG. 2 is applicable to the integrated control unit 7600 of the application example illustrated in FIG. 33. In one example, the solid-state image pickup element 200 corresponds to the imaging section 7410 of the integrated control unit 7600. In one example, the solid-state image pickup element 200 performs the pixel addition under the control of the integrated control unit 7600.

An example of the in-vivo information acquisition system 5400 to which the technology according to an embodiment of the present disclosure can be applied has been described above. The technology of the present disclosure is suitably applicable to the image pickup unit 5407 illustrated in FIG. 32 among the above-described configurations. Specifically, the solid-state image pickup element 200 illustrated in FIG. 2 is used for the image pickup unit 5407. The application of the solid-state image pickup element 200 reduces the number of times of readout at the time of pixel addition, so it is possible to reduce the power consumption of the in-vivo information acquisition system 5400.

The above-described embodiments are examples for embodying the present technology, and matters in the embodiments each have a corresponding relationship with disclosure-specific matters in the claims. Likewise, the matters in the embodiments and the disclosure-specific matters in the claims denoted by the same names have a corresponding relationship with each other. However, the present technology is not limited to the embodiments, and various modifications of the embodiments may be embodied in the scope of the present technology without departing from the spirit of the present technology.

The processing sequences that are described in the embodiments described above may be handled as a method having a series of sequences or may be handled as a program for causing a computer to execute the series of sequences and recording medium storing the program. As the recording medium, a CD (Compact Disc), an MD (MiniDisc), and a DVD (Digital Versatile Disc), a memory card, and a Blu-ray disc (registered trademark) can be used.

Note that effects described herein are not necessarily limitative, and any effect that is described in the present disclosure may be admitted.

Additionally, the present technology may also be configured as below.

(1)
A solid-state image pickup element including:
a predetermined number of blocks, each of which is provided with a plurality of normal pixels arranged in a predetermined direction;
a light shielding area in which the predetermined number of light shielding pixels are arranged in the predetermined direction, the light shielding pixels being connected to the respective blocks;
a scanning circuit configured to control each of the plurality of normal pixels in the block so that the block transfers electric charge to the light shielding pixel corresponding to the block; and
a signal processing unit provided, for each of the light shielding pixels, with a signal processing circuit configured to process a signal generated by the light shielding pixel on the basis of the transferred electric charge.

(2)
The solid-state image pickup element according to (1),
in which the normal pixel includes
a floating diffusion layer configured to accumulate the electric charge, and
a connection transistor configured to connect the light shielding pixel and the floating diffusion layer.

(3)
The solid-state image pickup element according to (2),
in which the normal pixel further includes a reset transistor configured to initialize an amount of the electric charge of the floating diffusion layer.

(4)
The solid-state image pickup element according to (2),
in which the connection transistor is a reset transistor configured to initialize the floating diffusion layer.

(5)
The solid-state image pickup element according to any of (2) to (4),
in which the row scanning circuit simultaneously transmits a reset signal used to instruct the floating diffusion layer to be initialized and a connection signal used to instruct the floating diffusion layer to be connected.

(6)
The solid-state image pickup element according to any of (2) to (4),
in which the row scanning circuit transmits a reset signal used to instruct the floating diffusion layer to be initialized and then transmits a connection signal used to instruct the floating diffusion layer to be connected.

(7)
The solid-state image pickup element according to (1),
in which the normal pixel includes
a photoelectric transducer configured to photoelectrically convert light to generate the electric charge, and
a connection transistor configured to connect the light shielding pixel and the photoelectric transducer.

(8)
The solid-state image pickup element according to any of (1) to (7),
in which the light shielding pixel includes
an electric charge accumulation unit configured to accumulate the transferred electric charge, and
an amplification transistor configured to amplify a signal corresponding to an amount of the accumulated electric charge.

(9)
The solid-state image pickup element according to (8),
in which the light shielding pixel further includes a photoelectric transducer.

(10)
The solid-state image pickup element according to any of (1) to (9),
in which each of the blocks includes a plurality of pixel blocks each provided with the plurality of normal pixels sharing a floating diffusion layer.

(11)
The solid-state image pickup element according to any of (1) to (9),
in which one of a pair of adjacent normal pixels among the plurality of normal pixels transfers the electric charge to another normal pixel of the pair of normal pixels under control of the row scanning circuit.

(12)
An image pickup apparatus including:
a predetermined number of blocks, each of which is provided with a plurality of normal pixels arranged in a predetermined direction;
a light shielding area in which the predetermined number of light shielding pixels are arranged in the predetermined direction, the light shielding pixels being connected to the respective blocks;
a scanning circuit configured to control each of the plurality of normal pixels in the block so that the block transfers electric charge to the light shielding pixel corresponding to the block;
a signal processing unit provided, for each of the light shielding pixels, with a signal processing circuit configured to create data by processing a signal generated by the light shielding pixel on the basis of the transferred electric charge; and
a recording unit configured to record the created data.

(13)
A method of controlling a solid-state image pickup element, the method including:
a scanning procedure of, in a pixel array section provided with a predetermined number of blocks each provided with a plurality of normal pixels arranged in a predetermined direction and a light shielding area in which the predetermined number of light shielding pixels connected to the respective blocks are arranged in the predetermined direction, controlling each of the plurality of normal pixels in the block so that the block transfers electric charge to the light shielding pixel corresponding to the block; and
a signal processing procedure of processing a signal generated by the light shielding pixel on the basis of the transferred electric charge.

REFERENCE SIGNS LIST 100 image pickup apparatus
110 image pickup lens
120 recording unit
130 image pickup control unit
200 solid-state image pickup element
210 row scanning circuit
220 pixel array section
221 light receiving area
222, 300 pixel block
223 light shielding area
224 addition block
230, 350, 360 normal pixel
231, 242, 309, 353 reset transistor
232, 241, 363 connection transistor
233, 246, 311, 354, 364 amplification transistor
234, 243, 301, 302, 305, 306, 312, 313, 317, 318, 352, 362 transfer transistor 235, 310, 356, 366 floating diffusion layer
236, 247, 314, 355, 365 selection transistor
237, 244, 303, 304, 307, 308, 315, 316, 319, 320, 351, 361 photoelectric transducer
240 light shielding pixel
250 DAC
255 constant current source
260 signal processing unit
261 AD converter
262 comparator
263 counter
270 timing control unit
280 column scanning circuit
290 image processing unit
5009, 5123, 5407, 7410 image pickup unit
5305 cylindrical portion

The invention claimed is:

1. A solid-state image pickup element, comprising:
   a plurality of blocks, wherein
      each of the plurality of blocks includes a plurality of normal pixels arranged in a specific direction,
      each of the plurality of normal pixels includes a floating diffusion layer and a connection transistor,
      floating diffusion layers of the plurality of normal pixels are configured to accumulate electric charge, and
      the connection transistor is a reset transistor configured to initialize the floating diffusion layer of each of the plurality of normal pixels;
   a light shielding area includes a plurality of light shielding pixels arranged in the specific direction, wherein each of the plurality of light shielding pixels is connected to a corresponding block of the plurality of blocks;
   a scanning circuit configured to control each of the plurality of normal pixels in each block of the plurality of blocks, wherein each block of the plurality of blocks is configured to transfer the electric charge to a corresponding light shielding pixel of the plurality of light shielding pixels; and
   a signal processing unit comprises a signal processing circuit for each of the plurality of light shielding pixels, wherein the signal processing circuit is configured to process a plurality of signals generated by the plurality of light shielding pixels based on the transferred electric charge.

2. The solid-state image pickup element according to claim 1, wherein each of the plurality of normal pixels further includes a reset transistor configured to initialize an amount of the electric charge of the corresponding floating diffusion layer.

3. The solid-state image pickup element according to claim 1, wherein the scanning circuit is further configured to simultaneously transmit a reset signal and a connection signal to each of the plurality of light shielding pixels, wherein the reset signal instructs each of the floating diffusion layer for initialization and the connection signal instructs each of the floating diffusion layer for connection.

4. The solid-state image pickup element according to claim 1, wherein
   the scanning circuit is further configured to transmit a reset signal and a connection signal to each of the plurality of light shielding pixels,
   the reset signal is transmitted before the connection signal,
   the reset signal instructs the floating diffusion layer for initialization, and
   the connection signal instructs the floating diffusion layer for connection.

5. The solid-state image pickup element according to claim 1, wherein
   each of the plurality of normal pixels includes a photoelectric transducer configured to photoelectrically convert light to generate the electric charge, and
   the connection transistor is configured to connect the corresponding light shielding pixel and the corresponding photoelectric transducer.

6. The solid-state image pickup element according to claim 1, wherein each of the plurality of light shielding pixels includes:
   an electric charge accumulation unit configured to accumulate the transferred electric charge, and
   an amplification transistor configured to amplify a signal corresponding to an amount of the accumulated electric charge.

7. The solid-state image pickup element according to claim 6, wherein each of the plurality of light shielding pixels further includes a photoelectric transducer.

8. The solid-state image pickup element according to claim 1, wherein a first normal pixel of a pair of adjacent normal pixels among the plurality of normal pixels is configured to transfer the electric charge to a second normal pixel of the pair of adjacent normal pixels based on a control of the scanning circuit.

9. An image pickup apparatus, comprising:
   a plurality of blocks, wherein
      each of the plurality of blocks includes a plurality of normal pixels arranged in a specific direction,
      each of the plurality of normal pixels includes a floating diffusion layer and a connection transistor,
      floating diffusion layers of the plurality of normal pixels are configured to accumulate electric charge, and
      the connection transistor is a reset transistor configured to initialize the floating diffusion layer of each of the plurality of normal pixels;
   a light shielding area includes a plurality of light shielding pixels arranged in the specific direction, wherein each of the plurality of light shielding pixels is connected to a corresponding block of the plurality of blocks;
   a scanning circuit configured to control each of the plurality of normal pixels in block of the plurality of blocks, wherein each block of the plurality of blocks is configured to transfer the electric charge to a corresponding light shielding pixel of the plurality of light shielding pixels;
   a signal processing unit comprises a signal processing circuit for each of the plurality of light shielding pixels, wherein the signal processing circuit is configured to create data by processing a plurality of signals generated by the plurality of light shielding pixels based on the transferred electric charge; and
   a recording unit configured to record the created data.

10. A method of controlling a solid-state image pickup element, the method comprising:
    a scanning procedure of, in a pixel array section that includes:
       a plurality of blocks, wherein each of the plurality of blocks includes a plurality of normal pixels arranged in a specific direction,
       each of the plurality of normal pixels includes a floating diffusion layer and a connection transistor,
       floating diffusion layers of the plurality of normal pixels are configured to accumulate electric charge, the connection transistor is a reset transistor configured to initialize the floating diffusion layer of each of the plurality of normal pixels, and a light shielding area that includes a plurality of light shielding pixels connected to a corresponding block of the plurality of blocks, and the plurality of light shielding pixels are arranged in the specific direction, controlling each of the plurality of normal pixels in the each block of the plurality of blocks, wherein each block of the plurality of blocks is configured to transfer the electric charge to a corresponding light shielding pixel of the plurality of light shielding pixels; and a signal processing procedure of processing a plurality of signals generated by the plurality of light shielding pixels based on the transferred electric charge.

11. A solid-state image pickup element, comprising:

a plurality of blocks, wherein
 each of the plurality of blocks includes a plurality of normal pixels arranged in a specific direction,
 each of the plurality of normal pixels includes a floating diffusion layer and a connection transistor, and
 floating diffusion layers of the plurality of normal pixels are configured to accumulate electric charge;

a light shielding area includes a plurality of light shielding pixels arranged in the specific direction, wherein each of the plurality of light shielding pixels is connected to a corresponding block of the plurality of blocks;

a scanning circuit configured to:
 control each of the plurality of normal pixels in each block of the plurality of blocks, wherein each block of the plurality of blocks is configured to transfer the electric charge to a corresponding light shielding pixel of the plurality of light shielding pixels, and
 control simultaneous transmission of a reset signal and a connection signal to each of the plurality of light shielding pixels, wherein the reset signal instructs each of the floating diffusion layer for initialization and the connection signal instructs each of the floating diffusion layer for connection; and a signal processing unit comprises a signal processing circuit for each of the plurality of light shielding pixels, wherein the signal processing circuit is configured to process a plurality of signals generated by the plurality of light shielding pixels based on the transferred electric charge.

* * * * *